United States Patent
Winkelmann, Jr. et al.

(10) Patent No.: US 11,525,666 B2
(45) Date of Patent: Dec. 13, 2022

(54) SPECTRAL CONTRAST OPTICAL COHERENCE TOMOGRAPHY ANGIOGRAPHY

(71) Applicant: Northwestern University, Evanston, IL (US)

(72) Inventors: James Arthur Winkelmann, Jr., Evanston, IL (US); Vadim Backman, Evanston, IL (US)

(73) Assignee: Northwestern University, Evanston, IL (US)

( * ) Notice: Subject to any disclaimer, the term of this patent is extended or adjusted under 35 U.S.C. 154(b) by 52 days.

(21) Appl. No.: 17/055,908

(22) PCT Filed: May 17, 2019

(86) PCT No.: PCT/US2019/032849
§ 371 (c)(1),
(2) Date: Nov. 16, 2020

(87) PCT Pub. No.: WO2019/222616
PCT Pub. Date: Nov. 21, 2019

(65) Prior Publication Data
US 2021/0207942 A1    Jul. 8, 2021

Related U.S. Application Data

(60) Provisional application No. 62/673,679, filed on May 18, 2018.

(51) Int. Cl.
*G01B 11/02* (2006.01)
*G01B 9/02091* (2022.01)
(Continued)

(52) U.S. Cl.
CPC .......... *G01B 9/02091* (2013.01); *A61B 3/102* (2013.01); *G01B 9/02044* (2013.01); *A61B 2576/02* (2013.01)

(58) Field of Classification Search
CPC ............ G01B 9/02091; G01B 9/02044; G01B 9/02007; A61B 3/102; A61B 3/1233; A61B 5/0066; A61B 5/0261; A61B 2576/02
See application file for complete search history.

(56) References Cited

U.S. PATENT DOCUMENTS

| 6,556,853 B1 | 4/2003 | Cabib et al. |
| 7,725,169 B2 * | 5/2010 | Boppart ............... A61B 5/0073 600/407 |

(Continued)

FOREIGN PATENT DOCUMENTS

| WO | WO 2016/127039 A2 | 8/2016 |
| WO | WO 2016/187141 A1 | 11/2016 |

OTHER PUBLICATIONS

Araki et al. (1996) "Comparison of mucosal microvasculature between the proximal and distal human colon," J. Electron. Microsc. 45, 202-206.

(Continued)

*Primary Examiner* — Tarifur R Chowdhury
*Assistant Examiner* — Jonathon Cook
(74) *Attorney, Agent, or Firm* — Leydig, Voit & Mayer, Ltd.

(57) ABSTRACT

In an aspect, a method for imaging a target comprises steps of: performing optical coherence tomography (OCT) scanning on the target with one or more beams of source light, the one or more beams of source light comprising a plurality of wavelengths; wherein performing OCT scanning comprises: providing the source light to a reference optical path and to a sample optical path, wherein providing the source light to a sample optical path comprises illuminating the target with the source light; and recording interference data corresponding to an interaction of a light from the reference optical path and a light from the sample optical path;

(Continued)

processing the interference data; and identifying blood or one or more blood-features in the target based on an optical attenuation of light in or associated with the sample optical path by the blood or the one or more blood-features.

17 Claims, 30 Drawing Sheets

(51) Int. Cl.
  *A61B 3/10* (2006.01)
  *G01B 9/02* (2022.01)

(56) References Cited

U.S. PATENT DOCUMENTS

| | | | |
|---|---|---|---|
| 9,619,903 | B2 | 4/2017 | Yi et al. |
| 9,678,007 | B2 | 6/2017 | Backman et al. |
| 9,962,075 | B2 | 5/2018 | Yi et al. |
| 10,524,664 | B2 | 1/2020 | Liu et al. |
| 10,881,273 | B2 | 1/2021 | Backman et al. |
| 2013/0314717 | A1 | 11/2013 | Yi et al. |
| 2015/0285685 | A1* | 10/2015 | Wax .................. G01B 9/02091 356/456 |
| 2015/0348287 | A1* | 12/2015 | Yi ........................ A61B 5/0261 382/131 |
| 2017/0188818 | A1 | 7/2017 | Yi et al. |
| 2018/0088048 | A1 | 3/2018 | Dong et al. |
| 2018/0206741 | A1* | 7/2018 | Saeki .................. A61B 5/0073 |
| 2018/0242844 | A1 | 8/2018 | Liu et al. |
| 2018/0256025 | A1 | 9/2018 | Yi et al. |
| 2019/0082952 | A1 | 3/2019 | Zhang et al. |

OTHER PUBLICATIONS

Barton et al. (2005) "Flow measurement without phase information in optical coherence tomography images," Opt. Express 13, 104-106.
Chen et al. (1997) "Noninvasive imaging of in vivo blood flow velocity using optical Doppler tomography," Opt. Lett. 22, 1119-1121.
Chen et al. (2015) "Measuring oxygen saturation in retinal and choroidal circulations in rats using visible light optical coherence tomography angiography," Biomed. Opt. Express 6, 2840-2853.
Chen et al. (2016) "Dual-band optical coherence tomography using a single supercontinuum laser source," J. Biomed. Opt. 21, 66013.
Chen et al. (2016) "Imaging hemodynamic response after ischemic stroke in mouse cortex using visible-light optical coherence tomography," Biomed. Opt. Express 7, 3377-3389.
Chen et al. (Feb. 2017) "Optical coherence tomography based angiography [Invited]," Biomed. Opt. Express 8, 1056-1082.
Chong et al. (2015) "Quantitative microvascular hemoglobin mapping using visible light spectroscopic optical coherence tomography," Biomed. Opt. Express 6, 1429-1450.
Fingler et al. (2007) "Mobility and transverse flow visualization using phase variance contrast with spectral domain optical coherence tomography," Opt. Express 15, 12636-12653.
Fingler et al. (2009) "Volumetric microvascular imaging of human retina using optical coherence tomography with a novel motion contrast technique," Opt. Express 17, 22190-22200.
Huang et al. (1991) "Optical coherence tomography," Science 254, 1178-1181.
International Search Report and Written Opinion dated Sep. 20, 2019 in International Application No. PCT/US2019/032849, 16 pp.
Jacques (2013) "Optical Properties of Biological Tissues: A Review," Phys. Med. Biol. 58, R37-61.
Jia et al. (2012) "Split-spectrum amplitude-decorrelation angiography with optical coherence tomography," Opt. Express 20, 4710-4725.
Leitgeb et al. (2003) "Real-time assessment of retinal blood flow with ultrafast acquisition by color Doppler Fourier domain optical coherence tomography," Opt. Express 11, 3116-3121.
Li et al. (2012) "Multispectral nanoparticle contrast agents for true-color spectroscopic optical coherence tomography," Biomed. Opt. Express 3, 1914-1923.
Liu et al. (Feb. 2017) "Theoretical model for optical oximetry at the capillary level: exploring hemoglobin oxygen saturation through backscattering of single red blood cells," J. Biomed. Opt. 22, 25002.
Liu et al. (Aug. 2018) "Single capillary oximetry and tissue ultrastructural sensing by dual-band dual-scan inverse spectroscopic optical coherence tomography," Light Sci. Appl. 7:57.
Makita et al. (2006) "Optical coherence angiography," Opt. Express 14, 7821-7840.
Michel et al. (2011) "Intraplaque haemorrhages as the trigger of plaque vulnerability," Eur. Heart J. 32, 1977-1985.
Pi et al. (Apr. 2018) "Automated spectroscopic retinal oximetry with visible-light optical coherence tomography," Biomed. Opt. Express 9, 2056-2067.
Robles et al. (2010) "Assessing hemoglobin concentration using spectroscopic optical coherence tomography for feasibility of tissue diagnostics," Biomed. Opt. Express 1, 310-317.
Robles et al. (2011) "Molecular imaging true-colour spectroscopic optical coherence tomography," Nat. Photonics 5, 744-747.
Spaide et al. (2016) "Image Artifacts in Optical Coherence Angiography," Retina 35, 2163-2180.
Vakhtin et al. (2003) "Common-path interferometer for frequency-domain optical coherence tomography," Applied Optics. 42(34), 6953-6958.
Van Heel et al. (2005) "Fourier shell correlation threshold criteria," J. Struct. Biol. 151, 250-262.
Von Der Weid et al. (2010) "Review article: Lymphatic system and associated adipose tissue in the development of inflammatory bowel disease," Aliment. Pharmacol. Ther. 32, 697-711.
Winkelmann et al. (Feb. 2018) "In vivo broadband visible light optical coherence tomography probe enables inverse spectroscopic analysis," Opt. Lett. 43, 619-622.
Winkelmann et al. (Jan. 2019) "Spectral contrast optical coherence tomography angiography enables single-scan vessel imaging," Light Sci Appl 8, 7. https://doi.org/10.1038/s41377-018-0117-7.
Winslow (2003) "Current status of blood substitute research: towards a new paradigm," J. Intern. Med. 253, 508-517.
Wojtkowski, et al. (Jul. 2002) "In vivo human retinal imaging by Fourier domain optical coherence tomography," Journal of Biomedical Optics 7(3):457-463.
Wojtkowski et al. (2004) "Ultrahigh-resolution, high-speed, Fourier domain optical coherence tomography and methods for dispersion compensation," Opt. Express 12, 2404-2422.
Yi et al. (2014) "Spatially resolved optical and ultrastructural properties of colorectal and pancreatic field carcinogenesis observed by inverse spectroscopic optical coherence tomography," J. Biomed. Opt. 19, 36013.
Yi et al. (2015) "Visible light optical coherence tomography measures retinal oxygen metabolic response to systemic oxygenation," Light Sci. Appl. 4, e334.
Zhu et al. (2010) "Imaging dermal blood flow through the intact rat skin with an optical clearing method," J. Biomed. Opt. 15, 26008.
U.S. Appl. No. 13/651,196, filed Oct. 12, 2012.
U.S. Appl. No. 13/902,288, filed May 24, 2013.
U.S. Appl. No. 14/638,714, filed Mar. 4, 2015.
U.S. Appl. No. 14/698,641, filed Apr. 28, 2015.
U.S. Appl. No. 15/751,107, filed Aug. 5, 2016.
U.S. Appl. No. 15/465,285, filed Mar. 21, 2017.
U.S. Appl. No. 15/583,615, filed May 1, 2017.
U.S. Appl. No. 15/584,018, filed May 1, 2017.
U.S. Appl. No. 15/972,753, filed May 7, 2018.
U.S. Appl. No. 16/123,518, filed Sep. 6, 2018.

* cited by examiner

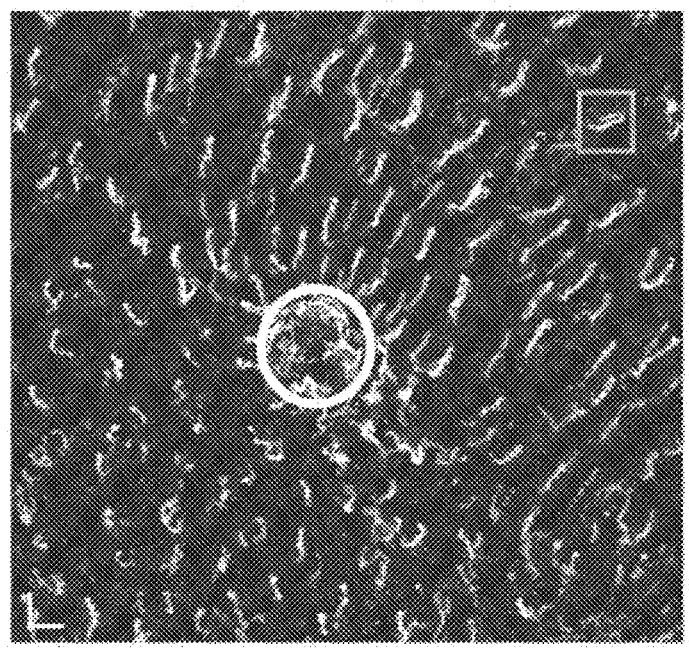
FIG. 10A
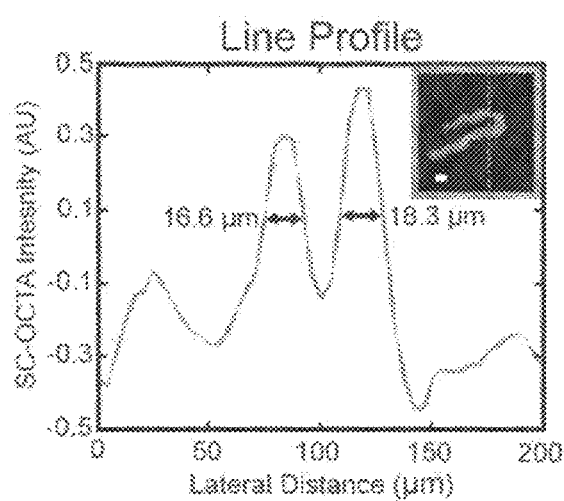 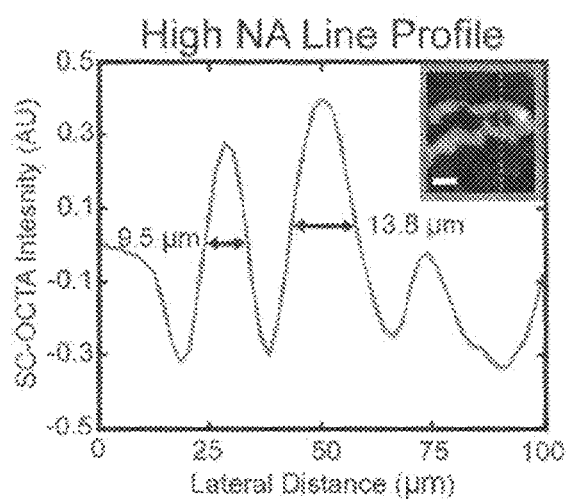
FIG. 10B  FIG. 10C

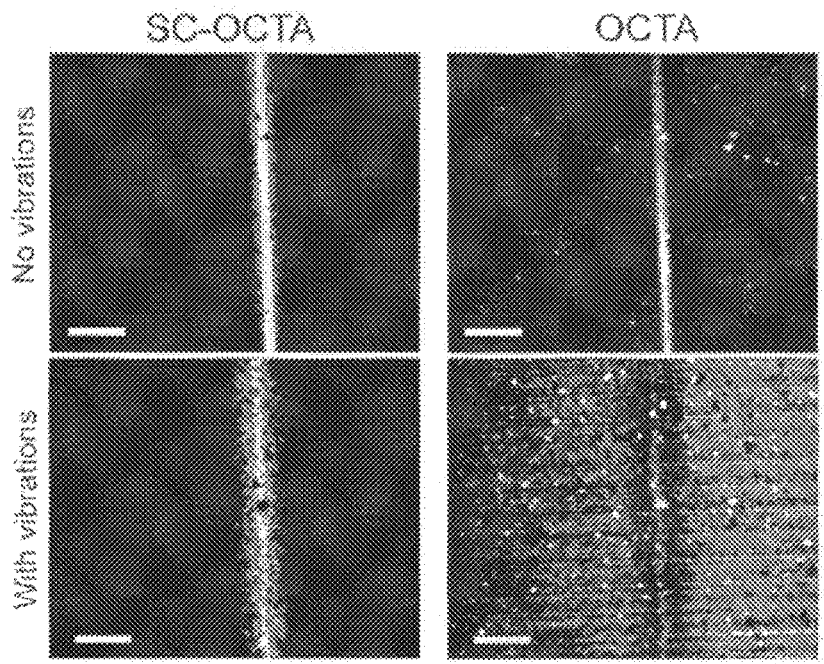
FIG. 11D
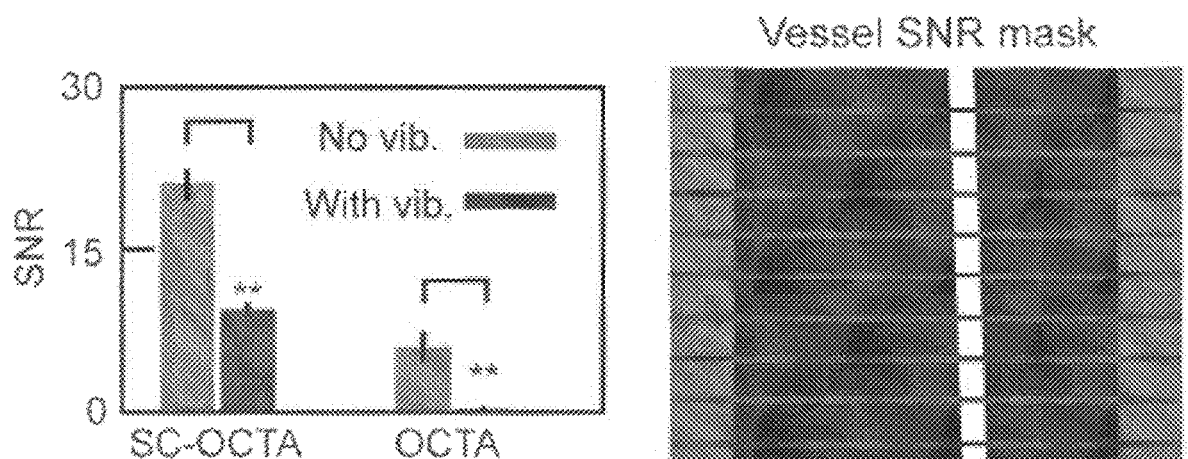
FIG. 11E
FIG. 11F

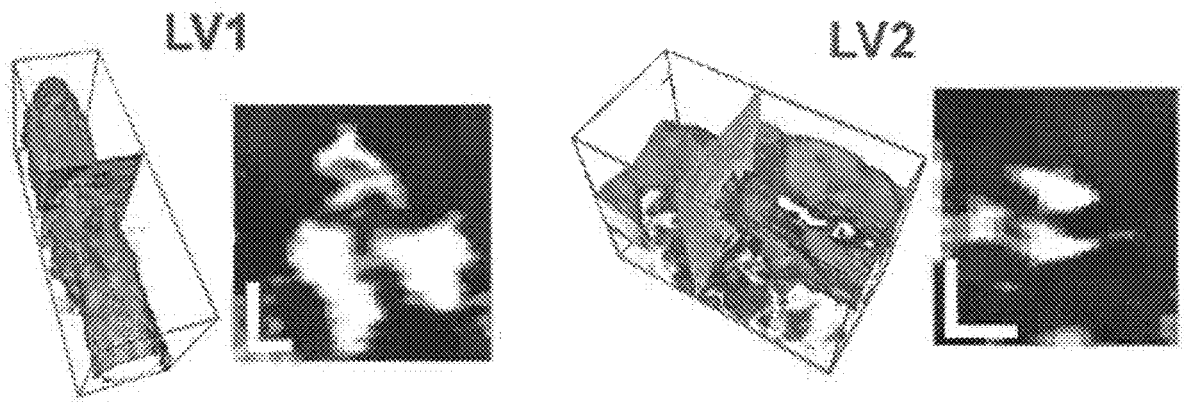
FIG. 15D
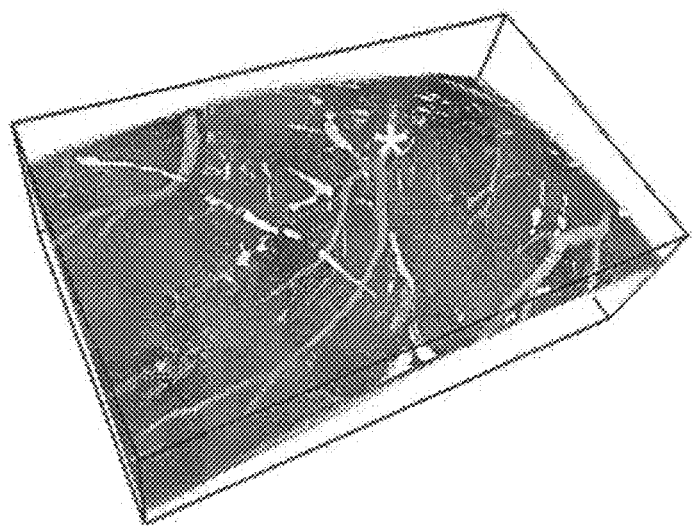
FIG. 15E
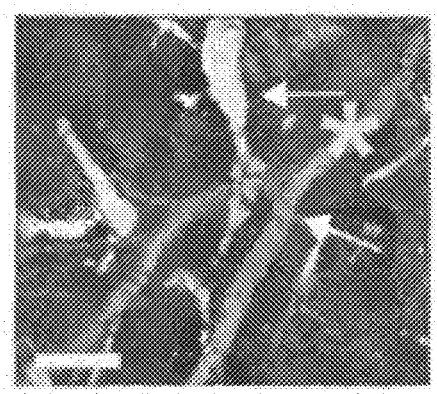 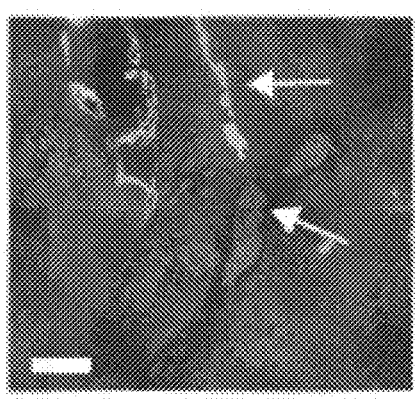
FIG. 15F  FIG. 15G

SPECTRAL CONTRAST OPTICAL COHERENCE TOMOGRAPHY ANGIOGRAPHY

CROSS-REFERENCE TO RELATED APPLICATIONS

This application is a U.S. National Stage Application filed under 35 U.S.C. 0371 of International Application No. PCT/US2019/032849, filed May 17, 2019 (Published as WO 2019/222616), which claims the benefit of and priority to U.S. Provisional Patent Application No. 62/673,679, filed May 18, 2018, each of which is hereby incorporated by reference in its entirety.

STATEMENT REGARDING FEDERALLY SPONSORED RESEARCH OR DEVELOPMENT

This invention was made with government support under RO1 CA183101 awarded by the National Institutes of Health. The government has certain rights in the invention.

BACKGROUND OF INVENTION

Optical coherence tomography (OCT) is a non-invasive optical imaging technique which produces depth-resolved reflectance imaging of samples through the use of a low coherence interferometer system. OCT imaging allows for three-dimensional (3D) visualization of structures in a variety of biological systems and non-biological systems not easily accessible through other imaging techniques. In some instances, OCT may provide a non-invasive, non-contact approach to assess information without disturbing or injuring a target or sample. In some examples, function optical coherence tomography (fOCT) can provide additional information regarding physical and chemical attributes inside vessels and structures, such as measurements of fluid flow. In medical applications, fOCT measurements can be used for diagnostic or monitoring purposes of a variety of fluids in the treatment of various diseases.

OCT is a non-invasive optical imaging modality providing micron-scale resolution of 3D tissue morphology within a lateral imaging range of several millimeters and penetration depth on the order of a millimeter into tissue. In addition to providing valuable structural information, enhanced processing of OCT signals can provide a milieu of other functional, structural, and molecular information. Early work in this regard harnessed the Doppler phase shift caused by backscattering from erythrocytes moving in vasculature to measure blood flow velocity and delineate vessels, referred to as Doppler OCT. This inherent motion in flowing blood is used to provide contrast to distinguish vasculature from surrounding tissue in OCT angiography. To achieve this contrast enhancement, algorithms utilizing phase variance, sequential scan subtraction, and speckle variance among others were developed and are successfully implemented to bring out vasculature in OCT scans of many tissues. Limitations of this approach towards OCT-based angiography include high sensitivity to sample movement, such as breathing and pulse movement in living animals, which commonly result in bright banding artifact across the projected OCT angiogram.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

Provided herein are methods, and systems, that address the above, and other, challenges in the art. These methods, and systems, disclosed herein may be used to provide detailed images of blood and tissue, for example, inside of a subject to improve medical diagnostics and treatment. These techniques utilize improved optical coherence tomography (OCT) approaches to provide for imaging and analysis that are faster, more accurate, more detailed, and less sensitive, or substantially insensitive, to motion of the imaged target compared to conventional techniques. Motion, such as that due to breathing, creates difficulty in using conventional OCT techniques for imaging a live target at least because conventional techniques require scanning a given area at least twice in order to image it. Also unlike conventional approaches, these methods and systems are sensitive to blood, whether it is flowing or stationary. In combining various steps, these methods and systems allow for virtually dissecting a target to image and differentiate blood, including hemostatic blood, from other tissue. Also provided herein are new probes, which optionally may be used according to any of the methods disclosed herein, that provide new and improved options for medical professionals, for example, to image areas within a subject, such as for endoscopy. Via new probe designs and combinations of optical features, for example, these probes minimize or eliminate various artifacts or hindering challenges associated with OCT imaging using flexible probes inside of a subject.

In an aspect, a method for imaging a target comprises steps of: performing optical coherence tomography (OCT) scanning on the target with one or more beams of source light, the one or more beams of source light comprising a plurality of wavelengths; wherein performing OCT scanning comprises: providing the source light to a reference optical path and to a sample optical path, wherein providing the source light to a sample optical path comprises illuminating the target with the source light; and recording interference data corresponding to an interaction of a light from the reference optical path and a light from the sample optical path; processing the interference data; and identifying blood or one or more blood-features in the target based on an optical attenuation of light in or associated with the sample optical path by the blood or the one or more blood-features.

According to any embodiment, the one or more blood features may comprise or may consist of hemoglobin, red blood cells, or any combination thereof. According to any embodiment, the method may comprise differentiating the blood or the one or more blood-features from one or more non-blood-features in the target. According to any embodiment, the one or more non-blood-features in the target may comprise or may consist of tissue, fat, lymph tissue, blood vessel wall, lymph vessel wall, bone, connective tissue, other tissue, cells, or fluid other than blood, or any combination of these. According to any embodiment, the one or more non-blood-features in the target may comprise or may consist of tissue, fat, lymph tissue, blood vessel wall, lymph vessel wall, bone, connective tissue, or any combination of these.

According to any embodiments, the step of processing may comprise: determining at least a first Fourier transform and a second Fourier transform from the interference data;

and determining at least one spectral contrast OCT (SC-OCT) characteristic based on the at least the first Fourier transform and the second Fourier transform. According to certain embodiments, the first Fourier transform corresponds to a first sampling window and the second Fourier transform corresponds to a second sampling window. According to any embodiments, the sampling window may correspond to a wavelength range selected from the range of 495 nm to 600 nm and the second sampling window may correspond to a wavelength range selected from the range of 500 nm and 750 nm. According to certain embodiments, the sampling window corresponds to a wavelength range selected from the range of 500 nm to 600 nm and the second sampling window corresponds to a wavelength range selected from the range of 550 nm and 700 nm. According to certain embodiments, the sampling window corresponds to a wavelength range selected from the range of 500 nm to 600 nm and the second sampling window corresponds to a wavelength range selected from the range of 550 nm and 700 nm. According to any of the embodiments disclosed herein, the first Fourier transform may be a first short time Fourier transform (STFT) and the second Fourier transform may be a second short time Fourier transform (STFT). According to any embodiments disclosed herein, the at least one SC-OCT characteristic may be at least one of a spectral contrast OCT (SC-OCT) ratio of the second Fourier transform to the first Fourier transform or a spectral contrast OCT (SC-OCT) difference between the second Fourier transform and the first Fourier transform. According to certain embodiments, the at least one SC-OCT characteristic is at least one of a spectral contrast OCT (SC-OCT) ratio of the second STFT to the first STFT and a spectral contrast OCT (SC-OCT) difference between the second STFT and the first STFT. According to any embodiments disclosed herein, the at least one SC-OCT characteristic may be at least one of a spectral contrast OCT (SC-OCT) ratio of the first Fourier transform to the second Fourier transform or a spectral contrast OCT (SC-OCT) difference between the first Fourier transform and the second Fourier transform. According to certain embodiments, the at least one SC-OCT characteristic is at least one of a spectral contrast OCT (SC-OCT) ratio of the first STFT to the second STFT and a spectral contrast OCT (SC-OCT) difference between the first STFT and the second STFT. According to certain embodiments, the method comprises generating a spectral contrast OCT (SC-OCT) image of the target using the SC-OCT characteristic. According to certain embodiments, the method comprises generating a spectral contrast OCT (SC-OCT) image of the target using at least one of the SC-OCT ratio and the SC-OCT difference. According to certain embodiments, the method comprises differentiating the blood or the one or more blood-features from the one or more non-blood-features in the target using the SC-OCT image. According to certain embodiments, the method comprises determining an inverse of at the least one of the first Fourier transform and the second Fourier transform. According to certain embodiments, the method comprises determining an inverse of at the least one of the first STFT and the second STFT. According to certain embodiments, the method comprises determining an inverse of the first STFT. According to certain embodiments, the method comprises generating an image based on the inverse of the at least one of the first Fourier transform and the second Fourier transform, the inverse of the at the least one of the first STFT and the second STFT, or the inverse of the first STFT. According to certain embodiments, the method comprises generating one or more three-dimensional (3D) images of the target using the inverse of the at least one of the first Fourier transform and the second Fourier transform (or, the inverse of the at the least one of the first STFT and the second STFT, or the inverse of the first STFT) and using the SC-OCT characteristic. According to certain embodiments, the method comprises performing a depth integration using the SC-OCT characteristic and generating a depth-integrated SC-OCT (DI-SC-OCT) image. According to certain embodiments, the SC-OCT image comprises a plurality of pixels and wherein performing depth integration comprises integrating data corresponding to each of the plurality of pixels along a depth and multiplying by data corresponding to the inverse of the at least one of the first Fourier transform and the second Fourier transform. According to certain embodiments, the method comprises acquiring full-spectrum OCT data of the target. According to certain embodiments, the method comprises acquiring full-spectrum OCT data of the target and generating one or more here-dimensional (3D) images of the target using at least two of the inverse of the at least one of the first Fourier transform and the second Fourier transform, the SC-OCT characteristic, and a full-spectrum OCT data. According to certain embodiments, the SC-OCT image is a three-dimensional depth-resolved image of the target. According to certain embodiments, the method comprises determining a normalized median backscattering data corresponding to blood or one or more blood-features and one or more non-blood-features in the target. According to any embodiment, the second sampling window, or center thereof, may correspond to longer wavelength(s) compared to the first sampling window, or center thereof. According to any of the embodiments, the step of determining at least a first Fourier transform and a second Fourier transform from the interference data may include determining three or more Fourier transforms, each independently corresponding to a unique sampling window, respectively.

Any of the methods and systems disclosed herein may include OCT scanning and processing according any one or a combination of the embodiments disclosed, such as those described below. According to certain embodiments, determining the first Fourier transform comprises determining a first window function and the first Fourier transform corresponds to the first window function; and wherein determining the second Fourier transform comprises determining a second window function and the second Fourier transform corresponds to the second window function. According to certain embodiments, the first window function corresponds to a first wavelength range and the second window function corresponds to a second wavelength range; and wherein the first wavelength range and the second wavelength range are substantially in the visible light range of the electromagnetic spectrum. According to certain embodiments, each of the first wavelength range or a center wavelength of the first wavelength range and the second wavelength range or a center wavelength of the second wavelength range is independently selected from the range of 400 nm to 700 nm; wherein the center wavelength of the first wavelength range and the center wavelength of the second wavelength range are different from each other. According to certain embodiments, each of the first wavelength range or a center wavelength of the first wavelength range and the second wavelength range or a center wavelength of the second wavelength range is independently selected from the range of 500 nm to 700 nm; wherein the center wavelength of the first wavelength range and the center wavelength of the second wavelength range are different from each other. According to certain embodiments, the first wavelength range or a center wavelength of the first wavelength range is selected from the range of 500 nm to 600 nm and wherein the second wavelength range or a center wavelength of the second wavelength range is selected from the range of 550 nm and 700 nm; wherein the center wavelength of the first wavelength range and the center wavelength of the second wavelength range are different from each other. According to certain embodiments, the first wavelength range or a center wavelength of the first wavelength range is selected from the range of 520 nm to 600 nm and wherein the second wavelength range or a center wavelength of the second wavelength range is selected from the range of 550 nm and 660 nm; wherein the center wavelength of the first wavelength range and the center wavelength of the second wavelength range are different from each other. Each of the window functions can independently be any window function known or not yet known in the art. According to certain embodiments, each of the first and the second window function is independently a Kaiser window function, a Gaussian window a function, a square or rectangular window function, or a combination of these. According to certain embodiments, the first window function corresponds to a first wavelength range, the first wavelength range being characterized by a peak in optical absorption of the blood or the one or more blood-features; wherein the second window function corresponds to a second wavelength range, the second wavelength range being characterized by a peak in optical scattering of the blood or the one or more blood-features.

According to any embodiments, the optical attenuation of the blood or the one or more blood-features may correspond to absorption, scattering, or both absorption and scattering, of the blood or the one or more blood-features. According to certain embodiments, the SC-OCT characteristic provides an estimate of a slope with respect to wavelength of the optical attenuation of the blood or the one or more blood-features in the target. According to certain embodiments, the method comprises identifying the blood or the one or more blood-features in the target based on an increase in an optical scattering or a decrease in an optical absorption with respect to wavelength of the blood or the one or more blood-features in the target between a center or portion of the first wavelength range, or the first sampling window, and a center or portion of the second wavelength range, or the second sampling window. According to certain embodiments, the method comprises identifying the blood or the one or more blood-features in the target based on a slope of an optical scattering being positive or a slope of an optical absorption being negative with respect to wavelength of the blood or the one or more blood-features in the target between a center or portion of the first wavelength range, or first sampling window, and a center or portion of the second wavelength range, or second sampling window. According to certain embodiments, the method comprises differentiating the blood or the one or more blood-features from one or more non-blood-features in the target based on a difference in a slope of the optical attenuation with respect to wavelength corresponding to the blood or the one or more blood-features from a slope of optical attenuation with respect to wavelength corresponding to the one or more non-blood-features between a center or portion of the first wavelength range, or first sampling window, and a center or portion of the second wavelength range, or second sampling window. According to certain embodiments, the method comprises identifying the blood or the one or more blood-features in the target based on an increase in an optical scattering or a decrease in an optical absorption with respect to wavelength of the blood or the one or more blood-features in the target from a center or portion of the first wavelength range, or the first sampling window, to a center or portion of the second wavelength range, or the second sampling window. According to certain embodiments, the method comprises identifying the blood or the one or more blood-features in the target based on a slope of an optical scattering being positive or a slope of an optical absorption being negative with respect to wavelength of the blood or the one or more blood-features in the target from a center or portion of the first wavelength range, or first sampling window, to a center or portion of the second wavelength range, or second sampling window. According to certain embodiments, the method comprises differentiating the blood or the one or more blood-features from one or more non-blood-features in the target based on a difference in a slope of the optical attenuation with respect to wavelength corresponding to the blood or the one or more blood-features from a slope of optical attenuation with respect to wavelength corresponding to the one or more non-blood-features from a center or portion of the first wavelength range, or first sampling window, to a center or portion of the second wavelength range, or second sampling window. According to certain embodiments, the difference is a difference in absolute value and/or a difference in sign. A difference in sign refers to positive versus negative, or vice versa. According to certain embodiments, the step of identifying or differentiating comprising identifying one or more features of the target characterized by a scattering or backscattering coefficient being proportional to $k^{(4-D)}$, where k is a wavenumber, and D is selected from the range of 1.5±0.2 to 4±0.4. According to certain embodiments, the step of identifying or differentiating comprising identifying one or more features of the target characterized by a scattering or backscattering coefficient being proportional to $k^{(4-D)}$, where k is a wavenumber, and D is (i) substantially less than 4±0.2, (ii) selected from the range of 1.5±0.2 to 4±0.4, (iii) substantially less than 1.5±0.2, and/or (iv) substantially greater than 4±0.2. For example, a D of substantially less than 1.5±0.2 may correspond to lymphatic or fat; a D selected from the range of 1.5±0.2 to 4±0.4 may correspond to healthy tissue; a D substantially greater than 4±0.2 may correspond to blood.

According to certain embodiments, performing OCT scanning comprises performing a plurality of OCT scans (a plurality of A-scans) on a plurality of locations on the target; and wherein each scan (an A-scan) of the plurality of A-scans comprises illuminating a location of the plurality of scanned locations on the target via the sample optical path. According to certain embodiments, each location of the plurality of scanned locations substantially corresponds to only a single A-scan. According to certain embodiments, the step of processing the interference data corresponds to a single A-scan and wherein the step of processing the interference data is repeated for each A-scan of the plurality of A-scans. According to certain embodiments, the step of generating the SC-OCT image comprises combining data corresponding to a plurality of SC-OCT characteristics, each of the plurality of SC-OCT characteristics independently corresponding to an A-scan of the plurality of A-scans. According to certain embodiments, the interference data corresponds to a single A-scan of the plurality of A-scans. According to certain embodiments, the step of performing OCT scanning is performed in a single measurement, the single measurement comprising the plurality of A-scans. According to any embodiment, the plurality of SC-OCT characteristics may be a plurality of SC-OCT ratios and/or a plurality of SC-OCT differences.

According to certain embodiments, the SC-OCT image of the target comprises one or more hemostatic vessels, substantially stationary blood, occluded vessels, blood outside of a wall of a vessel, hemorrhaged blood, or any combination of these.

According to certain embodiments, each A-scan comprises illuminating a location of the plurality of scanned locations on the target for an exposure time selected from the range of 0 seconds to 100 µseconds. According to certain embodiments, the plurality of A-scans are acquired at a scan rate of at least 10,000 A-scans/second, optionally at least 100,000 A-scans/second, optionally at least 1,000,000 A-scans/second, or optionally selected from the range of 10,000 A-scans/second and 10,000,000 A-scans/second, or any scan rate or range of scan-rates therebetween inclusively. The achievable scan-rates, using the methods and systems disclosed herein, may increase as art-known techniques and technologies, such as optical components and data processors, improve over time.

According to certain embodiments, at least one of a resolution and a contrast of the generated SC-OCT image is substantially independent of a standard procedural motion of the target occurring during the step of performing OCT scanning. According to certain embodiments, the method is capable of generating the SC-OCT image having a contrast-to-noise ratio of substantially equal to or greater than 4 between the blood or the one or more blood-features and one or more non-blood-features. Contrast between the blood or the one or more blood-features and one or more non-blood-features may correspond to: [(a characteristic of signal corresponding to the blood or one or more blood features)−(a characteristic of signal corresponding to the one or more non-blood-features)]/(a standard deviation of the characteristic of signal corresponding to the one or more non-blood-features). A characteristic of signal is, for example, an intensity, an average intensity, a median intensity, or an integrated intensity. For example, a contrast between blood and tissue may be at least 30, optionally at least 70, optionally at least 77.5. For example, a contrast between blood and lymph may be at least 4, optionally at least 4.5, optionally at least 10, or optionally at least 20. According to certain embodiments, the method is characterized by a sensitivity selected from the range of 92 dB to 82 dB, optionally selected from the range of 50 dB to 100 dB, or any range therebetween inclusively. According to certain embodiments, the method, or data or SC-OCT image generated thereby, is characterized by each of an axial resolution and a lateral resolution independently being selected from the range of 1 µm to 15 µm, or optionally selected from the range of 100 nm to 20 µm. According to certain embodiments, the SC-OCT image or an inverse of each of the first Fourier transform and second Fourier transform is independently characterized by each of an axial resolution and a lateral resolution independently being selected from the range of 1 µm to 15 µm, or optionally selected from the range of 100 nm to 20 µm.

According to certain embodiments, the method is characterized as a frequency-domain OCT technique, a spectral domain OCT technique, a swept-source OCT, a full field OCT, or any combination of these.

According to certain embodiments, the source light is a low coherence light or light from a swept light source. According to certain embodiments, the plurality of wavelengths of the source light are substantially within the range selected from 500 nm to 700 nm or 500 nm to 850 nm.

According to certain embodiments, the OCT scanning is performed using a flexible probe, and wherein at least a portion of each of the reference optical path and the sample optical path is within the flexible probe. According to certain embodiments, a length of the reference optical path within the flexible probe is substantially equivalent to a length of the sample optical path within the flexible probe. According to certain embodiments, performing the OCT scanning comprises splitting the source light into the reference optical path and the optical sample path using a mechanical occlusion beam splitter. According to certain embodiments, light in the sample optical path and in the reference optical path interacts with at least two achromatic doublet lenses.

According to certain embodiments, the method comprises determining a concentration of a molecular marker in a bodily fluid in the imaged target. According to certain embodiments, the method comprises quantifying a flow of a bodily fluid in the imaged target. According to certain embodiments, the method comprises performing angiography of the target. According to certain embodiments, the method comprises performing endoscopy. According to certain embodiments, the method comprises determining a concentration of one or more molecular markers in the blood using light comprising wavelengths selected from the range of 700 m to 850 nm. According to certain embodiments, the method comprises performing dual band imaging using light comprising wavelengths selected from the range of 700 m to 850 nm.

According to certain embodiments, the method comprises determining an edge and removing the edge in data corresponding at least one of the first Fourier transform and the second Fourier transform. According to certain embodiments, the method comprises determining an air layer in data corresponding at least one of the first Fourier transform and the second Fourier transform and removing the air layer in the data corresponding at least one of the first Fourier transform and the second Fourier transform.

In an aspect, an optical coherence tomography system for imaging a target is configured to: perform optical coherence tomography (OCT) scanning on the target with one or more beams of source light, the one or more beams of source light comprising a plurality of wavelengths; wherein to perform OCT scanning the system is configured to: provide the source light to a reference optical path and to a sample optical path, such that the target is illuminated by the source light via the sample optical path; and record interference data corresponding to an interaction of a light from the reference optical path and a light from the sample optical path; process the interference data, and identify blood or one or more blood-features in the target based on an optical attenuation of light in or associated with the sample optical path by the blood or the one or more blood-features. According to certain embodiments, the system is further configured to differentiate the blood or the one or more blood-features from one or more non-blood-features in the target.

According to certain embodiments, to process the interference data the system is configured to: determine a first Fourier transform and a second Fourier transform from the interference data; and determine a spectral contrast OCT (SC-OCT) characteristic based on the second Fourier transform and the Fourier transform. According to certain embodiments, the system is further configured to generate a spectral contrast OCT (SC-OCT) image of the target using the SC-OCT characteristic.

According to certain embodiments, the system comprises a mechanical occlusion beam splitter for splitting the source light into the reference path and the sample path. According to certain embodiments, light in the sample optical path and in the reference optical path interacts with at least two achromatic doublet lenses, optionally at the distal end of the probe. According to certain embodiments, the at least two achromatic doublet lenses collimate and focus light from each of the sample optical path and the reference optical path. According to certain embodiments, the system comprises a flexible probe having a distal end proximate to the target during OCT scanning; wherein at least a portion of each of the reference path and the sample path is within the flexible probe. According to certain embodiments, a length of the reference path within the flexible probe is substantially equivalent to a length of the sample path within the flexible probe. According to certain embodiments, the flexible probe comprises an optical fiber. According to certain embodiments, the flexible probe has a cross-sectional physical dimension selected from the range of 700 µm to 15 mm, optionally selected from the range of 200 µm to 50 mm. Optionally, the physical dimensions, such as a cross-sectional diameter, of the probe is such that the probe may be used for intravascular imaging and/or endoscopy and/or such that the probe is compatible with tethered capsule upper GI imaging. According to certain embodiments, the flexible probe is capable of being used to perform endoscopy. According to certain embodiments, the reference optical path comprises a reflecting mirror or a reflecting fiber at the distal end. According to certain embodiments, the flexible probe comprises an optically transparent sheath or window to allow for light in the sample optical path to illuminate the target via the optically transparent sheath or window. The optically transparent sheath or window may be at least a portion of an outer surface of the probe at the distal of the probe. Optionally, an outer surface of the probe at the distal of the probe may be a sheath, a portion of which is substantially optically transparent (such as transmission of greater than or equal to 60%, optionally greater than or equal to 80%, optionally greater than or equal to 90%) with respect to a center wavelength of each of the first and the second sampling windows. According to certain embodiments, light associated with the sample optical path exits (in order to illuminate the target) the flexible probe (in order to illuminate the target) via the optically transparent sheath or window. The optically transparent sheath or window may be substantially transparent (such as transmission of greater than or equal to 60%, optionally greater than or equal to 80%, optionally greater than or equal to 90%) with respect to a center wavelength of each of the first and the second sampling windows. According to certain embodiments, the flexible probe comprises a reflective surface configured to direct light associated with the sample optical path toward and through the optically transparent sheath or window. The reflective surface may be a portion of, a coating on, or otherwise associated with the mechanical occlusion beam splitter in the probe. The reflective surface, or any portion thereof that interacts with light in the sample optical path, is optionally positioned at an angle selected from the range of 10 to 80, optionally 30 to 70, optionally 35 to 50, or optionally substantially equal to 41 degrees with respect to (i) an axis of the sample optical path immediately prior to light thereof interacting with the reflective surface, or (ii) with respect to a longitudinal axis of the probe at the distal end. According to certain embodiments, the flexible probe comprises a mechanical occlusion beam splitter, at least two achromatic doublet lenses, and at least a portion of each of the sample optical path and the reference optical path at the distal end of the flexible probe. According to certain embodiments, the system comprises at least one of a SM600 single mode fiber and one or more antireflective-coated C-lenses.

According to certain embodiments, the system being configured to perform dual band imaging. According to certain embodiments, the plurality of wavelengths include wavelengths selected from the range of 500 nm to 700 nm and from the range of 700 nm to 850 nm. The distal end of a probe refers to the end or end region that is proximate to the target during OCT scanning and farther from the source light relative to other regions of the probe. The terms "distal end" and "distal end region" may be used interchangeably. For example, the distal end may include a region corresponding to the distal-most 100 cm, 50 cm, 20 cm, 10 cm, 5 cm, or optionally 1 cm of the probe along a longitudinal direction or axis of the probe. For example, the distal end may include a region corresponding to the distal-most 50%, 40%, 30%, 20%, 10%, optionally 5% of the probe along a longitudinal direction or axis of the probe. The distal end, or distal end region, generally corresponds to the region of the probe that is near or proximate to the scanned or imaged area of the target, compared to other regions of the probe or system having the probe. For example, an end of the probe nearest to a source of the source light (e.g., a lamp, laser, etc.) is a proximal end of the probe, where the proximal end of the probe is opposite of the distal end of the probe along a longitudinal direction or axis of the probe. The longitudinal axis can correspond to a length-wise axis (such as along the length of an optical fiber).

In an aspect, a probe for performing endoscopy of a target using optical coherence tomography (OCT) scanning of the target, the probe comprising: a reference optical path and a sample optical path; wherein the OCT scanning is performed using one or more beams of source light; and wherein each of the reference optical path and the sample optical path comprises the source light, such that the target is illuminated by the source light via the sample optical path; and a distal end, the distal being configured to be proximate to the target; wherein at least a portion of each of the reference optical path and the sample optical path is within the distal end of the probe; wherein the probe is flexible. According to certain embodiments, a length of the reference path within the probe is substantially equivalent to a length of the sample path within the probe. According to certain embodiments, the probe comprises a mechanical occlusion beam splitter for splitting the source light into the reference path and the sample path. The mechanical occlusion beam splitter is optionally at the distal end of the probe. According to certain embodiments, the probe comprises an optical fiber. According to certain embodiments, the distal end of the probe has a cross-sectional dimension selected from the range of 700 µm to 15 mm, optionally selected from the range of 200 µm to 50 mm. Optionally, the physical dimension, such as a cross-sectional diameter, of the probe or distal end thereof is such that the probe may be used for intravascular imaging and/or endoscopy and/or such that the probe is compatible with tethered capsule upper GI imaging. According to certain embodiments, the reference optical path comprises a reflecting mirror or a reflecting fiber at the distal end. According to certain embodiments, light in the sample optical path and in the reference optical path interacts with at least two achromatic doublet lenses. According to certain embodiments, the fiber probe comprises at least one achromatic doublet lens for at least one of collimating and focusing light associated with each of the sample path and the reference path. According to certain embodiments, the flexible probe comprises an optically transparent sheath or window to allow for light in the sample optical path to illuminate the target via the optically transparent sheath or window. The optically transparent sheath or window may be at least a portion of an outer surface of the probe at the distal of the probe. Optionally, an outer surface of the probe at the distal of the probe may be a sheath, a portion of which is substantially optically transparent (such as transmission of greater than or equal to 60%, optionally greater than or equal to 80%, optionally greater than or equal to 90%) with respect to a center wavelength of each of the first and the second sampling windows. According to certain embodiments, light associated with the sample optical path exits (in order to illuminate the target) the flexible probe (in order to illuminate the target) via the optically transparent sheath or window. The optically transparent sheath or window may be substantially transparent (such as transmission of greater than or equal to 60%, optionally greater than or equal to 80%, optionally greater than or equal to 90%) with respect to a center wavelength of each of the first and the second sampling windows. According to certain embodiments, the flexible probe comprises a reflective surface configured to direct light associated with the sample optical path toward and through the optically transparent sheath or window. The reflective surface may be a portion of, a coating on, or otherwise associated with the mechanical occlusion beam splitter in the probe. The reflective surface, or any portion thereof that interacts with light in the sample optical path, is optionally positioned at an angle selected from the range of 10 to 80, optionally 30 to 70, optionally 35 to 50, or optionally substantially equal to 41 degrees with respect to (i) an axis of the sample optical path immediately prior to light thereof interacting with the reflective surface, or (ii) with respect to a longitudinal axis of the probe at the distal end. According to certain embodiments, the probe comprising the mechanical occlusion beam splitter, the at least two achromatic doublet lenses, and at least a portion of each of the sample optical path and the reference optical path at the distal end of the probe. According to certain embodiments, the flexible probe is characterized by a bending angle substantially equal to or substantially less than 210 degrees with a bending radius substantially equal to or substantially less than 17.6 mm. Optionally, the flexible probe, or a substantial portion thereof, is characterized by a bending radius of substantially equal to or substantially less than 200 mm, substantially equal to or substantially less than 100 mm, substantially equal to or substantially less than 75 mm, substantially equal to or substantially less than 50 mm, substantially equal to or substantially less than 20 mm, substantially equal to or substantially less than 17.6 mm, substantially equal to or substantially less than 15 mm, or substantially equal to or substantially less than 10 mm.

In an aspect, a method for imaging a target comprises steps of: performing optical coherence tomography (OCT) scanning on the target with one or more beams of source light, the one or more beams of source light comprising a plurality of wavelengths; wherein performing OCT scanning comprises: providing the source light to a reference optical path and to a sample optical path, wherein providing the source light to a sample optical path comprises illuminating the target with the source light; and recording interference data corresponding to an interaction of a light from the reference optical path and a light from the sample optical path; processing the interference data, the step of processing comprising: determining at least a first short time Fourier transform (STFT) corresponding to a first wavelength range comprising of wavelengths selected from the range of 520 to 580 nm; and generating an image of the target using an inverse of the first STFT. According to certain embodiments, the first wavelength range consists of wavelengths selected from the range of 400 nm to 850 nm, optionally 500 nm to 600 nm, or optionally 520 to 580 nm. According to certain embodiments, the first wavelength range is characterized by a center wavelength selected from the range of 500 nm to 600 nm, or optionally 520 to 580 nm.

In an aspect, a method for imaging a target comprises steps of: performing optical coherence tomography (OCT) scanning on the target with one or more beams of source light, the one or more beams of source light comprising a plurality of wavelengths; wherein performing OCT scanning comprises: providing the source light to a reference optical path and to a sample optical path, wherein providing the source light to a sample optical path comprises illuminating the target with the source light; and recording interference data corresponding to an interaction of a light from the reference optical path and a light from the sample optical path; processing the interference data, the step of processing comprising: determining a first short time Fourier transform (STFT) and a second STFT from the interference data; and determining a spectral contrast OCT (SC-OCT) ratio of the second STFT to the first STFT; and generating a spectral contrast OCT (SC-OCT) image of the target using the SC-OCT ratio.

Also provided herein are methods for imagining a target having any one or any combination of embodiments of methods, systems, and probes disclosed herein. Also provided herein are systems and probes for imaging a target having any one or any combination of embodiments of methods, systems, and probes disclosed herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

The novel features of methods and systems of this disclosure are set forth with particularity in the appended claims. A better understanding of the features and advantages of this disclosure will be obtained by reference to the following detailed description that sets forth illustrative examples, in which the principles of the methods and systems of this disclosure are utilized, and the accompanying drawings.

The following detailed description of certain examples of the present invention will be better understood when read in conjunction with the appended drawings. For the purpose of illustrating the invention, certain examples are shown in the drawings. It should be understood, however, that the present invention is not limited to the arrangements and instrumentality shown in the attached drawings.

FIG. 1A shows a simplified schematic of an OCT system for imaging a target, according to certain embodiments. FIGS. 1B-1E show example in vivo human imaging of labial mucosa (lower lip) from a healthy volunteer. FIG. 1B shows 557 nm inverse and 620 nm inverse B-scans with their corresponding STFT windows, as well as a SC-OCTA B-scan showing contrast shadows from each vessel, with a scale bar of 200 µm. As shown in the example of FIG. 1B, spectral contrast may be a ratio of spectrum 557 nm and 620 nm. FIG. 1C depicts a comparison of angiography en face projections of superficial capillary loops from traditional motion contrast OCTA (64-111 µm), 557 nm inverse (55.6-140 µm), and SC-OCTA (83-209 µm) with their corresponding line profile intensities. Depth ranges are chosen to maximize contrast of en face projections for different techniques with a scale bar of 200 µm, for example. FIG. 1D shows a 3D rendering of 557 nm inverse with a scan area of 3.15×2.94 mm. FIG. 1E illustrates a depth-encoded vessel map of a same field of view (FOV) as FIG. 1D with saturation and value from SC-OCTA and hue from depth of vessel in 557 nm inverse with scale bars of 300 µm. FIGS. 1D-1E highlight a white arrow showing a salivary duct which is correctly not identified by SC-OCTA in FIG. 1E.

FIG. 2A shows an imaging serosal surface of sacrificed mouse colon tissue with a 3D rendering of 557 nm inverse, scan area of 2.9×2.36 mm, en face projection (70-168 µm)SC-OCTA, and scale bar of 250 µm. FIGS. 2B-2D depict example imaging of sacrificed mouse anterior abdominal wall. FIG. 2B shows a B-scan comparison of 557 nm inverse, SC-OCTA, and Depth Integrated SC-OCTA showing how blood is only highlighted using spectral contrast. The far left and far right arrows point to blood vessels and the middle arrow points to lymphatic vessel. Scale Bar: 250 µm. FIG. 2C depicts a 3D rendering of Depth Integrated SC-OCTA showing blood vessels with a scan area of 2.52× 3.78 mm. FIG. 2D provides a 3D rendering of 557 nm inverse with blow up 3D rendering and B-scan cross sections of lymphatic valves, showing a tricuspid valvular structure. FIG. 2D includes a bounding box for LV1: 336× 112×105 µm, a bounding box for LV2: 256×141×130 µm, and scale bars of 30 µm. The dotted line in FIGS. 2C-2D show a cross section location of FIG. 2B.

FIG. 3A shows a 3D rendering of sacrificed mouse omentum. FIG. 3A depicts a depth integrated SC-OCTA image showing blood vessels and 557 nm inverse showing adipocytes and lymphatics with a scanning area of 2.52×3.78 mm. FIG. 3B shows a side view peel-away of FIG. 3A illustrating depth integrated SC-OCTA, 557 nm Inverse and full spectrum 505-695 nm OCT intensity with a bounding box of 2.52×3.78×0.7 mm. FIG. 3C depicts plots of normalized median backscattering (pb) spectra from fat, lymphatic, blood vessels, and tissue measured by visible OCT.

FIG. 10A. SC-OCTA en face projection (Depth: 70-209 µm) of capillary loops in labial mucosa of field of view (FOV) shown in FIGS. 1D-1E. Capillary loop density for area outside of salivary duct (white circle) was calculated to be 14.65 loops/mm$^2$ which falls within reasonable physiological range according to a previous study[10]. Scale bar: 200 µm. FIG. 10B. Line Profile for the capillary loop shown in the box in the upper right corner of FIG. 10A with FWHM for each peak across the loop. Scale bar: 20 µm. FIG. 10C. To more accurately measure vessel diameter a beam expander was placed in the sample and reference arm (to account for dispersion) to increase the effective numerical aperture (NA) of the sample focusing objective resulting in a new lateral resolution of 2.1 µm. A 1.76 mm×1.76 mm scan was taken with a sampling density of 2 µm. A capillary loop was then imaged over a new FOV with the higher effective numerical aperture in the lip. Please note this is not the same capillary loop shown in FIG. 10B. Scale Bar: 20 µm. FWHM was calculated by fitting a Gaussian to each peak across the loop.

FIG. 11D. SC-OCTA and OCTA en face projection with flow and flow with vibrations. FIG. 11E. SNR analysis of en face projections in FIG. 11D. SC-OCTA (No vibrations: 21.04±1.51; With vibrations: 9.34±0.65). OCTA (No vibrations: 5.904±1.57; With vibrations: 0.18±0.2). ** (p<0.01) for two sample t-test. FIG. 11F. Mask used for calculating SNR. Gray vertical bars at the edges represent background. White vertical bar in center is vessel. Thin horizontal lines delineate the 10 areas for determining standard deviation of SNR. All scale bars: 200 µm.

FIG. 14A. Comparison of SC-OCTA and OCTA en face projections and B-scans (from the dotted line on the en face projection). The power of SC-OCTA can be visualized in the case of hemostasis, as OCTA has difficulty sensing even large vessels. The white arrow points to the same vessel detected by SC-OCTA (56-280 μm) and OCTA (28-336 μm). The depths were chosen to maximize the contrast of each method. Scale bar: 200 μm. FIG. 14B. Large field of view from SC-OCTA with saturation and value from SC-OCTA and hue from the depth of vessel in the inverse 557 nm. Scale bar: 250 μm.

FIGS. 15A-15G. Single-scan vessel imaging of blood and lymphatic vessels of a sacrificed mouse anterior abdominal wall (FIGS. 15A-15O) and heart surface (FIGS. 15E-15F). FIG. 15A. B-scan comparison of inverse 557 nm, SC-OCTA, and depth-integrated SC-OCTA showing how blood is only highlighted using spectral contrast. Blood vessels (far left and far right arrows), lymphatic vessel (the middle left arrow), and adipocytes (the middle right arrow). Scale bar: 250 μm. FIG. 15B. Side view peel-away showing depth-integrated SC-OCTA, which allowed blood vessels to be visualized, inverse 557 nm with vessels removed showing adipose/lymphatic tissue and full-505-695 nm OCT intensity showing highly scattering tissue. Bounding box: 2.52×3.78×0.7 mm. FIG. 15C. 3D rendering. Depth-integrated SC-OCTA showing blood vessels and inverse 557 nm showing adipocytes (asterisk) and lymphatics (arrows). The dotted line shows the cross-section location of FIG. 15A. Bounding box: 2.52×3.78×0.7 mm. FIG. 15D. 3D rendering and B-scan cross-sections of lymphatic valve 1 (LV1) and lymphatic valve 2 (LV2) from the little rectangular boxes in FIG. 15C, showing a tricuspid valvular structure. Bounding box for LV1: 336×112×105 μm. Bounding box for LV2: 256×141×130 μm. Scale bars: 30 μm. FIG. 15E. 3D rendering. Depth-integrated SC-OCTA showing blood vessels and inverse 557 nm showing lymphatics. Bounding box: 2.02× 3.36×1 mm. FIG. 15F. Top view of FIG. 15E showing a blood vessel branch (bottom arrow) with lymphatic vessels (top arrow) and FIG. 15G corresponding immunofluorescence microscopy localizing podoplanin to distinguish blood vessels from lymphatic vessels. FIGS. 15F-15G. Scale bars: 50 μm. The asterisk in FIG. 15E corresponds to the asterisk in FIG. 15F.

FIG. 19A. Attachment of the laser etched cover slip onto the 41 degree polished ferrule before e-beam coating with aluminum. FIG. 19B. Close up of ~50 micron diameter laser etched occlusion on the cover slip.

FIG. 22A shows simulated SC-OCTA B-scan image for a 20 μm diameter vessel placed at the white circle. Scale bars: 20 μm. FIG. 22B shows line profiles of simulated (solid) and experimental (dotted) en face SC-OCTA images integrated over 140 μm in depth. The experimental line profiles come from the SC-OCTA en face projections shown in FIG. 1E and FIG. 10A.

FIG. 23A shows roll-off impulse response for the total system 505-695 nm bandwidth. Roll-off sensitivity ~–10 dB/mm. Air axial resolution (1.53 μm) and sensitivity (91.61 dB) measured from the first peak. FIG. 23B shows roll-off impulse response for the 557 nm centered Kaiser sampling window. Roll-off sensitivity ~–14 dB/mm. Air axial resolution (3.80 μm) and sensitivity (86.05 dB) measured from the first peak. FIG. 23C shows roll-off impulse response for the 620 nm centered Kaiser sampling window. Roll-off sensitivity ~–11 dB/mm. Air axial resolution (4.72 μm) and sensitivity (81.11 dB) measured from the first peak. FIG. 23D shows SC-OCTA signal standard deviation (ascending line) and total system sensitivity (descending line) measured in FIG. 23A. The standard deviation of SC-OCTA signal was processed according to equation (3) for each mirror position over 500 A-lines. The aqueous 80 nm bead calibration was not necessary for estimation of standard deviation of SC-OCTA, and no median filters were used. The correlation between increasing system sensitivity and decreasing SC-OCTA standard deviation can be seen. The slight increase in standard deviation of SC-OCTA near the zero depth can be a result of direct current noise which can be reduced or minimized through high pass filtering the interferogram.

FIG. 25A is a photograph corresponding to in vivo human imaging of labial mucosa. FIG. 25B is a photograph corresponding to imaging of freshly sacrificed mouse tissue.

STATEMENTS REGARDING CHEMICAL COMPOUNDS AND NOMENCLATURE

Figure 1A:
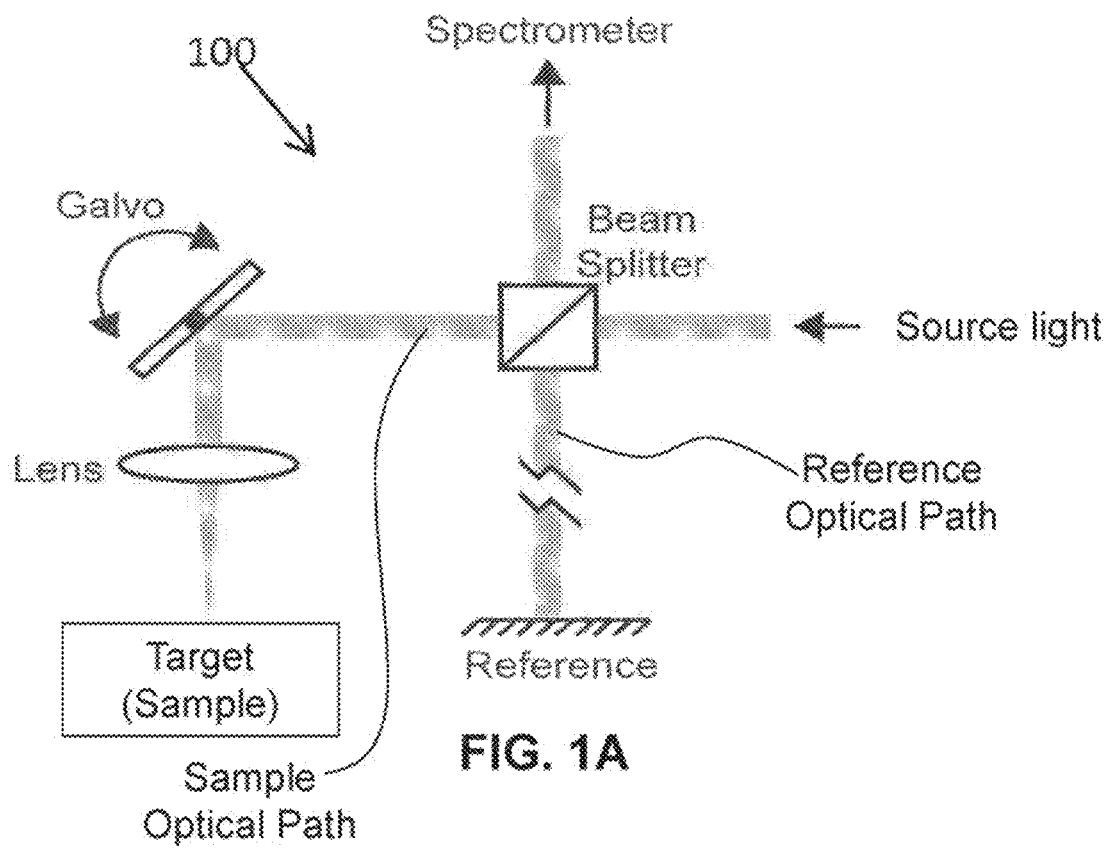
FIGS. 1A-1E.

In general, the terms and phrases used herein have their art-recognized meaning, which can be found by reference to standard texts, journal references and contexts known to those skilled in the art. The following definitions are provided to clarify their specific use in the context of the invention. Additional definitions and descriptions may be found throughout this application.

The term "sample optical path" refers to a path followed by a light, wherein the path includes light being directed to a target and interacting with the target. A light interacting with the target can include the light being optically attenuated by the target, or otherwise optically attenuated via its interaction with the target. Optionally, the sample optical path also includes a path followed by light that has interacted with the target ("attenuated light"), such as light after optical attenuation by the target, between the target and one or more detectors, or other detection mechanism, configured to detect the attenuated light and/or an interference caused by an interference of the attenuated light and another light, such as a reference light, or light associated with the reference optical path. Optionally, at least a portion of the sample optical path used to direct a light to a target can be used to also collect or receive a light after interaction with the target (attenuated light). For example, one or more optical components (lens, optical fiber, etc.) can both direct a light to a target and direct a light (e.g., the attenuated light) from the target. Optionally, attenuated light received or collected by the sample optical path is light transmitted through the target, or portion thereof, reflected off the target, or portion thereof, scattered by the target, or portion thereof, or any combination of these. The term "reference optical path" refers to a path followed by light, wherein light from the reference optical path is used, or is intended to be used, as a reference, compared to light that has interacted with the target ("attenuated light"), such as light after optical attenuation by the target. The reference optical path does not include directing light to the target. The reference optical path optionally includes one or more mirrors, or reflective elements or surfaces thereof, configured to reflect at least a fraction of light associated with the reference optical path. An interaction, or interference, of light associated with the reference optical path and attenuated light associated with the sample optical path form an interference light, interference signal, and/or interference pattern which may be recorded as interference data, such as in the form of an interferogram. At least a portion of the reference optical path and at least a portion of the sample optical path may be congruent or coincident. For example, the portion of the reference optical path and the portion of the sample optical path between a source of light (e.g., laser, lamp, etc.) and a beam splitter, such as the last beam splitter after the source and before the target along either of the paths, may be substantially congruent, coincident, or equivalent. A beam splitter may be used to split one or more beams of light into a plurality of directions or optical paths. For example, a reference optical path and a sample optical path may diverge at/after a beam splitter, such that the reference optical path includes a reference mirror after the beam splitter and the sample optical path includes directing light to the target after the beam splitter. Optionally, a beam splitter may cause the reference optical path and the sample optical path to converge. The method and systems disclosed herein may comprise a plurality of reference optical paths, a plurality of sample optical paths, a plurality of sources of light, a plurality of beam splitters, and/or a plurality of light beams, for example.

Generally, the term "spectral contrast optical coherence tomography characteristic" "SC-OCT characteristic" refers to a value, variable, or mathematical function or relationship, including any arithmetic operation, between at least two Fourier transforms, where the at least two Fourier transforms corresponds to two different wavelengths or ranges of wavelengths of an interferogram corresponding to an interference of a light from at least one sample optical path and a light from at least one reference optical path. For example, the SC-OCT characteristic may be a ratio (an SC-OCT ratio) or a difference (an SC-OCT difference). As would be recognized to one of ordinary skill in the art, certain mathematical relationships may be expressed in a plurality of equivalent ways or may be approximated in a plurality of ways. As a simple illustrative, a characteristic corresponding to a logarithm of a ratio of 'a' and 'b' (e.g., log a/b) may be expressed as a difference (e.g., log a–log b).

The term "optical attenuation" generally refers to a decrease and/or modification of light, or a beam of light, or one or more characteristics of the light or beam of light (including but not limited to flux, wavelength, spectrum, and any combination of these), optionally decrease and/or modification of light along, within, or otherwise corresponding to an optical path, as a result of interaction of the light with a medium, or a plurality of media. For example, process(es) or interaction(s) contributing to an optical attenuation include, but are not limited to, absorption and/or scattering. The medium, or media, includes, but is not limited to, a target or one or more features of a target, including but not limited to, blood, blood-features, and/or non-blood-features, including, but not limited to, tissue, lymphatic tissue, fat, vessel walls (e.g., vein, artery, etc.), and/or non-blood fluid(s). The term "backscattering" or "backscattered light" may refer to correspond light scattered as a result of interaction with a medium, or media, and collected via a sample optical path. For example, backscattered light may refer to light scattered, and collected, substantially along an axis substantially corresponding to an axis of the sample optical path where light is directed to and interacting with the target (e.g., source light is directed upon the target and then resulting scattered light is generally directed and collected via at least a portion of the path from which the source light came). The term "scattering" or "scattered light" includes "backscattering" or "backscattered light", respectively.

The term "sampling window" refers to a wavelength or range of wavelengths. For example, a sampling window is a wavelength or range of wavelengths representing a segment of spectral data, including interference data, that is analyzed or is intended for analysis. For example, a Fourier transform may be applied to or otherwise correspond to a wavelength range that is the sampling window to which the Fourier transform corresponds. The term "window function" is a mathematical function corresponding to a given wavelength or range of wavelengths (or, a given sampling window) wherein the window function is zero-valued at wavelengths not corresponding to the given wavelength or range of wavelengths (or, the given sampling window). A given window function has a corresponding given sampling window (or, given wavelength or wavelength range). For example, determining a Fourier transform, such as an STFT, may include multiplying interference data by a window function. A window function may be symmetric about the middle of the wavelength range, or sampling window, the middle typically, but not necessarily, being at or near a maximum value of the window function, and typically, but not necessarily, may taper away from the middle. For example, mathematically, when another function or waveform or data-sequence is multiplied by a window function, the product is also zero-valued at wavelengths outside of the given wavelength range (or, the given sampling window), such that the product may be non-zero at wavelengths corresponding to the given wavelength range (or, the given sampling window). For example, a window function may be used to segment, taper, and/or otherwise modify or shape a function, waveform, or data-set. Exemplary window functions include, but are not limited to, rectangular or square window functions, B-spline window functions, other polynomial window functions, sine window functions, cosine-sum window functions, adjustable window functions, hybrid window functions, and other window functions. For example, these window functions include, but are not limited to, Gaussian window functions and Kaiser (or, Kaiser-Bessel) window functions. Kaiser window function may be preferably for certain embodiments.

Certain terms, including certain terminology associated with characterizing data, data processing, and/or mathematical manipulation of data, such as, but not limited to, Fourier transform (FT), short-time Fourier transform (STFT), and an inverse of an FT or STFT, as well as sensitivity, resolution, and contrast, may have their art-known meaning as used herein.

The systems and methods disclosed herein may be used with any art-known elements, features, components, and procedures which are necessary or which may be used in conjunction with and/or in order to achieve, assemble, and/or operate certain disclosed methods and systems. For example, an OCT system may include art-known optical components not explicitly disclosed herein. Descriptions and exemplary techniques associated with these and other terminology is found throughout the application.

Generally, a short-time Fourier transform (STFT) is to a Fourier-related transform corresponding a portion of a signal or data-set. A short-time Fourier transform (STFT), for example, may correspond to a Fourier-related transform used to determine a frequency (e.g., sinusoidal frequency) and phase content of local sections of a signal as it changes over time. Determining an STFT may include dividing or segmenting a longer time signal into shorter segments of equal length and then determining the Fourier transform separately on each shorter segment.

The terms "hemostasis" and "hemostatic" generally refer to a condition wherein blood is substantially stationary or non-flowing. Coagulated blood, for example, may be hemostatic.

The term "contrast," such as when referring to an image, such as an SC-OCT image, may be used to quantify an ability to differentiate certain features, such as blood or a blood-feature, from other or non-blood-features in a data-set, such as an SC-OCT image. For example, contrast corresponds to [(a characteristic of signal corresponding to blood or a blood-feature)−(a characteristic of signal corresponding to one or more non-blood-features)]/(a characteristic of signal corresponding to one or more non-blood-features). For example, contrast corresponds to [(an intensity of data or pixel(s) corresponding to blood or a blood-feature)−(an intensity of data or pixel(s) corresponding to one or more non-blood-features)]/(an intensity of data or pixel(s) corresponding to one or more non-blood-features). For example, contrast corresponds to [(an intensity of data or pixel(s) corresponding to a vasculature, blood, or blood-feature)−(an intensity of data or pixel(s) corresponding to background tissue)]/(an intensity of data or pixel(s) corresponding to background tissue). An intensity can be an intensity, an average intensity, a median intensity, or an integrated intensity. The term "contrast-to-noise ratio" refers to a contrast ratio between a first feature and a second feature with respect to a noise characteristic. A contrast-to-noise ratio can correspond to: [(a characteristic of signal corresponding to the first feature)−(a characteristic of signal corresponding to the second feature)]/(a standard deviation of the characteristic of signal corresponding to the second feature). A characteristic of signal is, for example, an intensity, an average intensity, a median intensity, or an integrated intensity. For example, a contrast between blood and tissue may be at least 30, optionally at least 70, optionally at least 77.5, for a field of view such as the field of view corresponding to FIG. 15C. For example, a contrast between blood and lymph may be at least 4, optionally at least 4.5, optionally at least 10, or optionally at least 20, for a field of view such as the field of view corresponding to FIG. 15C. The contrast between two features may be dependent upon noise in signal corresponding to each of the two features.

The term "biological motion" refers to motion of a target (or portion of the target being scanned). The specific nature, characteristics, or cause of biological motion is typical and particular to the nature of the target and procedure. Exemplary biological motions, or causes thereof, include, but are not limited to, heartbeat, respiration, and/or vertebrae muscle skeletal movement. The term "standard procedural motion" refers to motion that is normal for a given target and procedure (e.g., endoscopy). Standard procedural motion includes biological motion(s). Standard procedural motion may also include, but is not limited to, motion between a probe (e.g., endoscope) and the target (e.g., a tissue surface), and/or non-uniform rotational distortion (NURD). Standard procedural motion or biological motion may be random, periodic, or a combination of these. According to certain embodiments, standard procedural motion or biological motion is characterized by a an amplitude of a random or periodic oscillation or variation less than or equal to 10 cm, optionally less than or equal to 2 cm, optionally less than or equal to 1 cm, optionally less than or equal to 1 mm, or optionally less than or equal to 100 µm.

The term "blood-features" refers to one or more features, characteristics, portions, and/or substituents of blood. For example, blood-features include, but are not limited to, hemoglobin, red blood cells, and/or white blood cells. An exemplary characteristic of blood is absorption, an absorption cross-section, and/or scattering associated with blood. The term "non-blood-features" refers to a feature, characteristic, portion, and/or substituent in, on, or otherwise associated with the target that is not or is not associated with blood or a blood-feature. Exemplary non-blood-features include, but are not limited to, tissue, fat, lymph tissue, blood vessel wall, lymph vessel wall, non-blood fluid, and any combination of these.

Generally, a "target" refers to that which is being imaged using any of the methods or systems disclosed herein. A target may be a portion of a dead or living subject, for example. A subject may be a human or an animal, or any portion thereof, such as an organ or portion thereof, for example. A target may be imaged or scanned by scanning or imaging a plurality of locations (or, portions, regions, etc.) of the target and combining data associated with the scans and/or images of the plurality of locations.

The term "bending radius" corresponds to a minimum radius of curvature of a material, device, object, or other component, such as a substantially one-dimensional device or component, such as a fiber, tube, or cable, without permanently adversely affecting its mechanical and/or optical properties, other otherwise without kinking it, damaging it, or shortening its lifetime. The bending radius may be determined using the inside curvature of the device or component. The smaller the bend radius, the greater is the flexibility of the material, device, object, or component. Optionally, the bend radius is a minimum radius of curvature below which an object should not be bent according to manufacturer instructions, manufacturer recommendations, or other art-recognized limitations.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

I. General Overview

In addition to motion-based OCT contrast enhancement for angiography, spectroscopic visible band OCT imaging enables true-color imaging of biological tissues by resolving distinct spectral absorption features. The abilities to quantify hemoglobin concentration and oxygenation from endogenous contrast and molecular information from exogenous nanoparticle-based contrast agents are promising applications made possible through the development of visible spectroscopic OCT. Thus, development of OCT systems in the visible bandwidth provides measurement of valuable absorption-based information at high spatial resolution.

Certain examples provide a novel and robust system and method to obtain angiography images from a spectral domain OCT (SD-OCT) signal, referred to as Spectral Contrast OCT Angiography (SC-OCTA). As used herein, SC-OCT and SC-OCTA may be used interchangeably. SC-OCTA may refer to a category of illustrative examples (angiography), out of many possible, of using and applying SC-OCT, or generally the methods and systems disclosed herein. Utilizing distinct spectral features of hemoglobin in the visible range, SC-OCTA provides 3D angiography without the need to repeat scanning protocols, eliminating all motion-based artifacts ubiquitous in previously established OCT angiography (OCTA) and allowing for the fastest SD-OCT angiography acquisition speeds to date. Furthermore, this unique method of spectral-based vessel segmentation eliminates the need for blood flow-induced motion for angiography, allowing for the novel ability to image vasculature in hemostatic tissues. This ability enables SC-OCTA to image blood leakage from compromised vasculature to assess hemorrhage, such as in the case of cardiovascular disease, resulting in SC-OCTA being a valuable microvasculature imaging tool.

Traditionally, OCT performs angiography by scanning the same location twice and looking for phase shifts or speckle variations in an image. This can be problematic because small sample movement can eliminate contrast in smaller vessels. This is especially true for OCT endoscopes where there is living moving tissue and a moving endoscope. SC-OCTA determines vessel location based on blood absorption, removing the requirement to scan twice and allowing capillaries to be seen in highly moving samples, creating a valuable tool for OCT endoscope angiography.

II. General Methods for Flow Measurement

Terminology of OCT Methods

The terms "optical coherence tomography" and "OCT," described herein, generally refer to an interferometric technique for imaging samples, in some examples, with micrometer lateral resolution. This non-invasive optical tomographic imaging technique is used in a variety of medical and industrial applications to provide cross-sectional or 3D images of a target.

The terms "functional OCT" and "fOCT," described herein, generally refer to a method of OCT imaging that provides for the acquisition of both structural (3D, tomographic and cross-sectional information) and functional information about a target, as described herein. In some examples, fOCT may refer to "visible-OCT" or "vis-OCT." Vis-OCT generally refers to a type of fOCT that includes use of visible light. In some examples, OCT or fOCT may refer to OCT methods comprising use of near infrared (NIR) light.

As describe herein, fOCT may utilize any method of OCT. Generally, fOCT may be configured with an interferometer, as is the case for many other OCT methods. Light from a light source (for example, a broadband light source) is split (for example, by a beam-splitter) and travels along a sample arm (generally comprising the sample) and a reference arm (generally comprising a mirror). A portion of the light from the sample arm illuminates a target. Light is also reflected from a mirror in the reference arm. (Light from the test arm and the reference arm is recombined, for example, by the beam-splitter.) When the distance travelled by light in the sample arm is within a coherence length of the distance travelled by light in the reference arm, optical interference occurs, which affects the intensity of the recombined light. The intensity of the combined reflected light varies depending on the target properties. Thus, variations for the intensity of the reflectance measured are indications of the physical features or attributes of the target being imaged. Configuration of the system can vary as described further below.

In some examples, the methods and systems of the disclosure may utilize time-domain OCT, where the length of the reference arm can be varied (for example, by moving one or more reference mirrors). The reflectance observed as the reference arm distance changes indicates sample properties at different depths of the sample. In some examples, the length of the sample arm is varied instead of or in addition to the variation of the reference arm length. In some examples, the devices, methods and systems may utilize frequency-domain OCT, where the distance of the reference arm can be fixed, and the reflectance can then be measured at different frequencies. For example, the frequency of light emitted from a light source can be scanned across a range of frequencies or a dispersive element, such as a grating, and a detector array may be used to separate and detect different wavelengths. Fourier analysis can convert the frequency-dependent reflectance properties to distance-dependent reflectance properties, thereby indicating sample properties at different sample depths. In certain examples, OCT can show additional information or data not obtainable from other forms of imaging.

In some examples, the methods and systems of the disclosure may utilize frequency-domain optical coherence tomography, where the reference and sample arms are fixed. Light from a broadband light source comprising a plurality of wavelengths is reflected from the sample and interfered with light reflected by the reference mirror/s. The optical spectrum of the reflected signal can be obtained. For example, the light may be input to a spectrometer or a spectrograph, comprising, for example, a grating and a detector array that detects the intensity of light at different frequencies.

In some examples, the methods and systems of the disclosure may utilize spectral domain optical coherence tomography, whereby spectral information is extracted by distributing different optical frequencies onto a detector stripe (for example, a line-array CCD or CMOS) via a dispersive element. Information of the full depth scan can be acquired within a single exposure.

Fourier analysis may be performed, for example, by a processor, and may convert data corresponding to a plurality of frequencies to that corresponding to a plurality of positions within the sample. Thus, data from a plurality of sample depths can be simultaneously collected without the need for scanning of the reference arm (or sample) arms. Additional details related to frequency domain optical coherence tomography are described in Vakhtin et al., (Vakhtin A B, Kane D J, Wood W R and Peterson K A. "Common-path interferometer for frequency-domain optical coherence tomography," Applied Optics. 42(34), 6953-6958 (2003)) and incorporated by reference herein.

Other methods of performing optical coherence tomography are possible. For example, in some cases of frequency domain optical coherence tomography, the frequency of light emitted from a light source varies in time. Thus, differences in light intensity as a function of time relate to different light frequencies. When a spectrally time-varying light source is used, a detector may detect light intensity as a function of time to obtain optical spectrum of the interference signal. The Fourier transform of the optical spectrum may be employed as described herein. The devices, methods and systems of the disclosure may utilize any method of OCT, including but not limited to spectral domain OCT, Fourier domain OCT, time encoded frequency domain OCT, or swept source OCT, single point OCT, confocal OCT, parallel OCT, or full field OCT as known in the art.

Generally, the term "A-scan" OR "A-line" describes the light reflectivity associated with different sample depths. The term "B-scan" or "B-line" as used herein refers to the use of cross-sectional views of tissues formed by assembly of a plurality of A-scans. In the case of OCT methods of cancer detection, light reflected by cancerous tissue target is converted into electrical signals and can be used to generate both cross-sectional or 3D structural images and metabolic functional information about the target tissue (such as cancerous growth, lesion, or tumor). In the case of ophthalmology, light reflected by eye tissues is converted into electrical signals and can be used to provide data regarding the 3D structure of tissue in the eye and metabolic activity in the retina. In many cases, including but not limited to cancer detection and ophthalmology, A-scans and B-scans can be used, for example, for differentiating normal and abnormal tissue.

For general methods, an A-scan can generally include collecting data at one or more transverse locations in a target, at a plurality of depths in a z-axis direction; a B-scan may include cross-sectional data from a medial border to a lateral border, or (x,y) axis direction. In the case of OCT of a skin cancer lesion for example, an A-scan can generally include data from the outer regions of the epidermis of the lesion to the inner regions comprising vasculature, while B-scans can include cross sectional data from one lesion border to another in the (x,y) plane. In ophthalmic instances, an A-scan can generally include data from the cornea to the retina, and a B-scan can include cross-sectional data from a medial border to a lateral border of the eye and from the cornea to the retina. 3D C-scans may be used to generate one or more 3D images by combining a plurality of B-scans in variety of examples.

In the present disclosure, "target" may indicate any sample, object, or subject suitable for imaging. In some examples, a target may include but is not limited to inanimate material such as metals, alloys, polymers, and minerals as found for industrial applications for OCT and as described herein. In some examples, a target may be animate material, such any suitable living material including but not limited to embryos, seeds, cells, tissues, grafts, blood vessels, organs, or organisms as would be suitable for medical and agricultural applications for OCT as described herein. In some examples, a target may be retinal tissue, etc.

In some cases, axial fluid flow components may refer to physical parameters relating to the movement of one or more particles in the fluid. For example, in blood, one or more blood components, such as blood cells may be imaged by Doppler OCT. Axial fluid components of individual red blood cells in a blood vessel may include but are not limited to the blood vessel diameter, the velocity of the red blood cell and the Doppler angle of the imaging beam of radiation, as described herein.

The methods and systems of the present disclosure may use any light source suitable for OCT, including but not limited to supercontinuum lasers, superluminescent diodes, continuous wave lasers or ultrashort pulsed lasers. The light source may be used to generate one or more low coherence beams of radiation or light to illuminate the target, for example.

The calculation methods described herein may be performed by a software algorithm or computer of the OCT device/system. Generally, OCT scanning data is acquired by the OCT device or system and subsequently analyzed through the calculation methods described herein. The absolute flow rate F of the target can be expressed as any unit of distance divided by a time unit. In some examples, where the target sample is one or more retinal vessels in an eye, the absolute flow rate may be expressed as µl/min. Generally, axial flow components are a combination of absolute flow velocity V, which can be expressed as any suitable units of distance divided by time, (e.g. mm/s), and the perpendicular cross-sectional vessel size S of the vessel, (e.g. $\mu m^2$). In some examples, the absolute flow rate F can be determined by multiplying the absolute flow velocity V by the perpendicular cross-sectional vessel size S of the vessel. Alternatively, F can also be quantified by the detected mean projected velocity $V_m$ and the measured vessel area $S_m$ from Doppler OCT.

A target may include any vessel or structure that can contain a fluid to be imaged including but not limited to tissue, healthy tissue, diseased tissue, retina, tumor, cancer, growth, fibroid, lesion, skin, mucosal lining, organ, graft, blood supply and one or more blood vessels.

In some examples, a fluid may be any material capable of flow, in which there may be particles that may be imaged by OCT or Doppler OCT. Bodily fluid may include but is not limited to whole blood, blood plasma, blood serum, urine, semen, tears, sweat, saliva, lymph fluid, pleural effusion, peritoneal fluid, meningal fluid, amniotic fluid, glandular fluid, spinal fluid, conjunctival fluid, vitreous, aqueous, vaginal fluid, bile, mucus, sputum and cerebrospinal fluid.

In some examples, target function may include but is not limited to metabolic activity, metabolic rate, oxygen consumption, tissue consumption of a biomarker or analyte, pathophysiological alterations, pathological alterations, histological change such as tissue remodeling, abnormal growth of one or more blood vessels, or abnormal tissue growth, necrosis, apoptosis, necrosis, angiogenesis, cell proliferation, neuromodulation, neural activity, wound healing, infection, burns, scarring, radiological damage, hypoxia, oxidative stress and the like.

In some examples, measurements regarding flow rate of fluid such as blood may be used to compute or determine target function. For example, measurements regarding the flow rate of blood may help determine the flow rate of oxygen (via hemoglobin transport) into or out of a particular target or region. The flow of oxygen may be a critical factor in determining metabolic activity, histological change such as tissue remodeling, abnormal growth of one or more blood vessels, or abnormal tissue growth, necrosis, apoptosis, necrosis, angiogenesis. In other examples, the measurements of flow of other analytes or cells in fluids such as cerebrospinal fluid (CSF), may indicate the presence of disease of infection or inflammation of one or more parts of the nervous system.

In some examples, a change in target function may be determined by comparing information from flow measurement of a fluid to a reference. In some examples, a reference many include but is not limited to measurements of from a healthy or normal target, one or more previous measurements, or an average of information from healthy subjects. In some examples, a reference may include flow measurement at different times. In some examples, one or more references may be compared to other references to determine a change in flow measurements.

Example Terminology

The terminology used therein is for the purpose of describing particular examples only and is not intended to be limiting of a device of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a device of this disclosure are described above with reference to example applications for illustration. It should be understood that numerous specific details, relationships, and methods are set forth to provide a full understanding of a device. One having ordinary skill in the relevant art, however, will readily recognize that a device can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another example. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

III. Detailed Description of Certain Examples

While there are several OCT operating bandwidths which can be chosen, a typically favored range for biological imaging is the near infrared (NIR) from approximately 700-900 nm. This is because the short wavelength range provides higher OCT axial resolution when compared to >1000 nm and it falls within the 'optical window'. In the 'optical window', there is minimal absorption from water and hemoglobin allowing for high penetration. While this facilitates NIR OCT systems to penetrate deeply into tissues, it diminishes their sensitivity to blood and tissue (non-vessel containing) spectral features. Blood absorption coefficients are about two orders of magnitude higher in the 400-600 nm range and tissue scattering coefficients are about double compared with the NIR range. This is what allows visible OCT systems to be sensitive to blood oxygenation and achieve higher image contrast.

For most of the visible and NIR spectrum, blood and tissue's spectral slope follow a similar trend of decreased scattering with increasing wavelength. However, this is not the case from 550 to 600 nm where the spectral slope for blood is positive whereas it remains negative for surrounding tissue. Certain examples combine this unique spectral feature with the visible spectrum's high image contrast to rapidly and easily image tissue and blood with clear discrimination to the level of individual capillaries.

SD-OCT obtains depth resolved sample information by taking a Fourier Transform of the interference recorded as a function of wavelength (on a spectrometer) between a reference reflection and light scattered from the sample, as shown in an example apparatus 100 of FIG. 1A.

The OCT data collected from one point-wise scanning location is called an A-line and stitching together A-lines to form a cross-section of the sample is called a B-scan. By only sampling a portion of the spectrum a short time Fourier Transform (STFT) can be carried out which results in a spectrally dependent OCT A-line. Therefore, blood and tissue's opposite spectral slopes can be spatially visualized by looking at the contrast of spectral dependent OCT image intensities from 550 nm to 600 nm. For example, a Kaiser sampling window at 557 nm and 620 nm, with a full width at half max (FWHM) of ~38 nm, provides high spectral contrast between blood and the surrounding tissue.

Figure 1B:
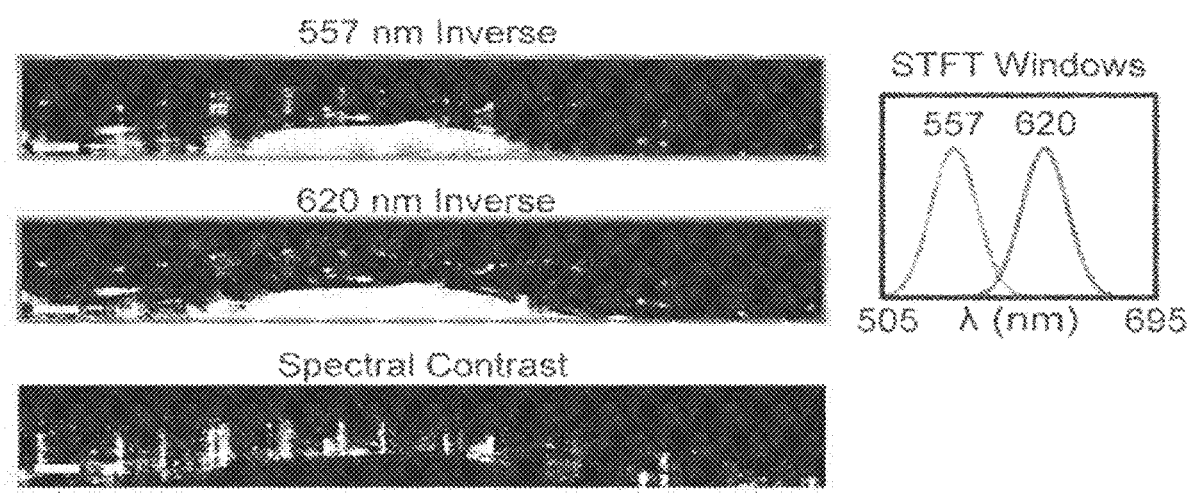
Figure 1C:
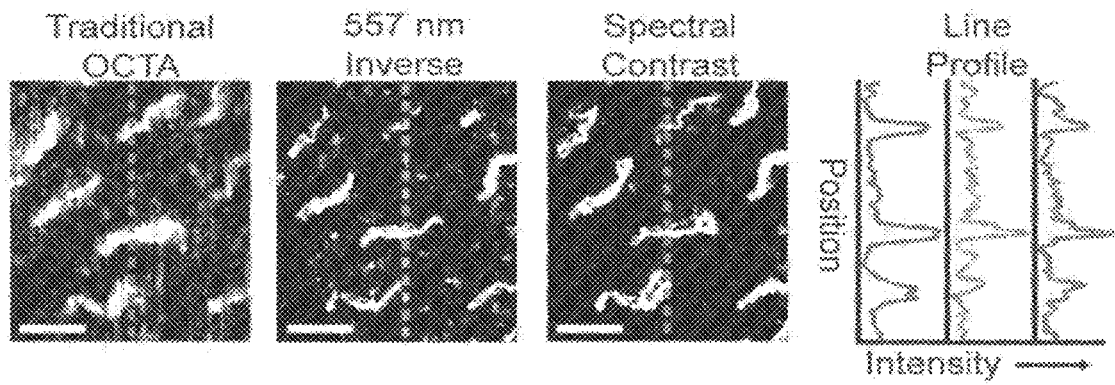
Figure 1D:
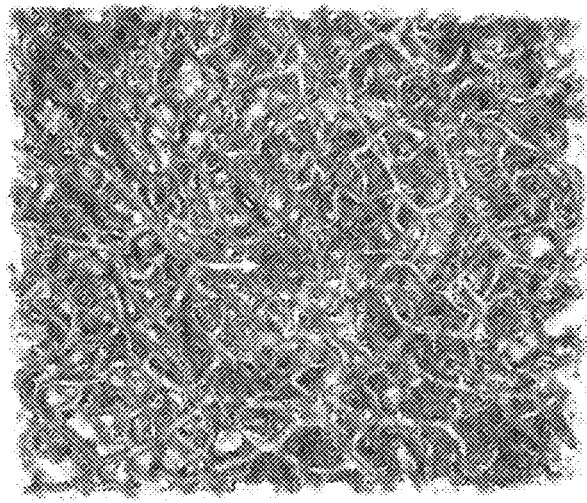
Figure 1E:
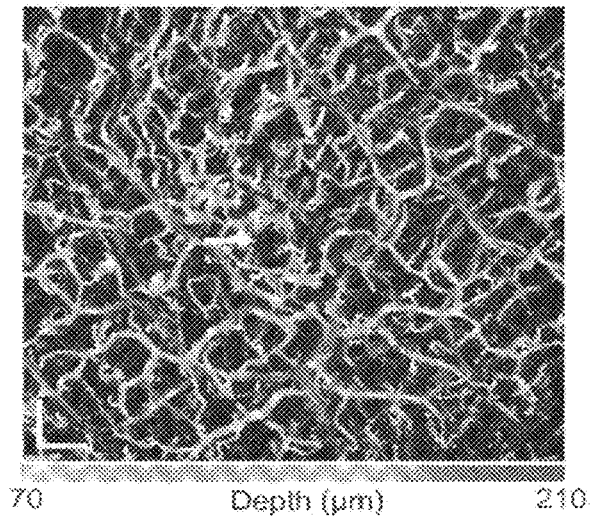

In FIG. 1B, in vivo B-scans of lower human labial mucosa (inner side of lip) can be seen with the inverse OCT image intensities of the two Kaiser windows and their ratio (e.g., 620 nm divided by 557 nm), hereafter referred to as SC-OCTA. In the inverse OCT intensity images, blood vessels can easily be seen due to the high contrast and high absorption provided by the visible range. The spectral contrast image demonstrates how blood vessels are highlighted by a shadow and tissue is ignored. Inverse OCT intensity and SC-OCTA methods work all the way down to the capillary level with only a single scan. To confirm this, inverse OCT intensity and SC-OCTA en face projections can be compared with traditional OCTA phase and amplitude contrast, as can be seen in the example of FIG. 1C. The same eight capillary loops in the labial mucosa are seen in the 557 nm inverse image, SC-OCTA, as well as in the traditional OCT angiography which requires the sample to be scanned at least twice, for example. A detailed large field of view (e.g., 3.15×2.94 mm) of the labial mucosa is shown in FIGS. 1D-1E, demonstrating the ability of SC-OCTA to resolve arteriolar and capillary-level vessels with only a single A-line acquired at each point-scanning location. FIGS. 1D-1E demonstrate how the inverse OCT intensity image does not differentiate low scattering structures from hemoglobin absorption. This is noted by the white arrow showing a salivary duct that is visible in the inverse image of FIG. 1D but not in the SC-OCTA image of FIG. 1E.

Thus, FIG. 1A shows a simplified schematic of a visible OCT system 100 that obtains 3D spectral information of a sample. The example OCT apparatus 100 of FIG. 1A images a sample with respect to a reference through a lens and galvo mirror illuminated with white laser light through a beam splitter measured using a spectrometer.

FIGS. 1B-1E show example in vivo human imaging of labial mucosa (lower lip) from a healthy volunteer. FIG. 1B shows 557 nm inverse and 620 nm inverse B-scans with their corresponding STFT windows, as well as a SC-OCTA B-scan showing contrast shadows from each vessel, with a scale bar of 200 µm. As shown in the example of FIG. 1B, spectral contrast is a ratio of spectrum 557 nm and 620 nm. STFT windows of imaged hemoglobin can be provided. Analysis of the peaks in the spectral contrast can be used to identify blood vessels without flow. Using SC-OCTA and can reduce scan time from minutes taken using traditional flow techniques down to seconds using SC-OCTA in which motion does not affect contrast of a resulting angiogram image.

FIG. 1C depicts a comparison of angiography en face projections of superficial capillary loops from traditional motion contrast OCTA (64-111 µm), 557 nm inverse (55.6-140 µm), and SC-OCTA (83-209 µm) with their corresponding line profile intensities. Depth ranges were chosen to maximize contrast of en face projections for different techniques with a scale bar of 200 µm, for example.

FIG. 1D shows a 3D rendering of 557 nm inverse with a scan area of 3.15×2.94 mm. FIG. 1E illustrates a depth-encoded vessel map of a same field of view (FOV) as FIG. 1D with saturation and value from SC-OCTA and hue from depth of vessel in 557 nm inverse with scale bars of 300 µm. FIGS. 1D-1E highlight a white arrow showing a salivary duct which is correctly not identified by SC-OCTA in FIG. 1E.

Because SC-OCTA does not rely on motion for contrast, it can image vasculature even in the setting of hemostasis. To demonstrate this capability, the serosal surface of a freshly sacrificed mouse ascending colon is imaged, as shown in FIGS. 2A-2D. This is the first-time angiography has been performed on non-living tissue with endogenous contrast using OCT. A 3D rendering of the 557 nm inverse image, FIG. 2A, and SC-OCTA en face projection, FIG. 2B, show two large vessels with branching smaller vessels. Capillary density around the colonic crypts is not pronounced due to loss of blood volume and blood pressure leading to capillary collapse. Images of a freshly sacrificed mouse anterior abdominal wall with omentum overlying abdominal muscles are shown in FIGS. 2B-2D. FIG. 2B shows how SC-OCTA easily differentiates blood vessels (the far left and far right arrows) from low scattering lymphatic vessels (the middle arrow) and adipocytes. FIG. 2B also shows a B-scan of depth integrated SC-OCTA, where each pixel in the SC-OCTA image is integrated 50 µm along depth and multiplied by the 557 nm inverse image. The depth integration technique enhances vessel contrast and reduces shadowing allowing the vessels to be represented in 3D and not rely on en face projection to integrate the shadow along depth for visualization as shown by FIG. 2C. In certain examples, a depth integration technique allows labial mucosa vasculature all the way down to the capillary level to be differentiated from the salivary duct and precapillary tissue in 3D. In certain examples, depth integrated SC-OCTA can image branches of coronary arteries. In certain examples, blood vessels are easily differentiated from numerous low scattering structures in the sacrificed mouse abdominal wall. The high resolution and contrast of the visible spectrum provided imaging of lymphatic valves, shown in FIG. 2C, where the valve's tricuspid structure is easily discerned. Certain examples can generate a 3D flythrough of lymphatic valve 1 (LV1) of FIG. 2C.

Figure 2A:
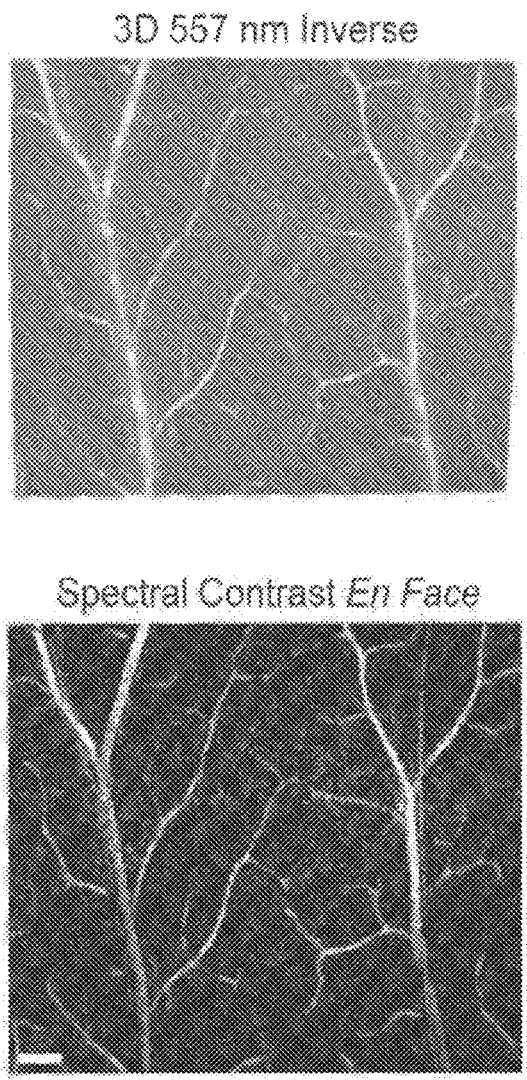
FIGS. 2A-2D.
Figure 2B:
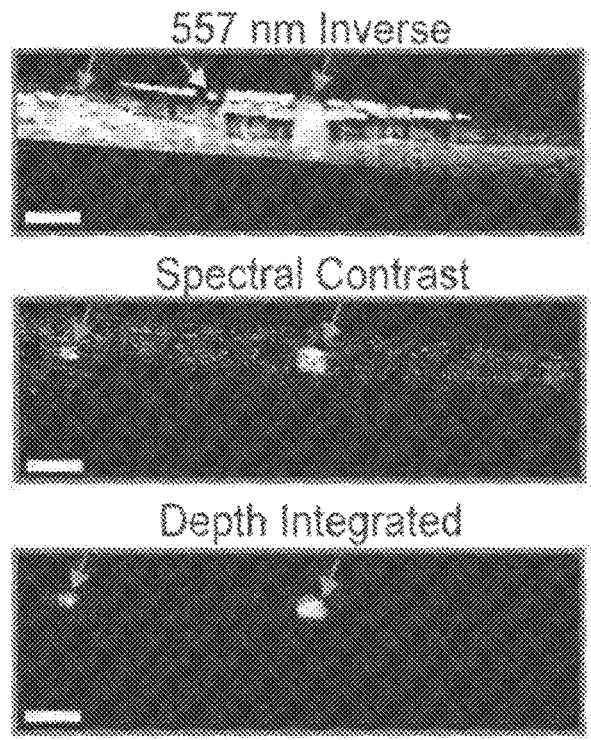
Figure 2C:
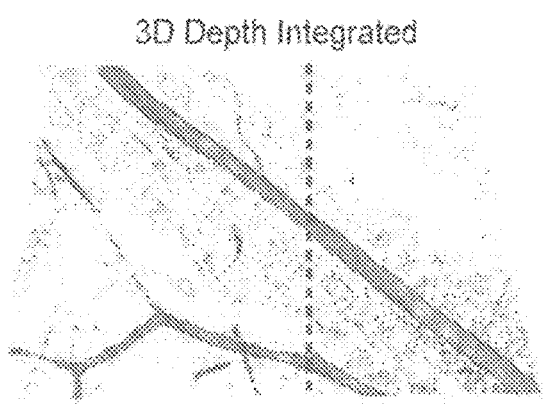
Figure 2D:
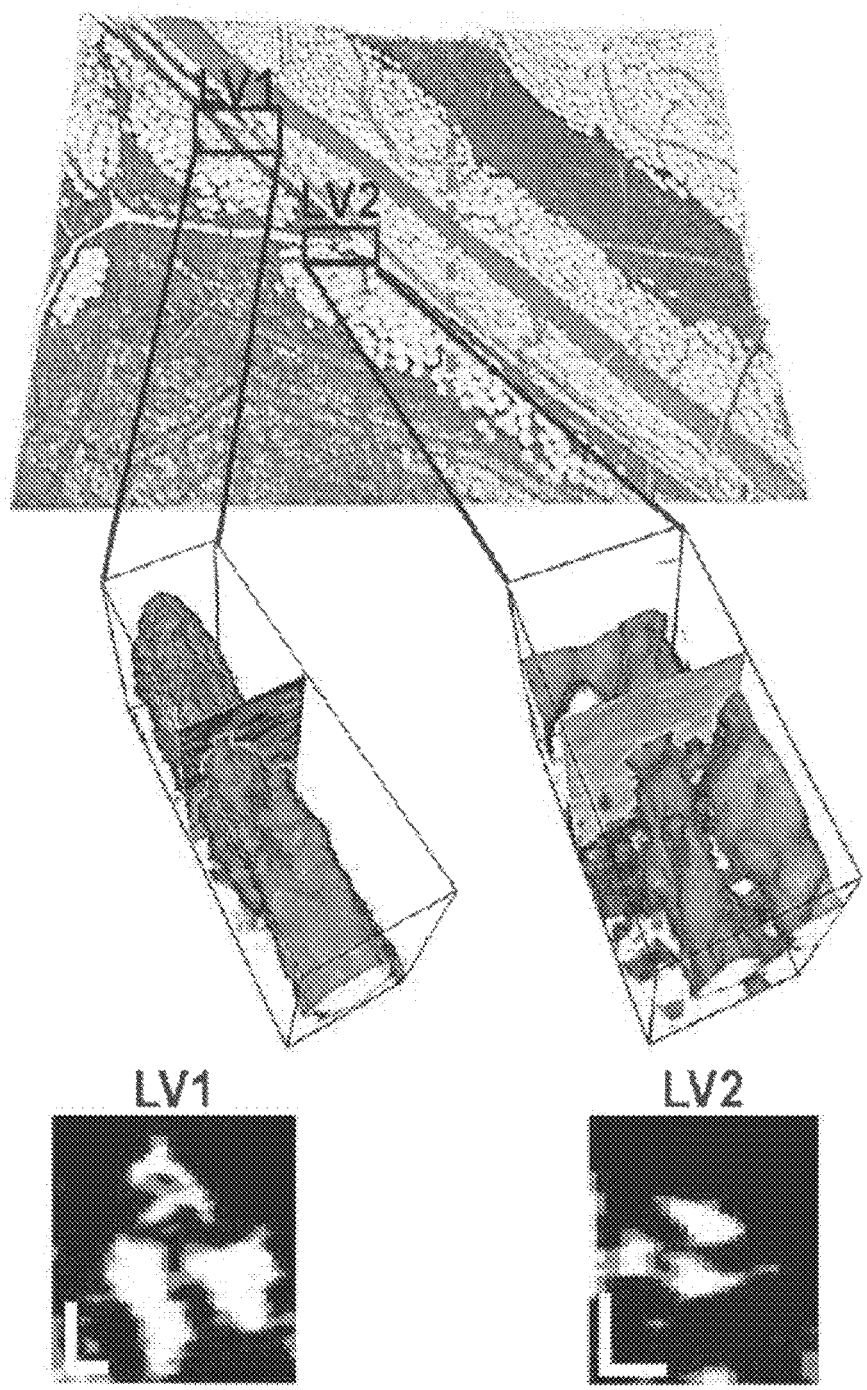

FIG. 2A shows an imaging serosal surface of sacrificed mouse colon tissue with a 3D rendering of 557 nm inverse, scan area of 2.9×2.36 mm, en face projection (70-168 µm) SC-OCTA, and scale bar of 250 µm. FIGS. 2B-2D depict example imaging of sacrificed mouse anterior abdominal wall. FIG. 2B shows a B-scan comparison of 557 nm inverse, SC-OCTA, and Depth Integrated SC-OCTA showing how blood is only highlighted using spectral contrast.

The far left and far right arrows point to blood vessels and the middle arrow points to lymphatic vessel. Scale Bar: 250 µm. FIG. 2C depicts a 3D rendering of Depth Integrated SC-OCTA showing blood vessels with a scan area of 2.52× 3.78 mm. FIG. 2D provides a 3D rendering of 557 nm inverse with blow up 3D rendering and B-scan cross sections of lymphatic valves, showing a tricuspid valvular structure. FIG. 2D includes a bounding box for LV1: 336× 112×105 µm, a bounding box for LV2: 256×141×130 µm, and scale bars of 30 µm. The dotted line in FIGS. 2C-2D show a cross section location of FIG. 2B.

Figure 3A:
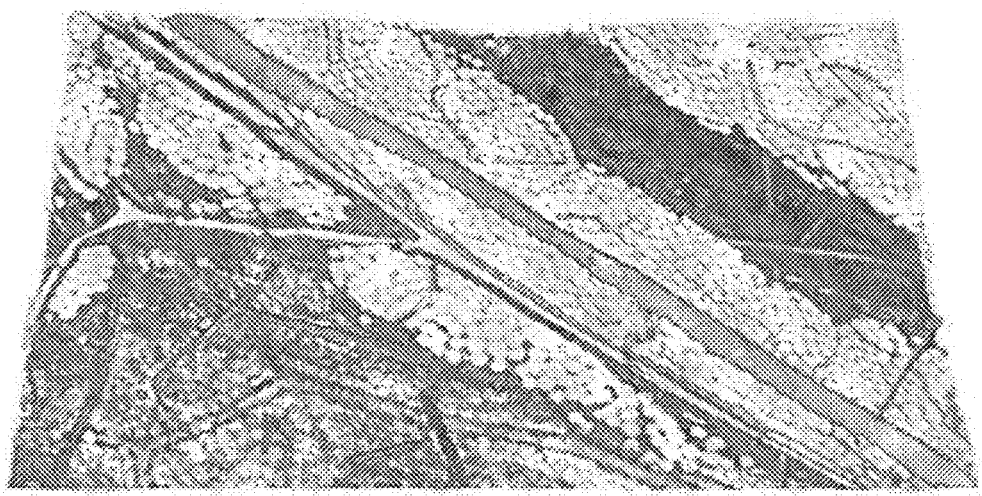
FIGS. 3A-3C.
Figure 3B:
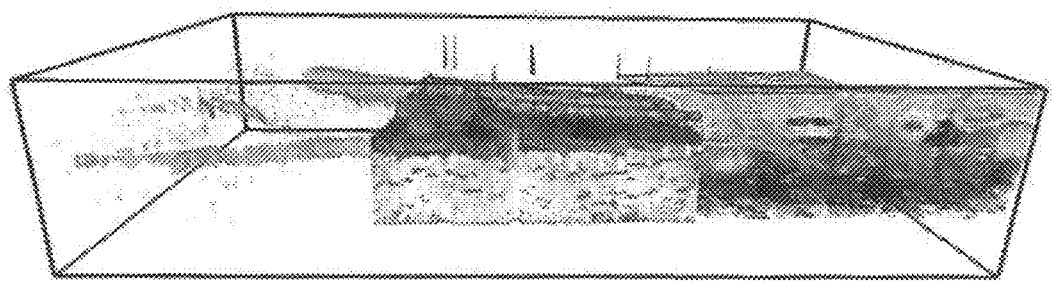
Figure 3C:
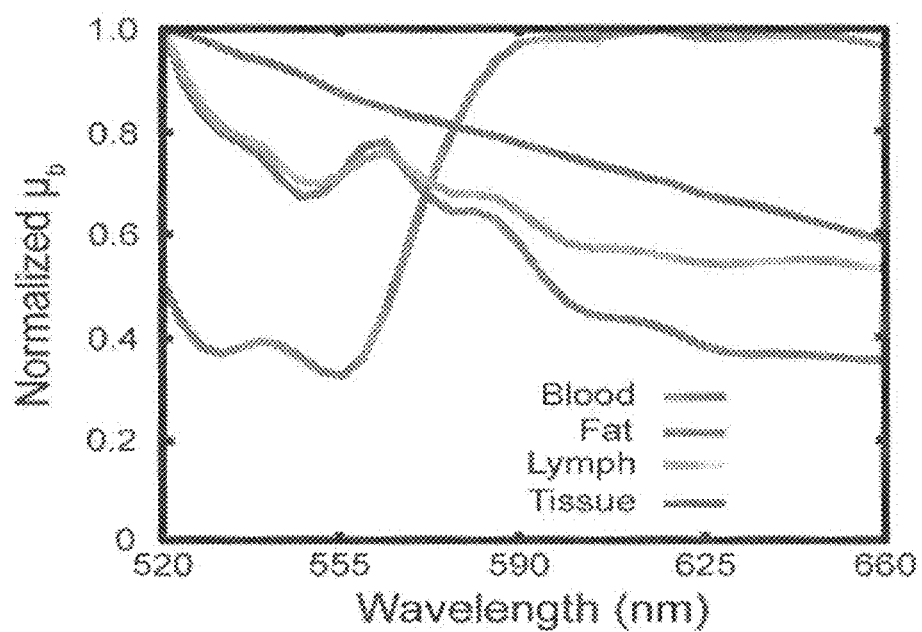

FIG. 3A shows a color-coded 3D rendering of sacrificed mouse omentum. FIG. 3A depicts a depth integrated SC-OCTA image showing blood vessels and 557 nm inverse showing adipocytes and lymphatics with a scanning area of 2.52×3.78 mm. FIG. 3B shows a side view peel-away of FIG. 3A illustrating depth integrated SC-OCTA, 557 nm Inverse and full spectrum 505-695 nm OCT intensity with a bounding box of 2.52×3.78×0.7 mm. FIG. 3C depicts plots of normalized median backscattering (pb) spectra from fat, lymphatic, blood vessels, and tissue measured by visible OCT.

Thus, certain examples provide improved systems, apparatus, and robust methods for single-scan angiography and tissue differentiation with molecular sensitivity using spectroscopic visible OCT. FIGS. 3A-3B provide 3D visualizations of this ability with highly scattering tissue, vessels, and adipose/lymphatic tissue. The distinct spectroscopic features which allowed these structures to be differentiated can be seen with the measured spectra in FIG. 3C. Tissue's spectra had a gradual decay with increasing wavelength which has been previously noted. Adipose/lymphatic tissue decreased more rapidly behaving like Rayleigh scatters due to their low scattering nature. The low scattering nature allows them to be easily distinguished from higher scattering tissue with the 557 nm inverse. Blood has a characteristic absorption peak at ~550 nm, which is sensed by SC-OCTA. The spectra of the adipocytes (fat) and lymphatics are similar, which is expected since lymphatic vessels are associated with fat transport in abdominal areas. Certain examples optimize and/or otherwise improve SC-OCTA algorithms and implement into visible OCT endoscopy for minimally invasive in vivo imaging with molecular sensitivity.

Example SD-OCT System Configuration

Figure 4:
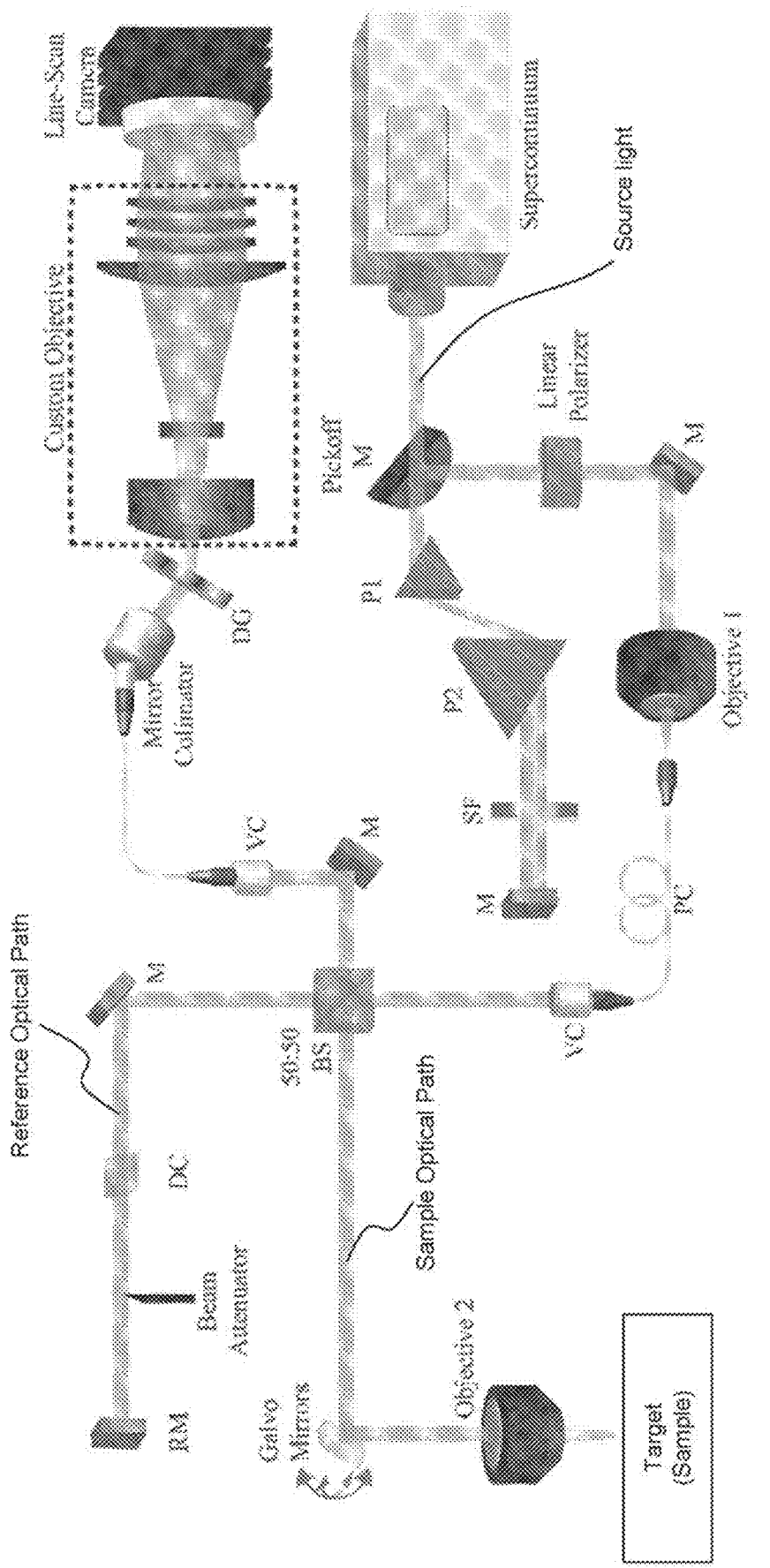
FIG. 4. A schematic of an exemplary system for imaging a target using OCT scanning, according to certain embodiments.

Certain examples provide a SD-OCT apparatus 400 configured as shown in the example of FIG. 4. The example OCT apparatus 400 uses a line-scan camera with a supercontinuum laser to image a sample using a custom objective as well as first and second objectives, a plurality of mirrors (M), prisms (P1 and P2), a spatial filter (SF), a paddle polarization controller (PC), visible collimator (VC), a beam splitter (BS), a dispersion compensator (DC), a reference mirror (RM), a diffraction grating (DG), etc.

In certain examples, a supercontinuum laser (e.g., NKT Photonics, SuperK Extreme EXW-6, etc.) is set to 100% output power and the direct output from the laser is first sent through a splitter box (e.g., NKT Phontics, SpectraK Split, etc.), not shown in this figure, which optionally includes a 400-850 nm reflective band-pass filter to remove the infrared parts of the spectrum. The spectrum of light is then smoothed using two prisms and spatial filter to have a similar dynamic range across the spectrum. Light first passes over a pickup off mirror and into Prism 1 (e.g., Thorlabs, F2 Equilateral Prism, PS854, etc.). An incident angle of the beam onto Prism 1 is set to a minimum angle of deviation to minimize reflections off prism-air interfaces. Prism 1 refracts the light and angularly disperses the light as a function of wavelength. After a sufficient distance to spread out the spectrum in space, the light enters Prism 2 (e.g., Thorlabs, F2 Equilateral Prism, PS858, etc.). Prism 2 is adjusted so that the incident surface is parallel to the output surface of Prism 1. Prism 2 recollimates the light but with the beam being dispersed in wavelength across its horizontal axis. A piece of highly absorbing aluminum foil (e.g., Thorlabs, BKF12, etc.) can be cut to the shape of an oval and attached to a 2-dimensional translational mount to act as the spatial filter. The translational mount allows for fine tuning of the spectrum as the foil attenuates parts of the beam cross-section. The light is then reflected off a mirror that slightly deviates the beam downwards to allow the returning beam through the prisms to be reflected by a pick off mirror. The light then passes through a linear polarizer (e.g., Newport, 10LP-VIS-B, etc.) and is coupled into 7 meters of SM 600 fiber (e.g., Thorlabs, 900 µm tight buffer, etc.) with Objective 1 (e.g., Edmund Optics, 33-438, etc.). The SM 600 fiber is threaded through two sets of three-paddle polarization controllers (e.g., Thorlabs, FPC562, etc.). As illustrated in FIG. 4, as an illustrative example, the reference optical path and the sample optical path are diverged a beam splitter (BS). Between the beam splitter and the sample, light associated with the sample optical path may be directed to the target, interact with the target, and such that the interacted (light modified by interactions; e.g., attenuated light; e.g., backscattered light) be collected back into the sample optical path. Between the beam splitter and the reference mirror (RM), light associated with the reference optical path may be directed to the reference mirror (RM), interact with the target (substantially reflect), and then the reflected light may be collected and directed within reference optical path. At other portions of the reference optical path and the sample optical path, such as between the beam splitter and the camera and/or between the beam splitter and the source light, the reference optical path and the sample optical path are optionally substantially collinear, congruent, or coincident.

In certain examples, only 2 paddles are used on one of the controllers. The linear polarizer and two sets of three-paddle polarization controllers are used to provide sufficient polarization control to maximize interference efficiency of the OCT interferometer across its broad bandwidth. Light is collimated out of the SM600 fiber using a fiber port collimator (e.g., OZ Optics, HPUCO-23-400/700-S-10AC, etc.) to a cube 50:50 beam splitter (e.g., Thorlabs, CM1-BS1, etc.) which directs light to a sample arm and reference arm. In the sample arm, a two-dimensional galvanometric mirror system (e.g., Thorlabs, GVS002 TSH25379-X, etc.) allows the beam to be point-wise scanned across the sample. The beam is focused onto the sample using Objective 2 (e.g., Thorlabs, LSM03-VIS, etc.). The reference arm contains a dispersion compensator (e.g., Thorlabs, LSM03DC-VIS, etc.). A razor blade is used to the attenuate the beam in the sample arm to have the reference power be within the dynamic range of the spectrometer. The reference mirror in the reference arm is on a translation stage to allow for fine adjustment of the reference arm path length with respect to the sample arm path length. A fiber port collimator (e.g., OZ Optics, HPUCO-23-400/700-S-10AC, etc.) collects the interfered beam into SM-460B fiber (e.g., Thorlabs, P1-460B-FC-5, etc.) which directs the light to the custom built visible spectrometer. Light is focused onto a 1200 lines/mm grating (e.g., Wasatch Photonics, etc.) from the SM-460B fiber with a mirror fiber collimator (e.g., Thorlabs, RC12APC-P01, etc.). The grating angularly disperses the light as a function of wavelength onto a 6-element focusing objective (e.g., Effective Focal Length=123.7 mm, etc.). The custom objective focused the light onto a 4096×2 line scan camera (e.g., Basler, spL4096-140 km). The mirror collimator, grating, and custom objective are on a translational mount to allow fine tuning of the distance between the components and the line scan camera. A spectrometer across this broad-bandwidth can be particularly challenging to construct and align.

Example System Sensitivity and Resolution

In operation, using the impulse response of a mirror, the sensitivity of the system is found to be 91.61 dB at an illumination power of 11.2 mW, for example. The mirror impulse response is also used in calculating the air axial resolution, which can be 1.53 µm, for example, corresponding to a tissue axial resolution of ~1.15 µm, for example. The air axial resolution for the two Kaiser windows used in SC-OCTA can be 3.8 µm and 4.72 µm for the 557 nm window and 620 nm window, respectively, for example. The air axial imaging range for the system can be 1 mm with a roll-off sensitivity of approximately −10 dB/mm, for example. The system sensitivity measurements can be seen in FIG. 23, for example. The lateral resolution can be 8.11 µm by measuring the edge response of a razor blade placed at the focal point, for example. The first spatial derivative of the OCT intensity across the razor blade is computed using a Savitzky-Golay filter, and its full width at half-maximum s computed to give the lateral spatial resolution of the system. This same method is used to determine the resolution of the high numerical aperture system setup used in obtaining FIG. 10C.

Example Acquisition Parameters

In certain examples, the spectrometer for data collected was set to 45,000 A-lines/sec at an exposure time of 18 µsec. Data collected in FIG. 2C for OCTA includes 4 repetitive B-scans containing 400 A-lines at each cross section and 512 B-scans in the C-scan direction, taking a total of 18.2 sec and covering a field of view of 1.76×1.76 mm. OCT data collected for inverse OCT intensity and SC-OCTA images in FIG. 2C was collected in the same manor except with no B-scan repetitions so acquisition time was reduced to 4.5 sec. All other data collected in this example (not FIG. 2C) was acquired by scanning a field of view of 3.78×3.78 mm and contained 900×900 A-lines, taking 18 sec.

Example Axial Point Spread Function (PSF) and System Roll-Off Calibration

Spectroscopic OCT data can be normalized by an aqueous calibration solution which is measured following sample imaging. In certain examples, calibration is performed after an imaging session because changes to polarization or reference arm position can change calibration data. In a perfectly static system, only one calibration can be required, but if the fibers in the system have slightly moved between imaging sessions, this can affect polarization and change the interference efficiency across the spectrum, leading to alterations in the relative intensity of the sampling windows. Likewise, if the reference arm position changes with respect to the focal point of the objective, the intensity of the sampling windows can be altered as a function of depth. The aqueous solution can include 80 nm sulfate latex beads (e.g., Molecular Probes by Life Technologies, 8% w/v, etc.) diluted to a concentration of 1% with deionized water. The solution can be placed on a piece of angled quartz glass and imaged at 9 equally spaced locations in the axial direction using a 3D stage (e.g., Zaber, X-XYZ-LSQ150B-K0060-SQ3, etc.). In certain examples, a starting bead surface location is ~150 µm from the reference-sample zero-path length difference and an ending bead surface position is ~950 µm from the reference-sample zero-path length difference. The OCT intensity for each Short-Time Fourier Transform (STFT) window from 1.4 µm to 8.4 µm into the bead solution is averaged for each depth location and then interpolated along depth to have an axial intensity calibration for each STFT window.

Example RAW Interferogram Data Processing

Interferogram data (data collected from the spectrometer) can be processed in MATLAB utilizing a CPU and GPU. The raw interferogram data first has its direct current component removed and then is normalized to the reference arm intensity. The data is then multiplied by its sampling window so a STFT can be performed. Kaiser sampling windows are chosen for spectral-contrast-based angiography to reduce sidelobes and reduce the transition band. Dispersion correction can also be applied when applicable. The data is then interpolated to be equally spaced in wave number space and fast Fourier transformed on the GPU. The data is then divided by the axial calibration intensity, squared, and multiplied by the center wavenumber of the sampling window raised to the fourth. To summarize, the spectrally dependent OCT A-line intensity, I(k,z), is calculated using the following:

$$I(k, z) = \left(\frac{I_{samp}(k, z)}{I_{cal}(k, z)}\right)^2 k^4, \quad \text{(Eq. 1)}$$

where k is a wavenumber (2π/wavelength), z is a depth along the A-line, and Isamp (k,z) and Ical (k,z) are STFTs of the sample and axial intensity calibration, respectively.

Example Edge Detection

A surface of the sample is to be calculated to compute a depth of blood vessels and remove air on top of the sample for inverse OCT intensity images. The upper surface of the sample is determined by a series of morphological operations on each B-scan. The series of morphological operations includes smoothing each using gaussian and median filters, contrast enhancing, and applying an extended maxima transform to find the largest continuous region of high contrast scattering. The parameters of each operation can be heuristically determined for each sample. The surface points are calculated for each B-scan, and the 2D surface map is filled in using a surface extrapolate and smoothed.

Example OCTA Processing

The OCTA en face projection shown in FIG. 2C is generated using a phase sensitive decorrelation algorithm. The OCT data from consecutive B-Scans is first corrected for global phase fluctuations using a phase modifier in the axial and B-scan direction. The difference between the second to fourth consecutive B-scans is then calculated. This can be performed for STFT Gaussian windows centered at 593.96 nm, 615.54 nm, and 638.74 nm all with a FWHM of ~50 nm, for example. The OCTA data produced for all the Gaussian windows and subtractions is then averaged to produce final 3D OCTA data for the en face projection image.

Example Inverse 557 nm OCT Intensity Processing 557 nm inverse OCT intensity data, $I^-$(557 nm), can be produced by the following:

$$\hat{I}(557\text{ nm}, z) = \text{medfilt}\left(\log_{10}\left(\frac{1}{I(557\text{ nm})}\right)\right), \quad \text{(Eq. 2)}$$

where I(557 nm) is the 3D spectrally dependent OCT data of the 557 nm Kaiser window and medfilt denotes a 10.8× 10.8×4.2 µm (e.g., B-scan Direction, C-scan Direction, Depth Direction) median filter. The air surface above the sample was removed using the edge detection algorithm. The Γ⁻(557 nm) data shown for the labial mucosa in FIG. 1D has additional processing actions performed including connected component analysis followed by a binary opening operation that is multiplied by the original Γ⁻(557 nm) data. The rest of the Γ⁻(557 nm) data may not have had connected component analysis or opening operations performed on it.

Example SC-OCTA Processing

The OCT data for each Kaiser window are dispersion compensated or axially shifted to co-register the two windows and help ensure that edges are not highlighted in SC-OCTA due to poor co-registration. The 3D SC-OCTA intensity, $I_{SC-OCTA}$, can be calculated as follows:

$$I_{SC-OCTA} = \text{medfilt}\left(\log_{10}\left(\frac{\text{medfilt }(I(620 \text{ nm}))}{\text{medfilt }(I(557 \text{ nm}))}\right)\right). \quad \text{(Eq. 3)}$$

where medfilt is the same size as that used in (Eq. 2) and I(620 nm) is a 3D spectrally dependent OCT data of the 620 nm Kaiser window.

The 3D depth integrated SC-OCTA, $I_{DI,SC-OCTA}$, can be calculated as follows:

$$I_{DI,SC-OCTA}(z) = \frac{\hat{I}^*(557 \text{ nm}, z)\sum_{i=1}^{dz} I_{SC-OCTA}(z+i)}{dz} \quad \text{(Eq. 4)}$$

where I* (557 nm,z) is Γ⁻(557 nm,z) computed in (2) rescaled between 0 and 1, and dz is the depth integration amount.

Example Blood, Tissue, Lymphatic, and Fat Region Backscattering Spectra Calculation In order to extract the normalized backscattering spectra, µb(k), of each tissue type shown in FIG. 3C, 3D masks can be created to isolate each of the following: vascular and lymphatic networks, adipocytes, and tissue. The mask for the vascular network is generated using a simple binary threshold on the depth integrated SC-OCTA image. Morphological operations, including binary opening and eroding are applied with an effect size chosen heuristically to help ensure all voxels in the mask are safely within the blood vessel domains. The lymphatic network can be manually segmented from the 557 nm inverse OCT intensity image. Adipose cells are segmented using an extended-minimum transform on the full spectrum OCT intensity image to find large continuous blobs of low scattering regions; however, cells in the axial path of blood vessels can be avoided. The tissue can be extracted based on a threshold range, while avoiding the above expanded masks, for example.

Each 3D mask is applied to a 34 wavenumber window spectral cube, and a median spectra is computed and plotted in FIG. 3C. The 34 window spectral cube is generated with a STFT using a Gaussian window with a FWHM of 0.37 µm-1 with the windows linearly spaced in wavenumber, for example. Normalized pb(k) is related to I(k) utilizing the relation that $\mu_b(k) \sim I(k)^3$.

Example: Vessel Phantom

Figure 11A:
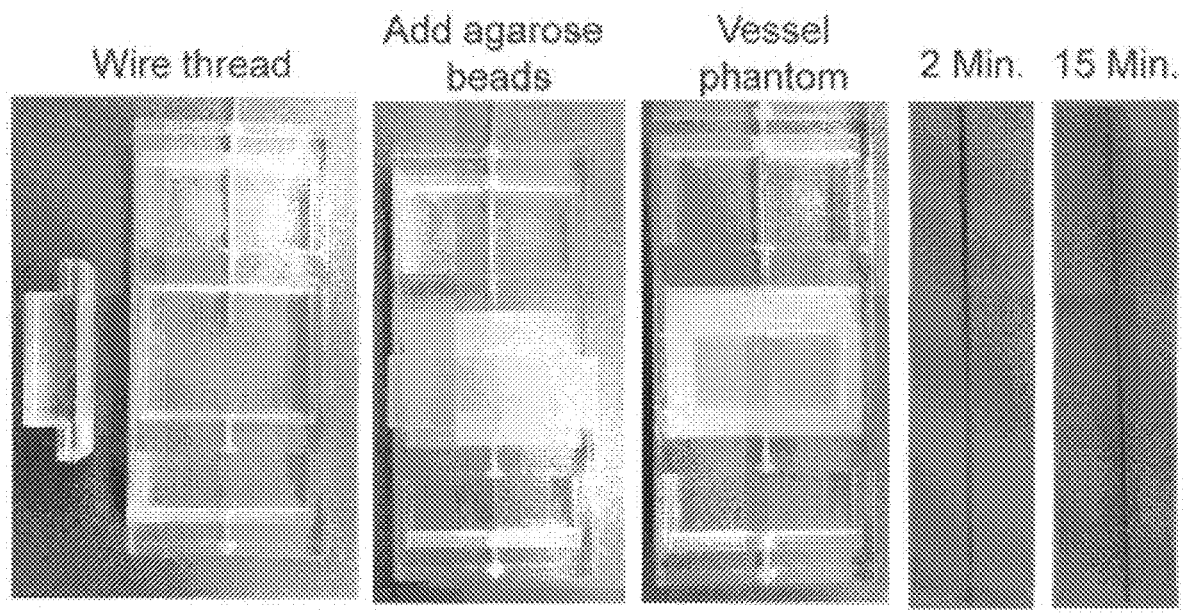
FIG. 11A. Construction of blood vessel phantom and photographs taken with smart phone of blood diffusion being observed at 2 and 15 minutes after flowing blood through the phantom.
Figure 11B:
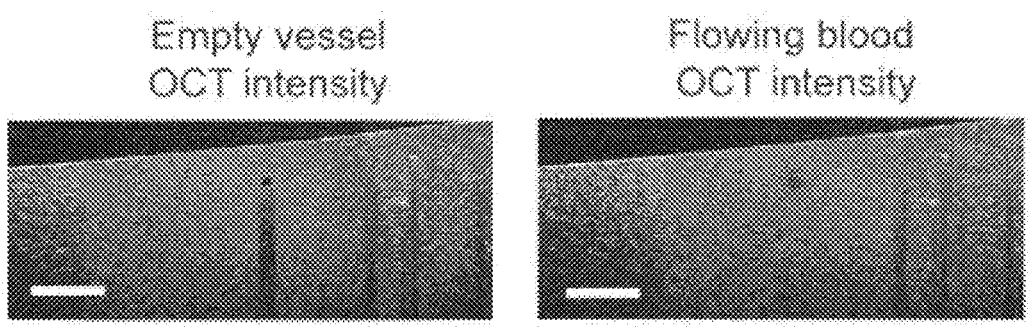
FIG. 11B. OCT Intensity B-scans of vessel phantom before and after flowing blood through. From OCT image diameter was measured to be ~45 µm before blood was flown through and ~55 µm after, with a syringe pump set to 0.0006 µL/sec. A shadow is cast beneath the empty vessel because of reflections between air and the vessel wall.
Figure 11C:
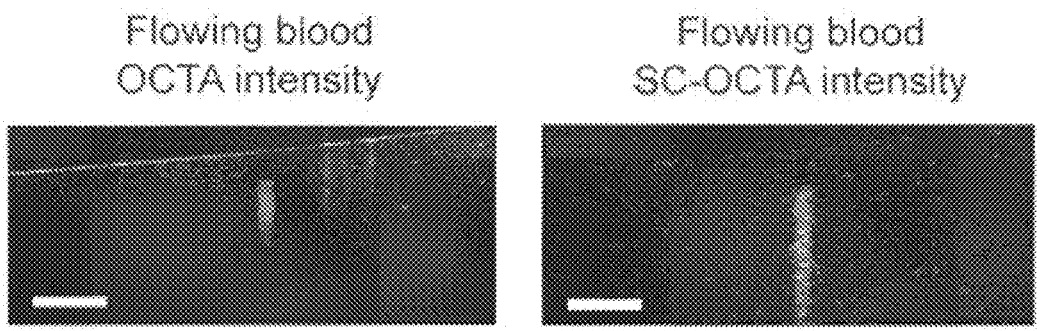
FIG. 11C. Cross sectional examples of OCTA and SC-OCTA of vessel phantom with flowing blood.
Figure 12:
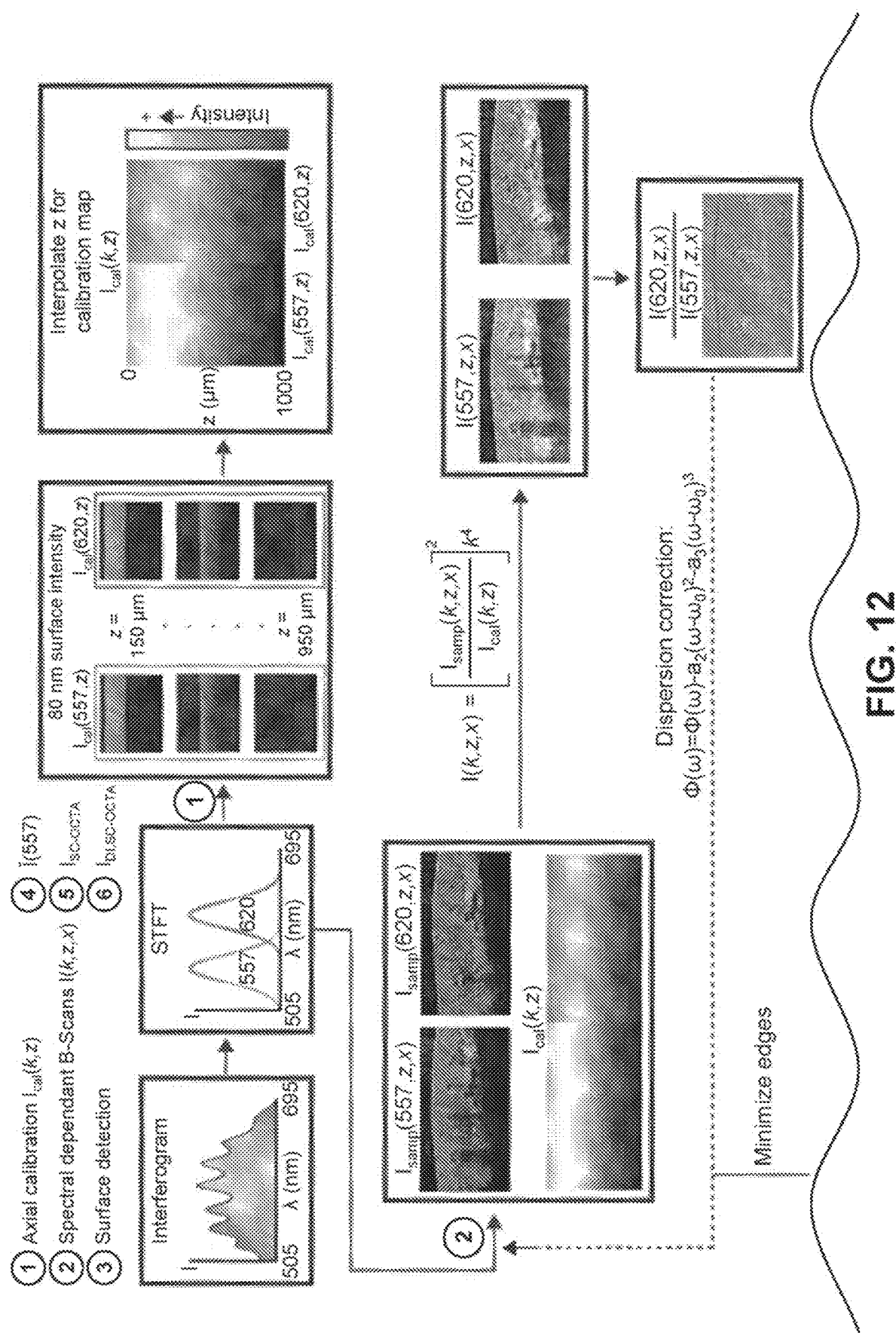
FIG. 12. Flow chart showing processing steps for generating spectral-contrast-based angiography images ($\tilde{I}(557)$, $I_{SC-OCTA}$, $I_{DI,SC-OCTA}$). The coordinate z refers to the depth direction along an A-line and x is the b-scan direction. m is referring to a 3D median filter that is applied to the z, x, and C-scan direction.
Figure 12:
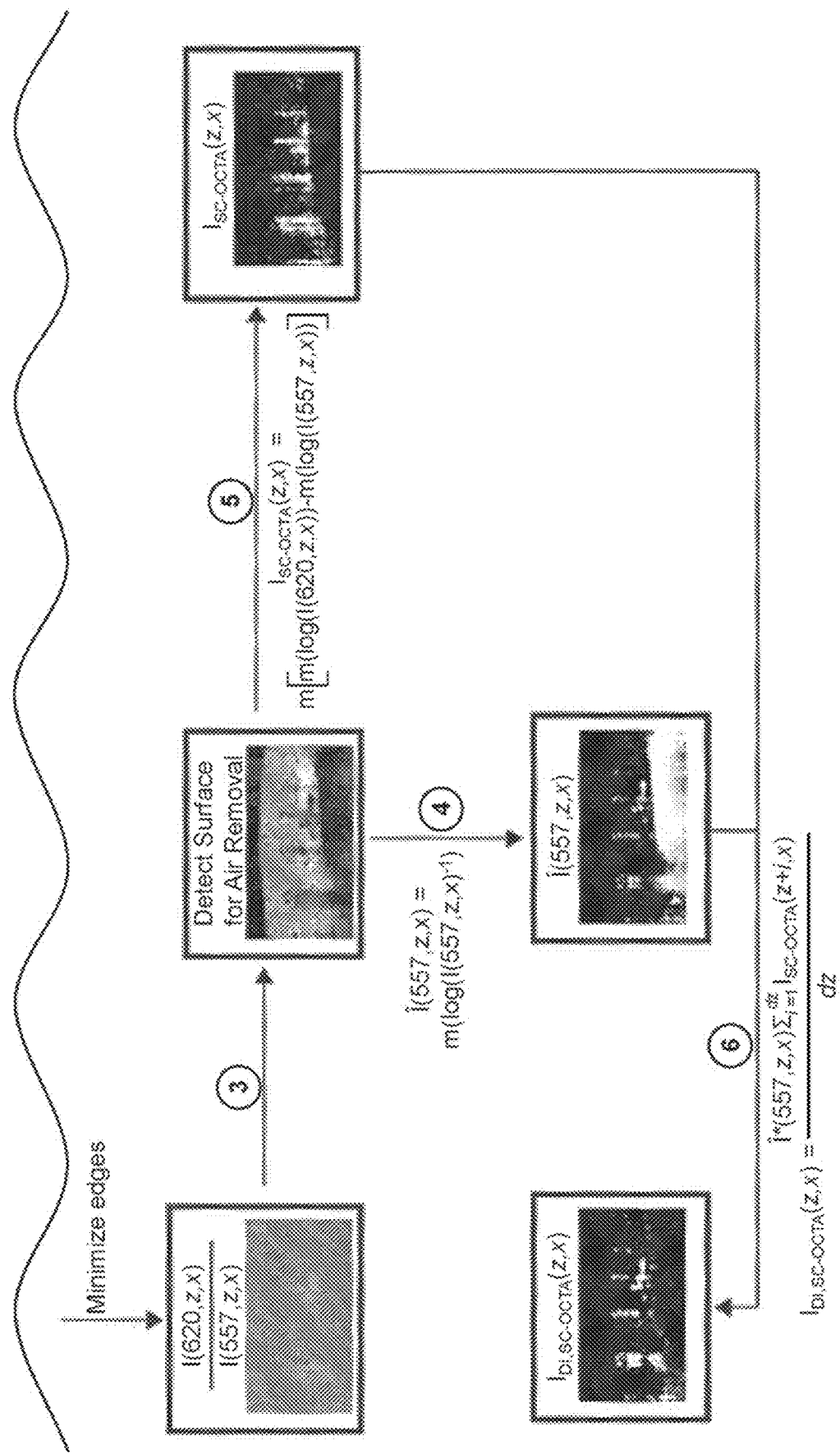

To mimic tissue, a vessel phantom consisting of water, 4% agarose (Fischer Bioreagents), and 1% aqueous 80 nm polystyrene beads (Molecular Probes by Life Technologies, 8% w/v) can be prepared (Figure S6 (a)). A 3D printed mold can be made to hold the phantom. First, FEP tubing (outer diameter: 800 µm, inner diameter 250 µm; The Dolomite Center Ltd) is threaded into the 3D printed mold to serve as a conduit to deliver blood to the phantom. From the opposite side of the mold, 50 µm diameter tungsten wire (Malin Co.) is threaded into the mold and into the opening of the FEP tubing. A 3D printed spacer is then placed on top of the mold to create an ~100 µm gap between the spacer and the tungsten wire. Agarose and water are mixed and heated. Once the agarose is dissolved, an aqueous 80 nm polystyrene bead solution is added, and the mixture is poured into the mold. After the solution solidifies in the mold, the spacer is carefully removed, and the tungsten wire i pulled out, creating an ~45 µm diameter channel that expanded to ~55 µm after hepranized bovine blood (Quad Five) is flown through at a rate of 0.0006 µL/sec with a syringe pump (Harvard Apparatus PhD 2000) (Figure S6 (b)). Since the phantom is made of agarose, this limited its operation lifetime due to blood diffusion; therefore, a new phantom is made for each experiment. Agarose gel is utilized as it allowed for the creation of more accurate tissue-like scattering media directly around the vessel. Nonpolar polymers, such polydimethylsiloxane (PDMS), cannot mix with polystyrene bead solutions, making it difficult to control the optical properties of such polymers. Controlling the optical properties of the surrounding media is important to properly evaluate the performance of SC-OCTA and OCTA because a large portion of the signal comes from the 'shadowing effect' directly below the vessel (FIG. 11C).

Example: SNR Calculations

SNR is calculated by the following:

$$SNR = \frac{\overline{I_v} - \overline{I_b}}{\sigma_b} \quad (5)$$

where $\overline{I_v}$ is the average vessel intensity, $\overline{I_b}$ is the average background intensity, and $\sigma_b$ is the standard deviation of the background intensity. In the phantom measurements, the standard deviation of the SNR is calculated over 10 equally sized regions of interest (FIG. 11F). Statistical analysis of the phantom SNR is performed using a two-sample t-test.

Example: In Vivo Human Labial Mucosa Imaging

Figure 25A:
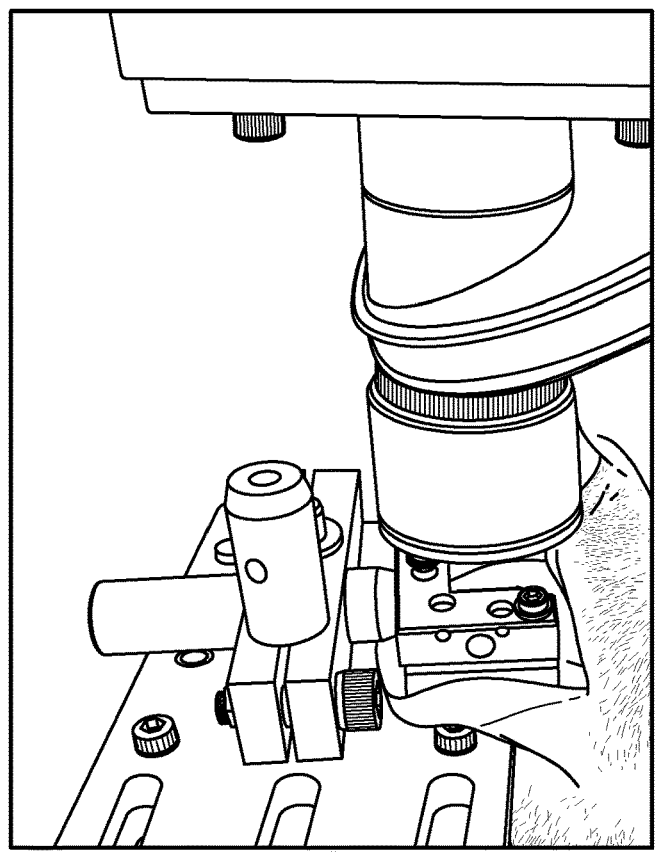
FIGS. 25A-25B.

A healthy volunteer is recruited for in vivo labial mucosa imaging. The human lip is clamped down on a manually adjustable stage to allow the sample to be moved into focus (FIG. 25A). The subject is encouraged to only breath through their nose to prevent fogging of the objective.

Example: Sacrificed Mouse Imaging

Figure 25B:
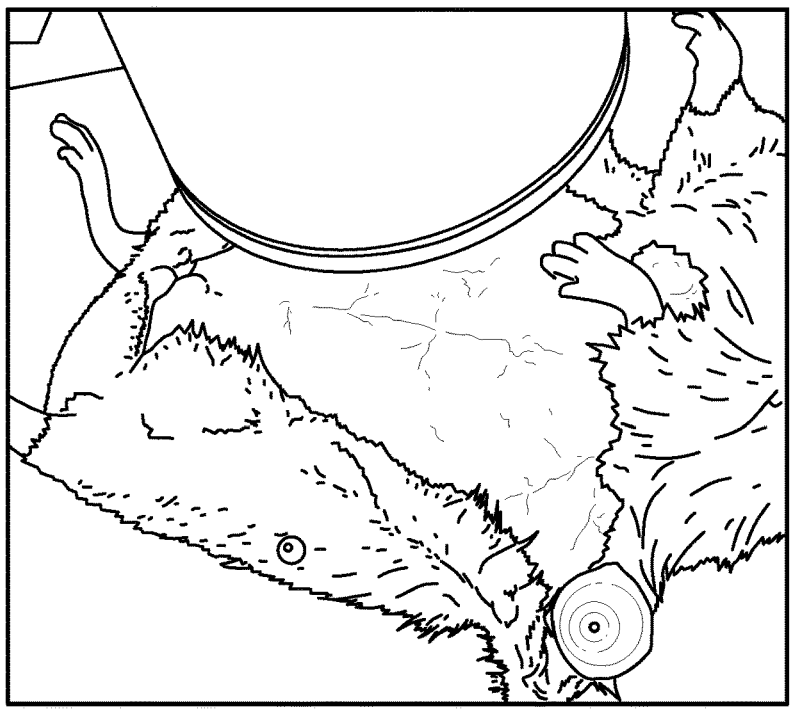

Freshly sacrificed (<2 hours postmortem) carcasses are carefully dissected and moved into focus using a 3D stage (Zaber, X-XYZ-LSQ150B-K0060-SQ3) (FIG. 25B). A c56BL/6 adult male mouse is used to image the outer surface of the ascending colon. An ICR (CD-1) adult female mouse s used for heart and anterior abdominal wall imaging. The mice are raised and sacrificed in accordance with Northwestern University IACUC standards.

Example Software and Computer Systems

In various examples, the methods and systems of the present disclosure may further include software programs on computer systems and use thereof. Accordingly, computerized control for the synchronization of system functions such as laser system operation, fluid control function, and/or data acquisition steps are within the bounds of the invention. The computer systems may be programmed to control the timing and coordination of delivery of sample to a detection system, and to control mechanisms for diverting selected samples into a different flow path. In some examples, the computer may also be programmed to store the data received from a detection system and/or process the data for subsequent analysis and display.

In some examples, the computer system can be implemented using software modules executing on computer architectures and systems such as those described below. In other examples, the functions of the system can be implemented partially or completely in firmware, programmable logic devices such as field programmable gate arrays, system on chips (SOCs), application specific integrated circuits (ASICs), or other processing and logic elements.

Figure 5:
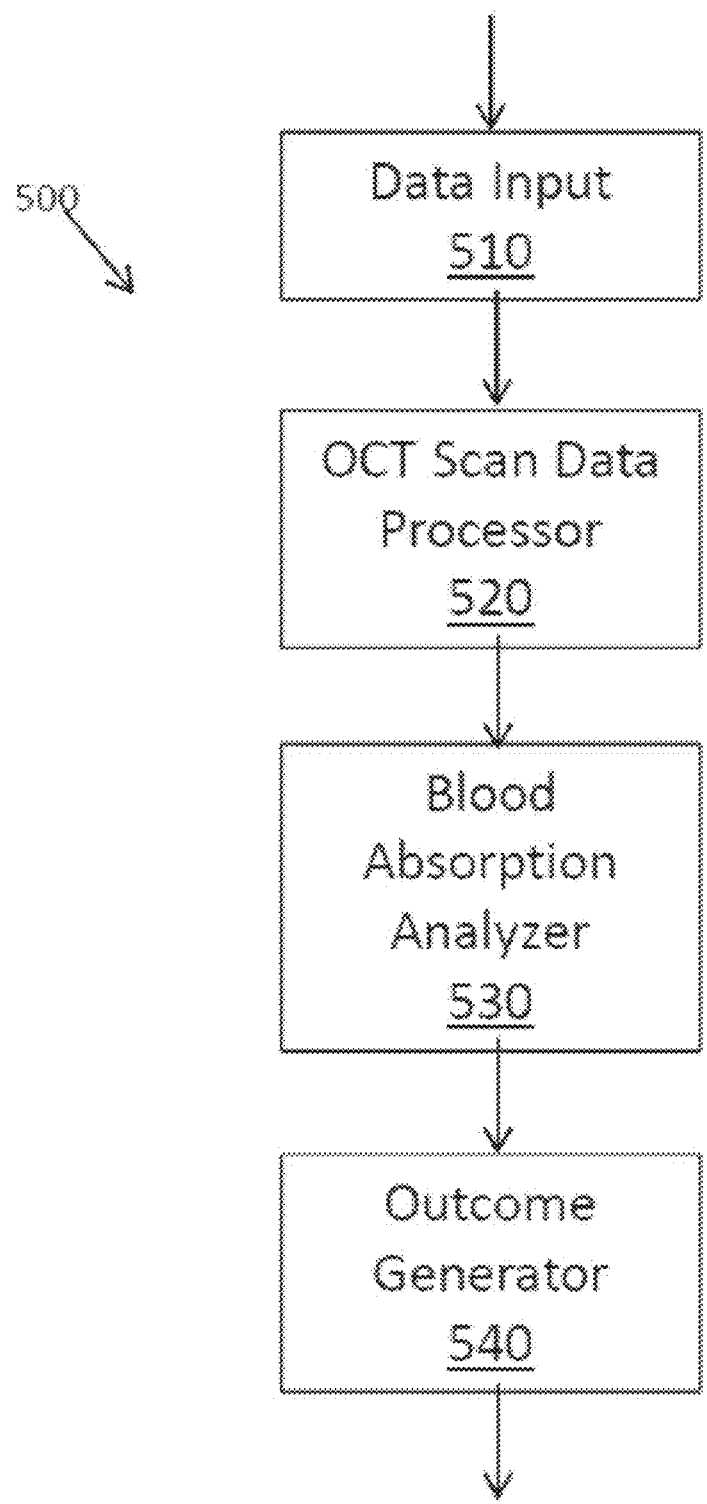
FIG. 5. A flowchart illustrating a method, or certain steps thereof, for imaging a target, according to certain embodiments disclosed herein.

For example, as shown in FIG. 5, an OCT data processing system 500 includes a data input 510 to receive OCT scan data from scanning of a target by an OCT device. One or more OCT scans may be generated and obtained by one or more components of the OCT device/system. The example system 500 includes an OCT scan data processor 520 to process/analyze the OCT scan data according to one or more criterion. The example system 500 includes a blood absorption analyzer 530 to determine vessel location in the target sample based on a blood absorption analysis of OCT scan data provided by the data processor 520. Fluid flow information can be provided by the blood absorption analyzer 530 to an outcome generator 540 to provide feedback and/or other output (e.g., display of information, printout of information, relay of information to another system (e.g., to drive another process), etc.). For example, the outcome generator 540 can provide information to a healthcare practitioner and/or diagnostic system to facilitate a medical decision.

Figure 6:
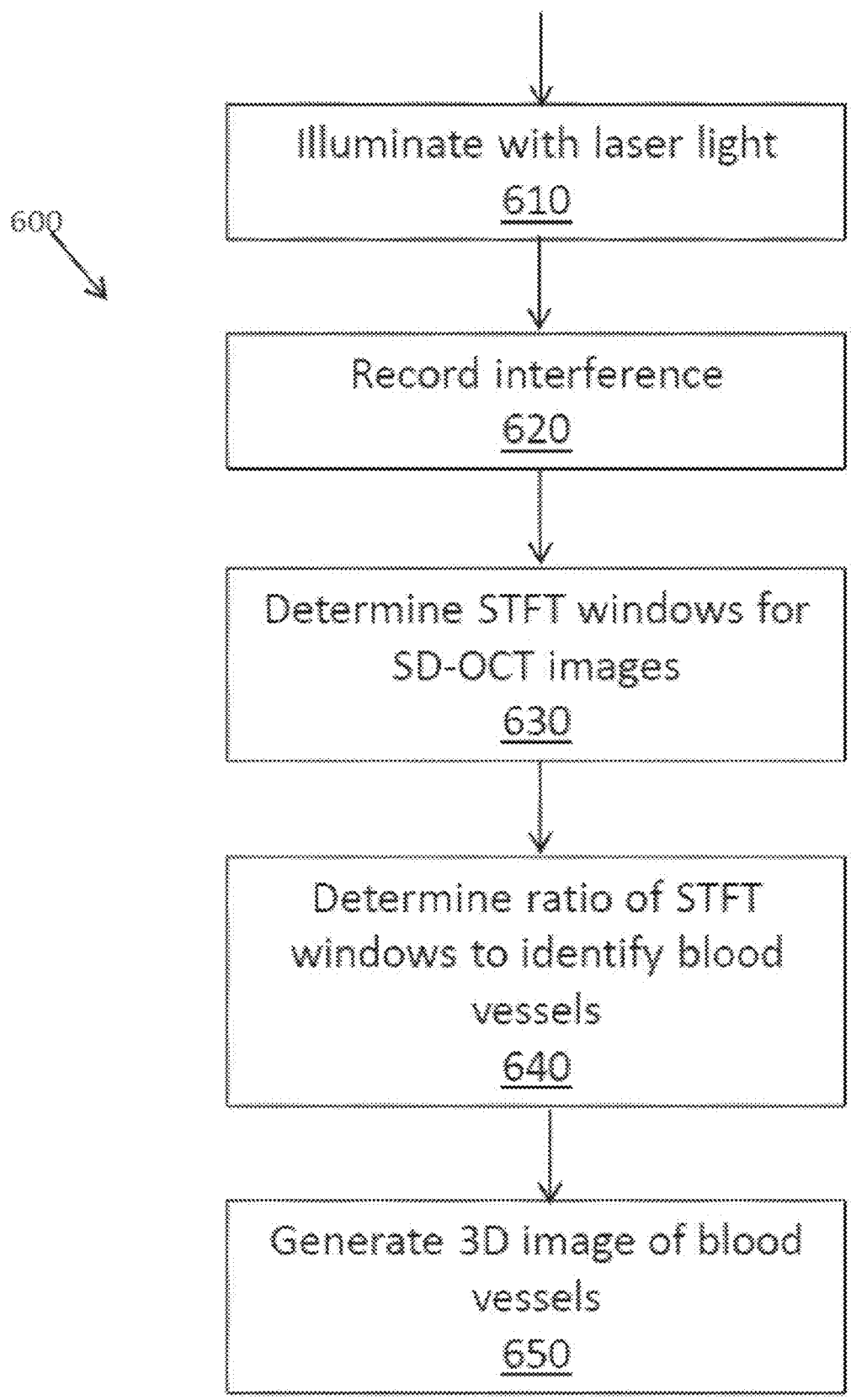
FIG. 6. A flowchart illustrating a method, or certain steps thereof, for imaging a target, according to certain embodiments disclosed herein.

FIG. 6 illustrates an example process 600 for spectral contrast OCT angiography (SC-OCTA). SC-OCTA is accomplished using a specially configured OCT system (e.g., a 500-700 nm or shorter bandwidth system, etc.) such as shown in FIG. 1A and FIG. 4. At block 610, a supercontinuum white light laser is used for illumination and split into a reference arm path and a sample arm path using a beam splitter. At block 620, interference of the light from the sample and reference arm mirror are then recorded on a spectrometer. This allows for coherence gating of sample scatterers. At block 630, two short time Fourier transform (STFT) windows are carried out to produce spectrally dependent OCT images, one at a blood absorption peak (e.g., 560 nm, etc.) and another near a blood backscattering peak (e.g., 620 nm, etc.), such as shown in FIG. 1C. Tissue typically follows Rayleigh-like scattering spectra with backscattering intensity decreasing with increasing wavelength. However, in blood, the backscattering spectra is increasing from 560 nm to 620 nm, for example. Therefore, at block 640, by taking a ratio of the two STFT windows, blood can clearly be distinguished from tissue as shown in OCT B-scans of the example of FIG. 1C, with signal appearing below vessel locations. Furthermore, at block 650, an excellent 3D image of vessels can be created by examining an inverse of the 557 window, for example, as shown in FIG. 1D. However, this image, in addition to highly absorbing structures at 560 nm, also includes low scattering structures such as a salivary duct. SC-OCTA ignores low scattering structures and is sensitive to blood vessels. This can be seen in the example of FIG. 1E, where the salivary duct structure has disappeared, as indicated by the white arrow. This also allows SC-OCTA to distinguish between low scattering lymphatic vessels and blood vessels, as shown in the example of FIG. 2A.

Figure 7:
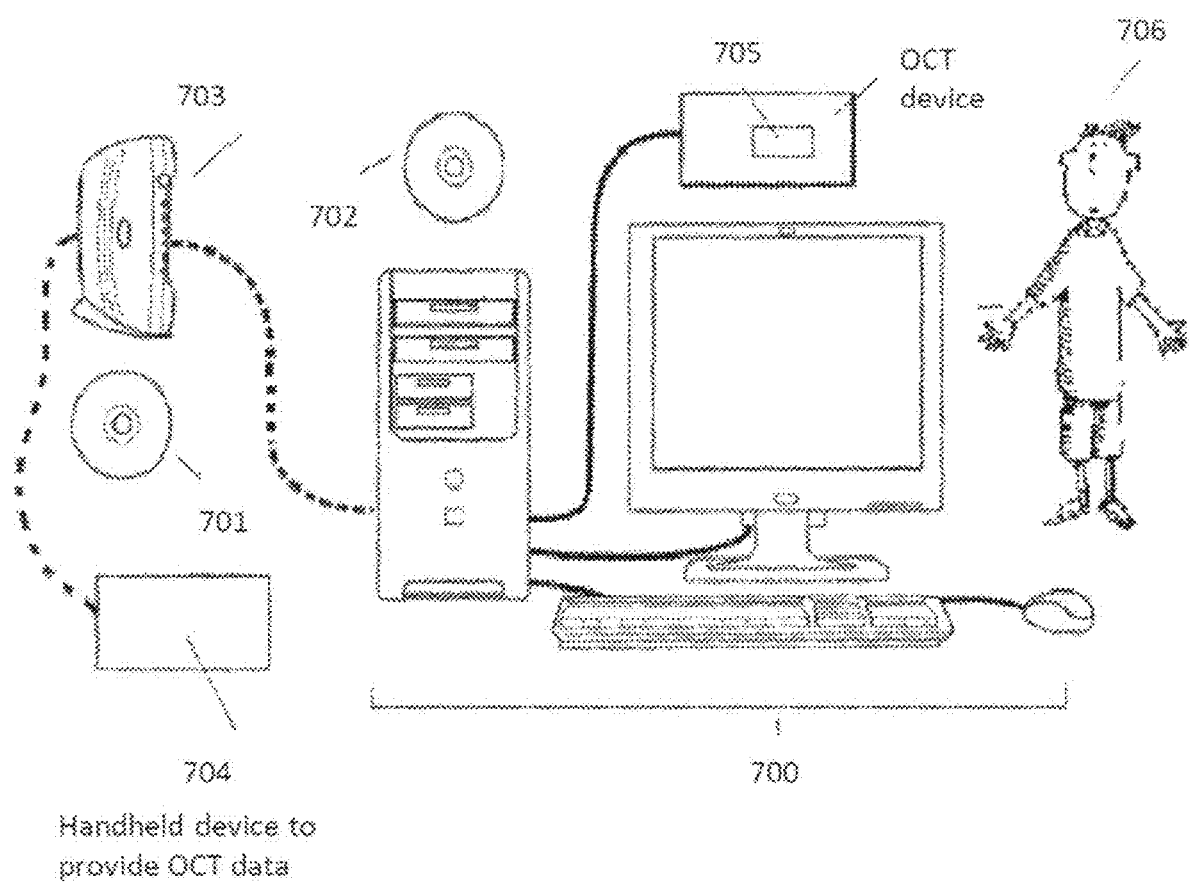
FIG. 7. A schematic of a computer system which may be used with the methods and systems disclosed herein, according to certain embodiments.

The computer system 700 illustrated in FIG. 7 may be understood as a logical apparatus that can read instructions from media 702 and/or a network port, which can optionally be connected to server 703 having fixed media 702. The system, such as shown in FIG. 7 can include a CPU, disk drives, optional input devices such as handheld devices for acquiring flow measurement data 704 or other instrument types such as a laboratory or hospital-based instrument 705. Data communication can be achieved through the indicated communication medium to a server at a local or a remote location. The communication medium can include any suitable device for transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 706 as illustrated in FIG. 7.

Figure 8:
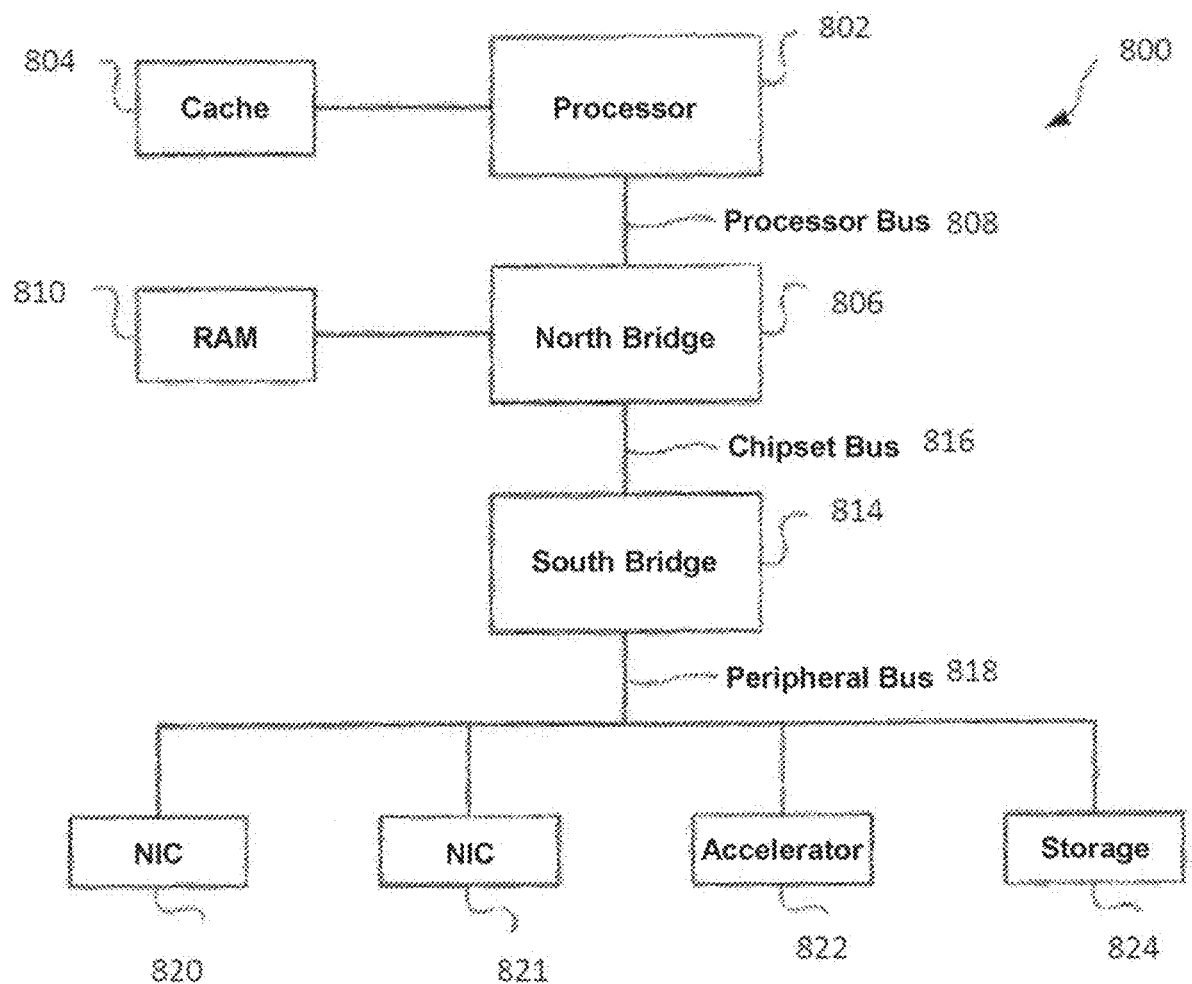
FIG. 8. A schematic of a computer system which may be used with the methods and systems disclosed herein, according to certain embodiments.

FIG. 8 is a block diagram illustrating a first example architecture of a computer system 800 that can be used in connection with the present disclosure. As depicted in FIG. 8, the example computer system can include a processor 802 for processing instructions. Non-limiting examples of processors include: Intel Xeon™ processor, AMD Opteron™ processor, Samsung 32-bit RISC ARM 1176JZ(F)-S v1.O™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some examples, multiple processors or processors with multiple cores can also be used, whether in a single computer system, in a cluster, or distributed across systems over a network comprising a plurality of computers, cell phones, and/or personal data assistant devices.

As illustrated in FIG. 8, a high-speed cache 804 can be connected to, or incorporated in, the processor 802 to provide a high-speed memory for instructions or data that have been recently, or are frequently, used by processor 802. The processor 802 is connected to a north bridge 806 by a processor bus 808. The north bridge 806 is connected to random access memory (RAM) 810 by a memory bus 812 and manages access to the RAM 810 by the processor 802. The north bridge 806 is also connected to a south bridge 814 by a chipset bus 816. The south bridge 814 is, in turn, connected to a peripheral bus 818. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 818. In some alternative architectures, the functionality of the north bridge can be incorporated into the processor instead of using a separate north bridge chip.

In some examples, system 800 can include an accelerator card 822 attached to the peripheral bus 818. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 824 and can be loaded into RAM 810 and/or cache 804 for use by the processor. The system 800 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with the present disclosure.

In this example, system 800 also includes network interface cards (NICs) 820 and 821 connected to the peripheral bus for providing network interfaces to external storage, such as Network Attached Storage (NAS) and other computer systems that can be used for distributed parallel processing.

Figure 9:
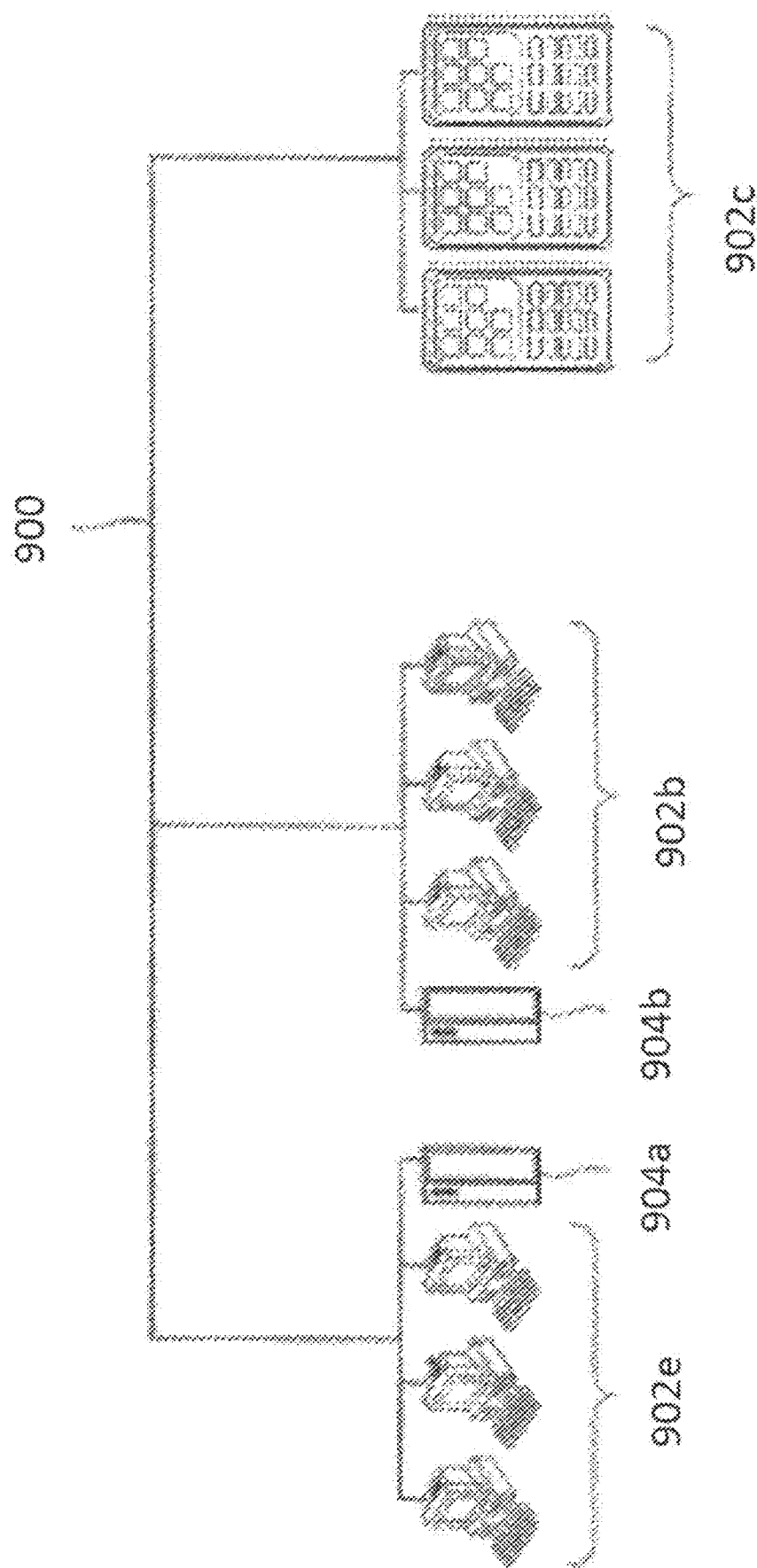
FIG. 9. A schematic of a computer system which may be used with the methods and systems disclosed herein, according to certain embodiments.

FIG. 9 is a diagram showing a network 900 with a plurality of computer systems 902*a*, and 902*b*, a plurality of cell phones and personal data assistants 902*c*, and Network Attached Storage (NAS) 904*a*, and 904*b*. In some examples, systems 902*a*, 902*b*, and 902*e* can manage data storage and optimize data access for data stored in Network Attached Storage (NAS) 904*a* and 904*b*. A mathematical model can be used for the data and be evaluated using distributed parallel processing across computer systems 902*a*, and 902*b*, and cell phone and personal data assistant systems 902*c*. Computer systems 902*a*, and 902*b*, and cell phone and personal data assistant systems 902*c* can also provide parallel processing for adaptive data restructuring of the data stored in Network Attached Storage (NAS) 904*a* and 904*b*. FIG. 9 illustrates an example only, and a wide variety of other computer architectures and systems can be used in conjunction with the various examples of the present invention. For example, a blade server can be used to provide parallel processing. Processor blades can be connected through a back plane to provide parallel processing. Storage can also be connected to the back plane or as Network Attached Storage (NAS) through a separate network interface.

In some examples, processors can maintain separate memory spaces and transmit data through network interfaces, back plane or other connectors for parallel processing by other processors. In other examples, some or all of the processors can use a shared virtual address memory space.

The above computer architectures and systems are examples only, and a wide variety of other computer, cell phone, and personal data assistant architectures and systems can be used in connection with example examples, including systems using any combination of general processors, co-processors, FPGAs and other programmable logic devices, system on chips (SOCs), application specific integrated circuits (ASICs), and other processing and logic elements. In some examples, all or part of the computer system can be implemented in software or hardware. Any variety of data storage media can be used in connection with example examples, including random access memory, hard drives, flash memory, tape drives, disk arrays, Network Attached Storage (NAS) and other local or distributed data storage devices and systems.

Angiography (imaging of blood vessels) is of crucial importance to a wide range of diseases, including carcinogenesis, atherosclerosis, inflammatory processes, diabetic retinopathy, and neurodegenerative diseases. However, prior angiography techniques rely on blood flow for contrast or use intravenous contrast agents and harmful radiation. These techniques are problematic because sample motion or slow blood flow rates can significantly degrade vessel contrast or entirely remove an ability to see the blood vessels. Additionally, contrast agents can produce problems in some patients. Certain examples solve these problems by providing SC-OCTA to reveal blood vessel and lymphatic vessel location all the way down to the capillary level with endogenous absorption contrast without relying on flow.

Certain examples enable screening for vascular disease, vessel occlusion, disease associated with vasculature alteration, etc. Without using a dye or contrast agent, blood vessel diagnostic can be performed to facilitate treatment at particular blood vessel location(s), regardless of whether blood is flowing. Certain examples provide single scan optical coherence tomography angiography. Certain examples provide lymphatic and blood vessel discrimination based on the SC-OCTA data. Certain examples provide imaging of vessels with endogenous contrast. Certain examples provide imaging of blood vessels without flow (e.g., can be performed on biopsied tissue with no dies or preparation, etc.). Certain examples provide imaging of slow flow velocity blood vessels, such as capillaries, occluded vessels, and lymphatics with endogenous contrast.

Certain examples change how OCT endoscopes are configured and reduce cost to build an OCT machine as well as enable both disposable and reusable probe components.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

Example 1: Exemplary Embodiments

1. A method of blood vessel location using spectral contrast optical coherence tomography angiography.

2. A system to measure blood vessel location using spectral contrast optical coherence tomography angiography.

3. A computer-readable storage medium including instructions which, when executed, cause a processor to at least determine blood vessel location using spectral contrast optical coherence tomography angiography.

4. A spectral contrast optical coherence tomography angiography apparatus.

5. An optical coherence tomography endoscope in communication with a spectral contrast optical coherency tomography angiography system.

6. A method of blood imaging in a target using spectral contrast optical coherence tomography angiography.

Example 2: Additional Embodiments

SD-OCT obtains depth-resolved sample information by taking a Fourier transform of the interference recorded as a function of wavelength (on a spectrometer) between a reference reflection and light scattered from the sample (FIG. 1A). By subsampling the spectrum with a short time Fourier transform (STFT), spectrally dependent OCT A-lines are measured. Therefore, opposite spectral slopes of blood and tissue can be spatially visualized by looking at the contrast of spectrally dependent OCT image intensities from 550 nm to 600 nm. A Kaiser sampling window at 557 nm and 620 nm with a full width at half maximum (FWHM) of ~38 nm provides high spectral contrast between blood and the surrounding tissue.

In vivo B-scans (FIG. 1B) of lower human labial mucosa (inner side of lip) can be seen with the ratio of the OCT image intensities from the two Kaiser windows (620 nm divided by 557 nm), hereafter referred to as SC-OCTA. In images from the inverse OCT intensity at 557 nm, hereafter referred to as inverse 557 nm images, blood vessels can easily be seen due to the high contrast and high absorption provided in the visible range. The spectral contrast image demonstrates how blood vessels are highlighted by a shadow and tissue is ignored. To confirm capillary imaging, inverse 557 nm and SC-OCTA en face projections were compared with the results of traditional OCTA phase and amplitude contrast (FIG. 1C). The same eight capillary loops in the labial mucosa are seen in the inverse 557 nm image, SC-OCTA, as well as in the traditional OCT angiography, which requires the sample to be scanned at least twice. It took 18.2 sec to acquire the traditional OCTA data and an effective 4.5 sec for SC-OCTA data. A detailed large field of view of the labial mucosa (FIGS. 1D-1E) demonstrates the ability of SC-OCTA to resolve arteriolar and capillary-level vessels (FIGS. 10A-10C) with only a single A-line acquired at each point-scanning location. The inverse 557 nm image does not differentiate low scattering structures from hemoglobin absorption. This is noted by the white arrow showing a salivary duct that is visible in the inverse 557 nm image (FIG. 1D) but not in the SC-OCTA image (FIG. 1E).

Figure 13:
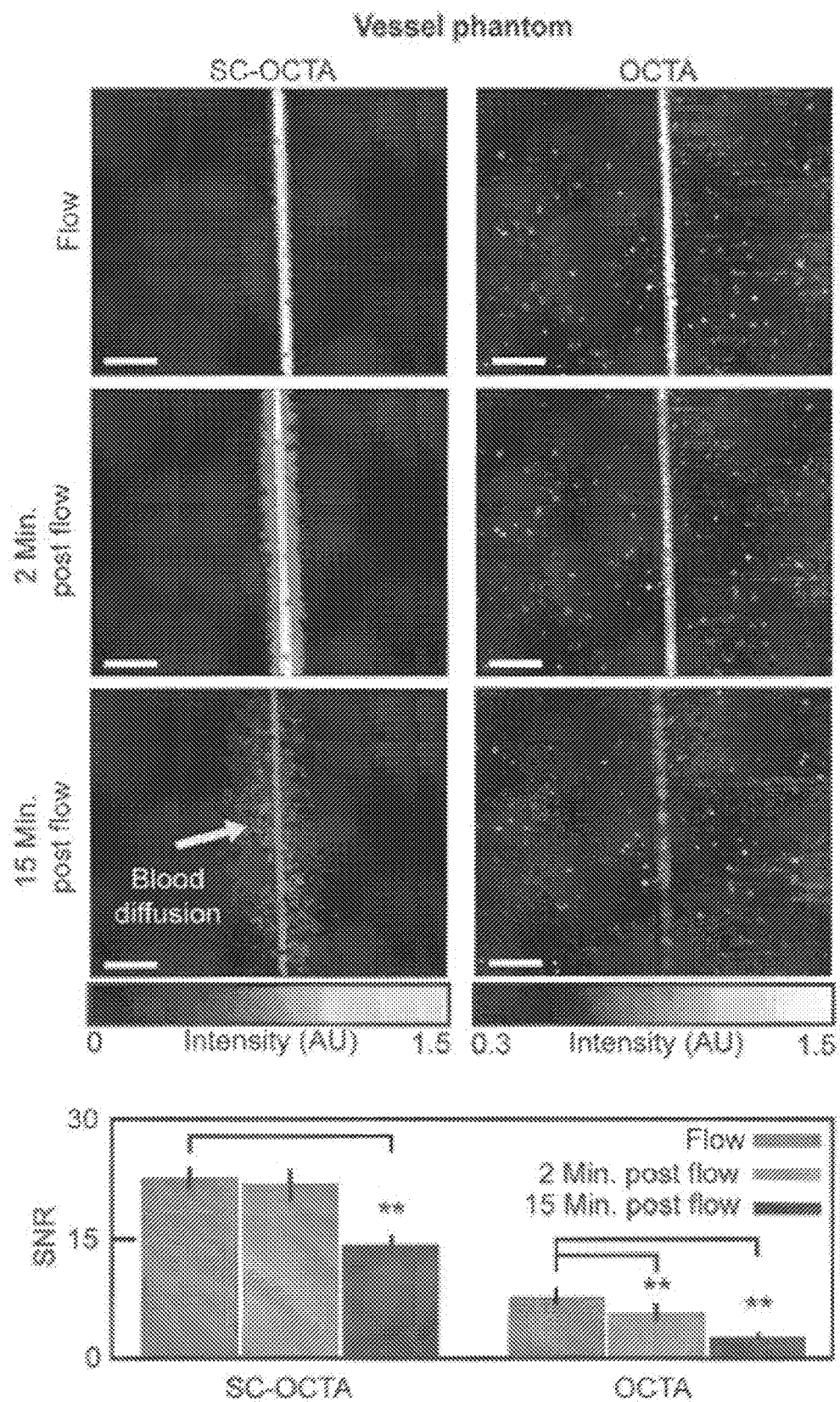
FIG. 13. Vessel phantom imaging using bovine blood. En face projections of SC-OCTA and OCTA under different flow conditions and the corresponding signal-to-noise ratio (SNR). Due to the dynamic nature of the agarose-based phantom, SC-OCTA measurements were taken from one of the repetitions of the OCTA scan to ensure similar measurement conditions. SC-OCTA (flow: 22.76±1.42; 2 min post flow: 21.99±1.95; 15 min post flow: 14.08±1.30). OCTA (flow: 7.69±1.13; 2 min post flow: 5.74±1.21; 15 min post flow: 2.35±0.60). ** (p<0.01) for the two-sample t-test. The standard deviation is taken over 10 equally sized regions across the phantom (FIG. 11F). Scale bar: 250 µm. During the flow measurement, a syringe pump supplying blood to the phantom was set to 0.0006 µL/sec. Measurements were then taken 2 min and 15 min after stopping the flow to the phantom. It can be seen that SC-OCTA SNR is not significantly affected 2 min after stopping the flow, and SC-OCTA can visualize blood diffusing into the vessel phantom (FIG. 11A) not seen by OCTA. The SNR is significantly affected 15 min post flow in SC-OCTA due to decrease in the blood concentration in the vessel channel. The SNR was computed from the raw en face projection intensities, while the images of the en face projections were scaled to minimize their background intensities.
Figure 14A:
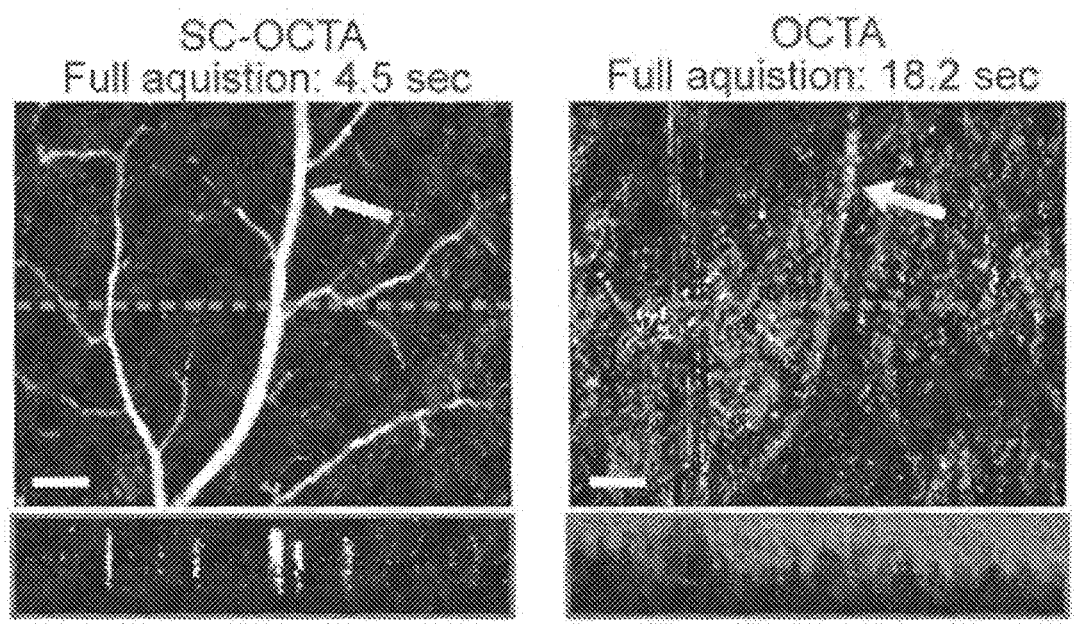
FIGS. 14A-14B. Sacrificed mouse hemostasis imaging of serosal surface of large intestines.
Figure 14B:
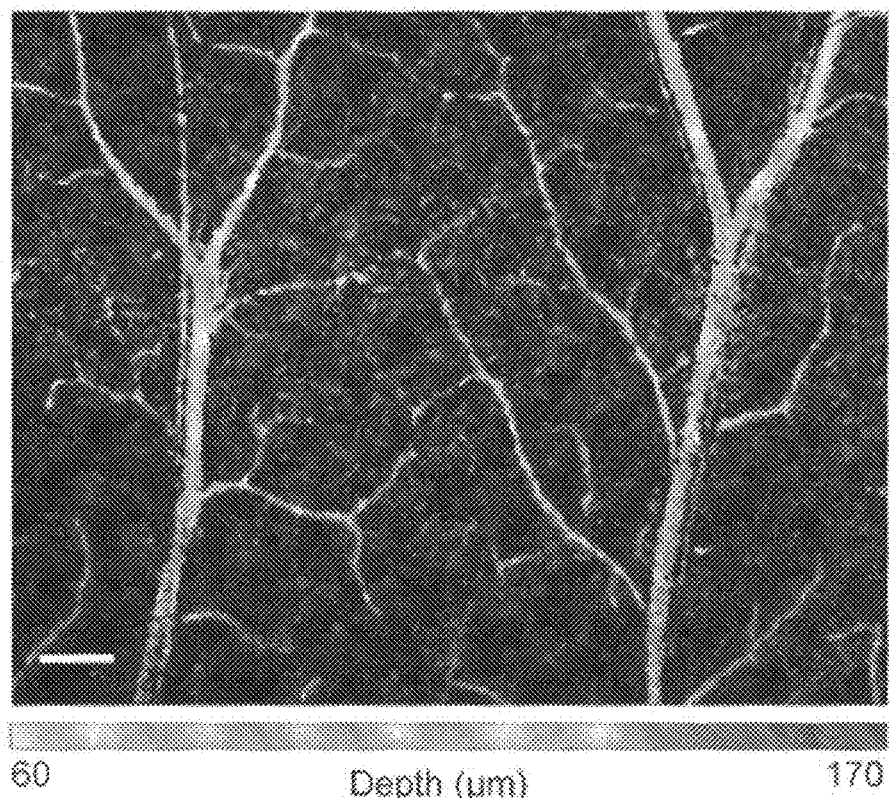
Figure 15A:
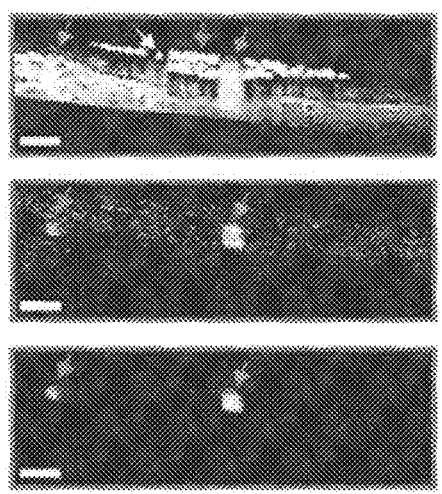
Figure 15B:
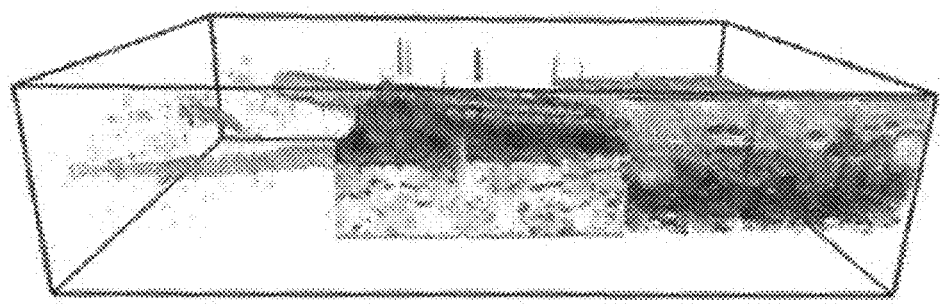

Because SC-OCTA does not rely on motion for contrast, it can image nonflowing blood and highly moving samples. To demonstrate this capability, a ~55 µm diameter vessel phantom (FIGS. 11A-11B) is fabricated and the signal-to-noise ratio (SNR) of the SC-OCTA and OCTA signals is recorded under different flow conditions (FIG. 13) and vibrations (FIGS. 11D-11E). The results showed that in contrast to OCTA, the SC-OCTA signal is not significantly affected by flow and can image highly moving samples. With a limited vessel phantom lifetime, waiting for blood turbulence to approach zero was not possible. Therefore, to demonstrate the utility of SC-OCTA in the hemostasis setting, the serosal surface of a freshly sacrificed mouse large intestine was imaged (FIGS. 14A-14B). To the best of our knowledge, this is the first time angiography has been performed on tissue with nonmoving blood with endogenous contrast using OCT. The results show that OCTA struggles to resolve any vessels in the hemostasis setting, while SC-OCTA can detect several vessels with a faster acquisition time (FIG. 14A). To demonstrate the molecular sensitivity of SC-OCTA, lymphatics and blood vessels were imaged on a freshly sacrificed mouse omentum (FIGS. 15A-15O) and a heart surface, where images were compared with histological imaging of the same tissue (FIGS. 15E-15G). Notably, SC-OCTA differentiates blood vessels from low-scattering lymphatic vessels and adipocytes. A B-scan of depth-integrated SC-OCTA, where each pixel in the SC-OCTA image is integrated 50 µm along the depth and multiplied by the inverse 557 nm image, allowed vessels to be represented in three dimensions (FIGS. 15A-15G). Depth-integrated SC-OCTA demonstrated the ability to image the branches of the coronary arteries and differentiate these from neighboring lymphatic vessels (FIG. 15E). The high resolution and contrast in the visible spectrum additionally allowed imaging of lymphatic valves where the tricuspid structure of the valve is easily discerned in three dimensions (FIG. 15D).

Figure 16:
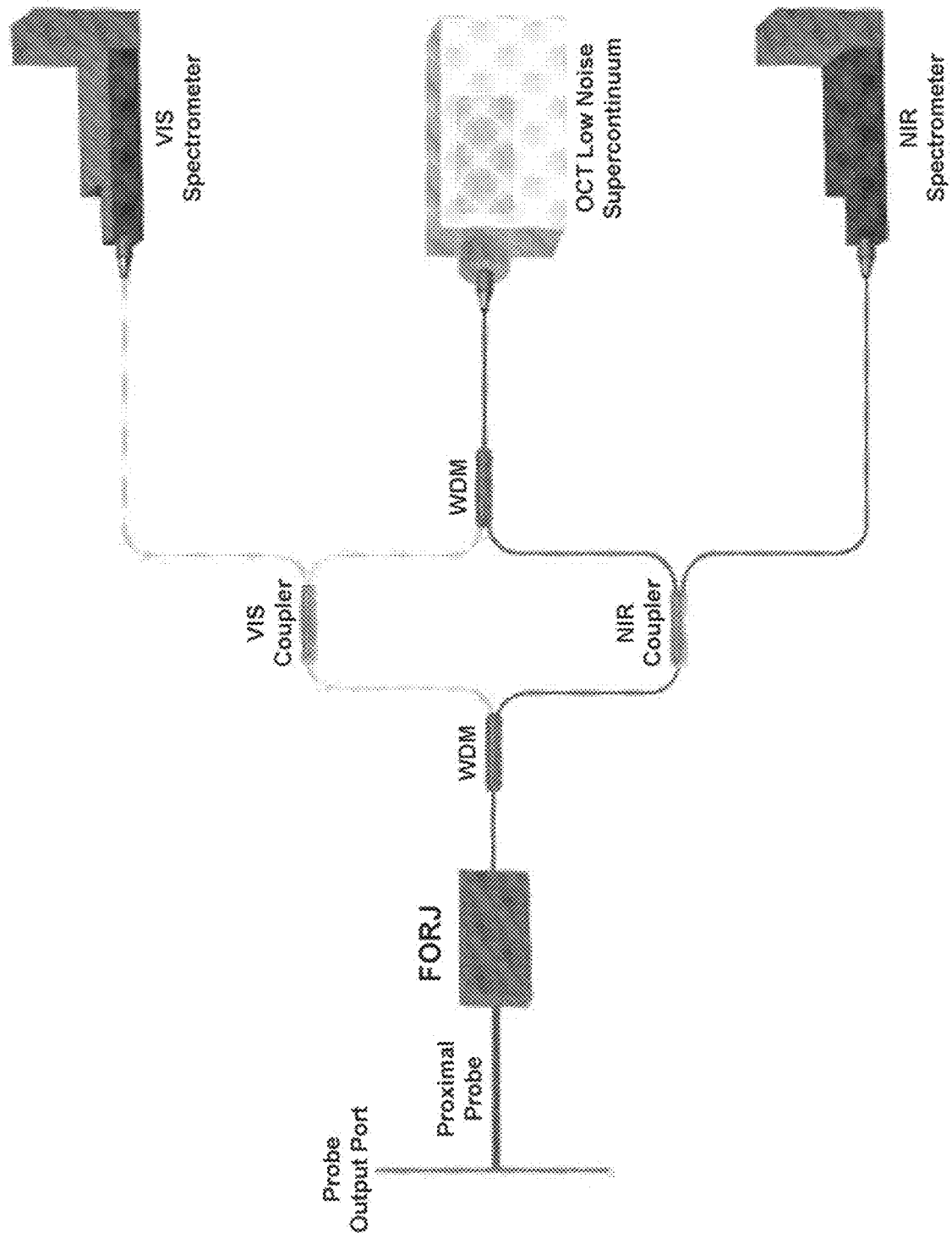
FIG. 16. Fiber schematic layout for endoscope system. VIS Spectrometer (510-635 nm). NIR Spectrometer (700-850 nm). FORJ (Fiber Optic Rotary Joint, see FIG. 17) allows single mode operation over 500-850 nm by using antireflective coated C-lenses. The FORJ translates circumferential scanning to the distal end of the probe with a torque cable and uses a translational stage to achieve pull-back scanning. WDM (Wavelength Division multiplexor) splits light into NIR (700-850 nm) and Visible (510-635 nm) bands. The infrared allows for deeper spectroscopic measurements and calculation of blood oxygenation and flow from deep large vessels while the visible allows for shallow spectroscopic measurements with SC-OCTA and blood oxygenation of smaller vasculature.
Figure 17:
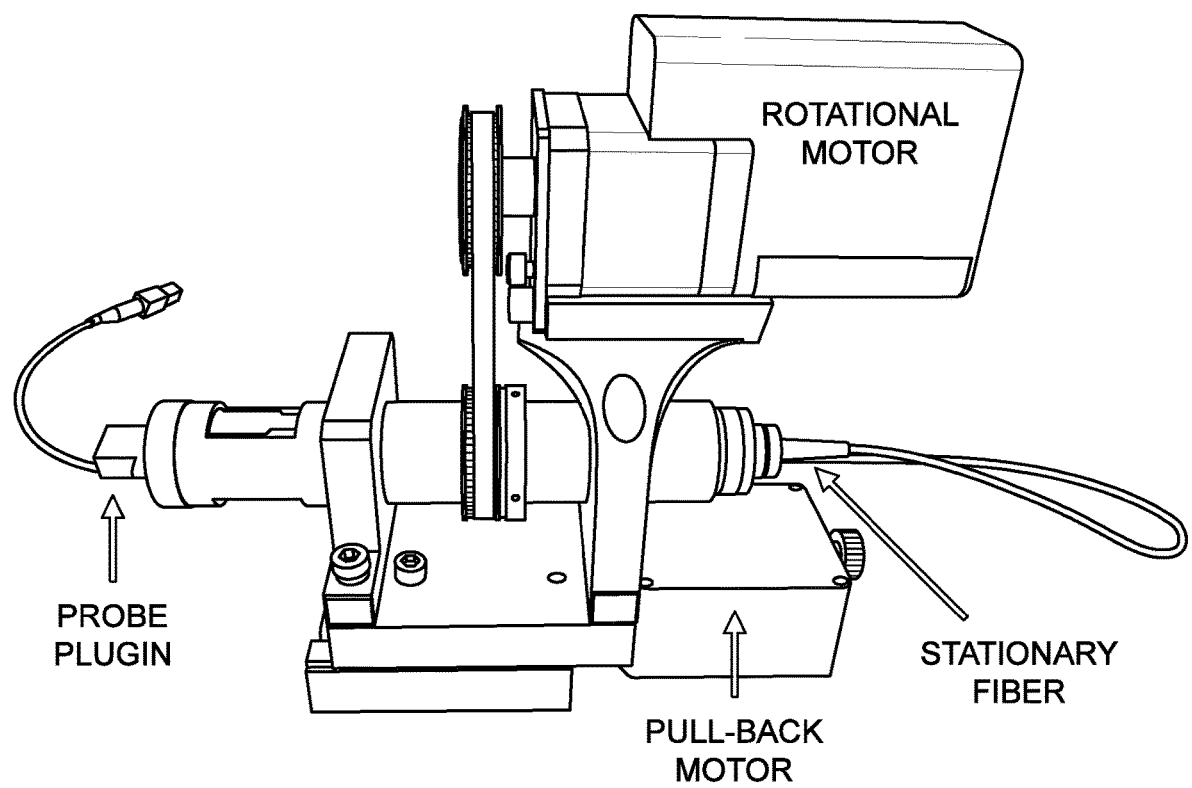
FIG. 17. Picture of the single mode broadband fiber optic rotary joint which allows for operation over 500-850 nm. The rotary joint consists of antireflective coated C-lenses and SM600 single mode fiber. A stepper motor (Rational Motor) allows for translation of rotation to the distal end of the endoscope with a torque cable and another stepper motor allows for pull-back (Pull-Back Motor).
Figure 18:
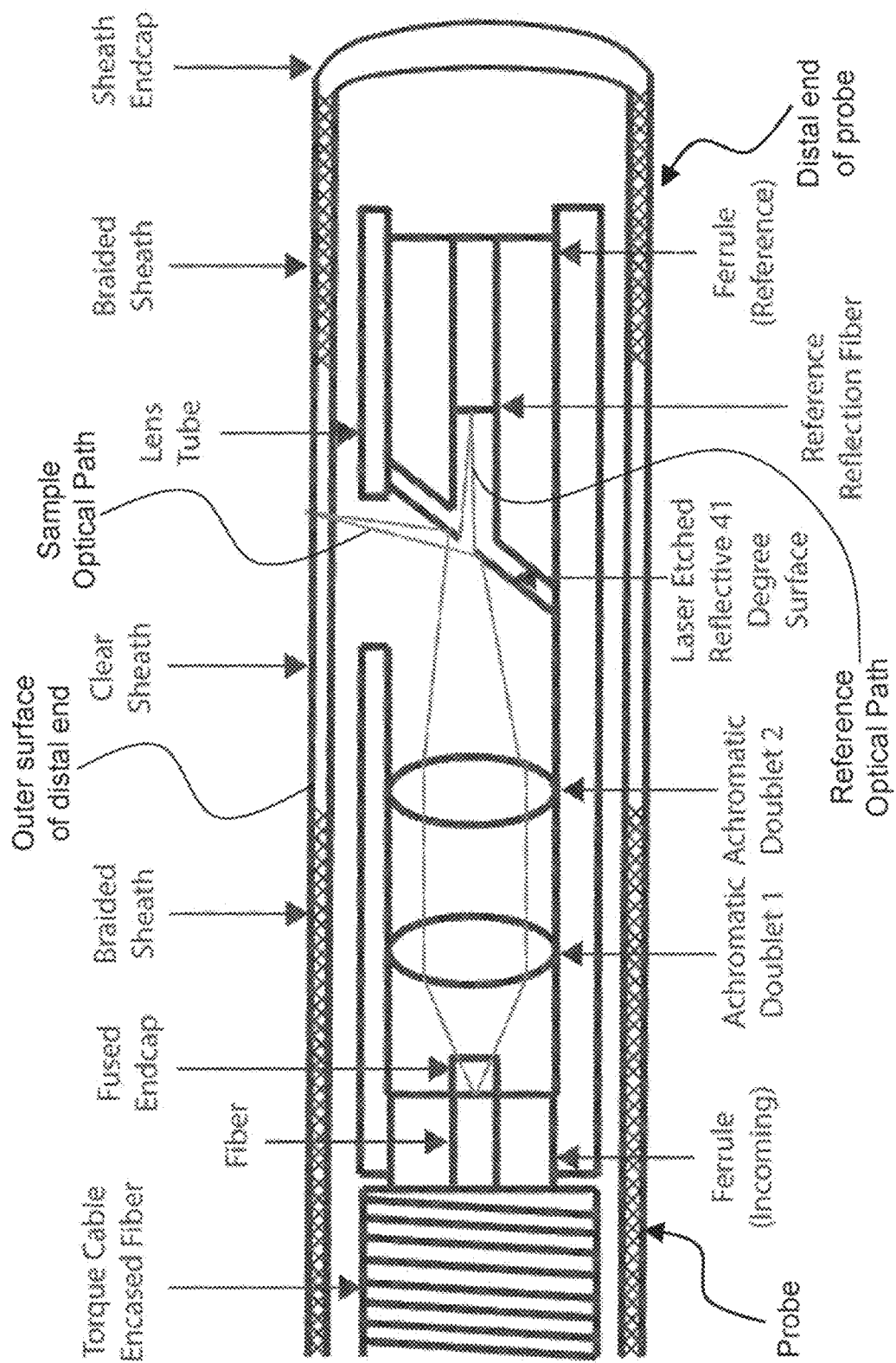
FIG. 18. Endoscope compatible OCT probe. Thin lines in the center indicate light path. The probe uses an occlusion mechanical beam splitter design to eliminate fiber bending polarization effects on interference efficiency allowing for spectroscopic OCT measurements to be carried out in flexible probe. If a separate reference arm is used the endoscope will experience varying interference efficiency as the fiber going to the probe bends making spectral calibrations no longer valid. A torque cable translates rotation from the fiber optic rotary joint to the distal end of the probe. The fiber delivering light to the probe has a fused coreless fiber endcap that is antireflective coated to eliminate return loss. Achromatic doublet 1 (Focal Length=1.5 mm) collimates the beam and achromatic doublet 2 (Focal Length=3 mm) focuses the beam onto the sample and reference reflection. The achromatic doublets allow the beam to achieve minimal axial chromatic aberration compared to GRIN lenses. The laser etched reflective surface directs a portion of the beam to the sample and the rest of the beam to a cleaved fiber for a reference reflection. The surface was created by first polishing a ferrule to 41 degrees, epoxying a laser etched C50 micron occlusion) cover slip onto the surface (See FIGS. 19A-19B), and then e-beam coating the surface with aluminum. The bore in the ferrule could not be used because it was too large. The reflective surface was 41 degrees to prevent collection of reflection off the outer sheath. A brass machined tube (1.5 mm outer diameter) encloses the optics. A stationary sheath (2 mm outer diameter) encases the torque cable and probe from biological fluids. The sheath is only 200 microns thick, so in order to prevent kinking the sheath is braided. A portion of the sheath ~5 mm in length is unbraided to allow the beam going to the sample to not be blocked.
Figure 19A:
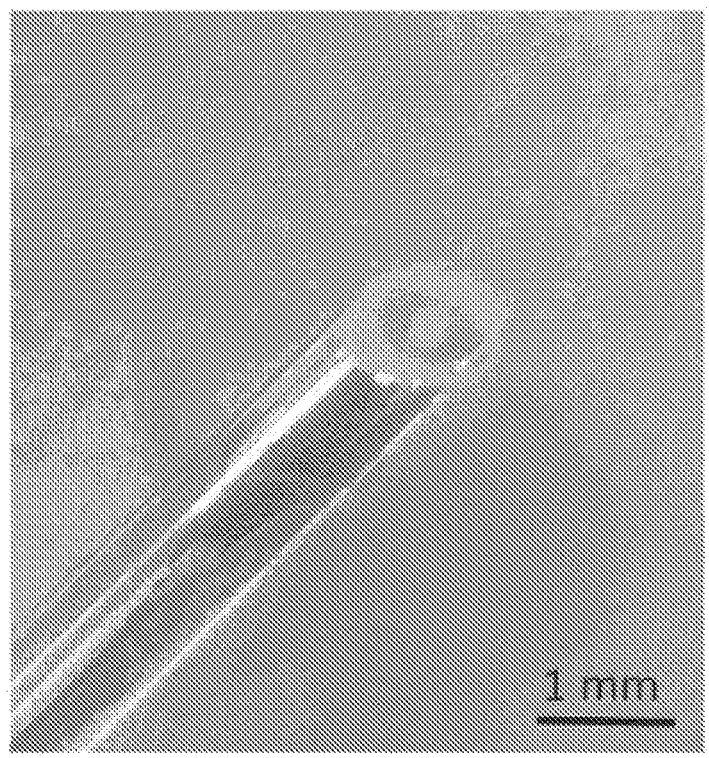
FIGS. 19A-19B. Creation of occlusion mechanical beam splitter for probe.
Figure 19B:
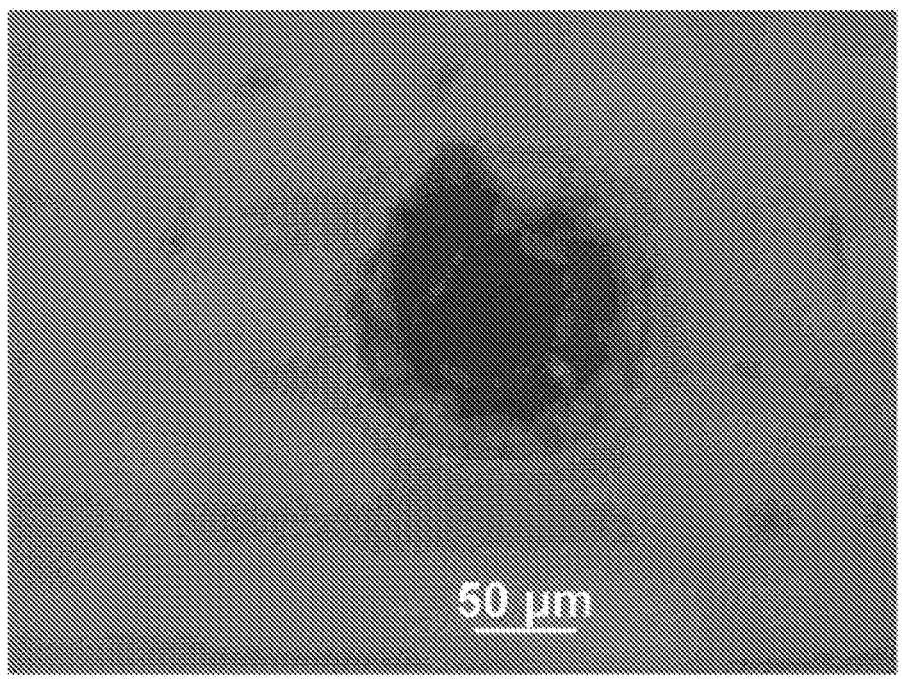
Figure 20:
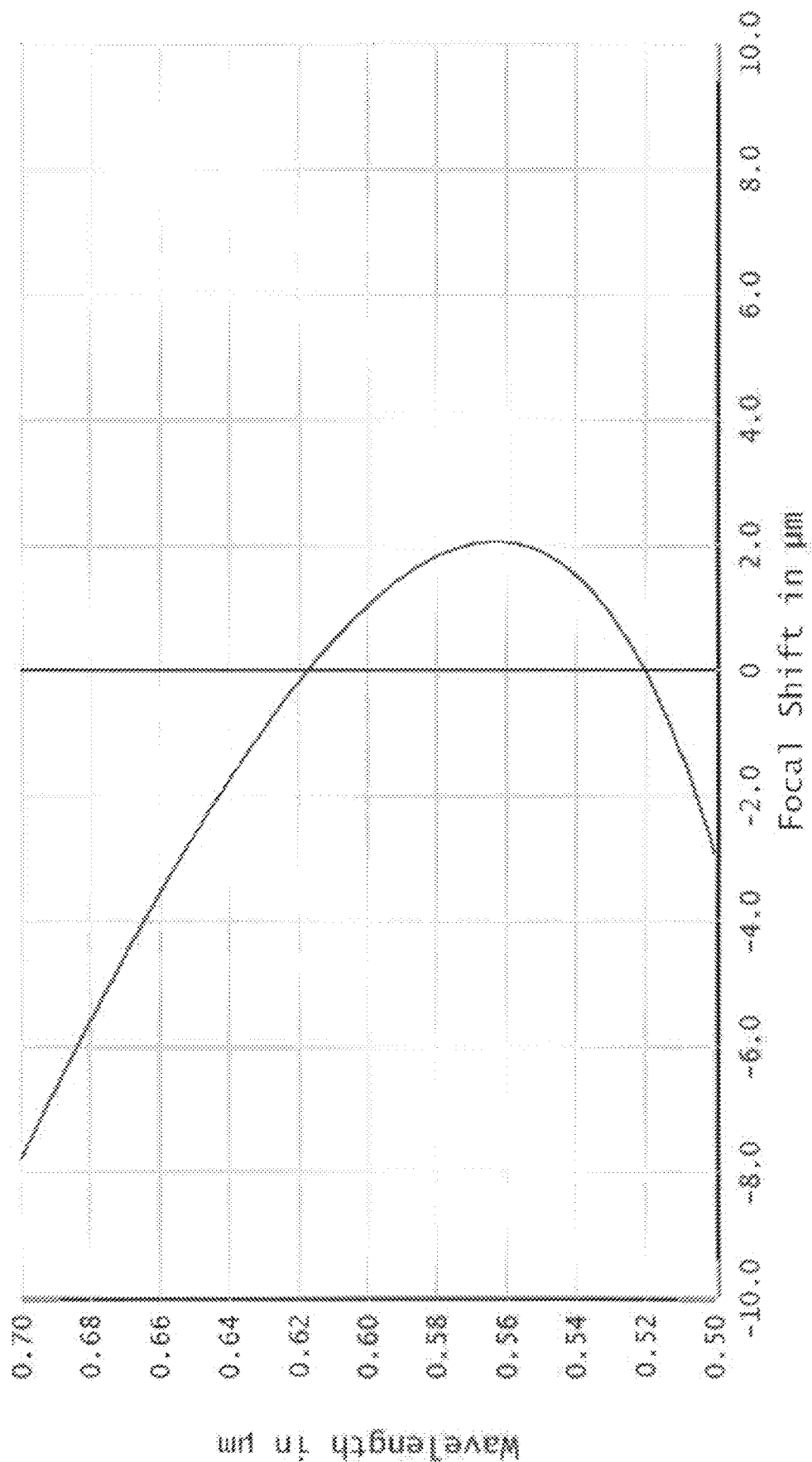
FIG. 20. Axial chromatic focal shift estimate using Zemax optical modeling software for the design shown in FIG. 18. The maximum focal shift from 500-700 nm is estimated to be 9.84 microns.
Figure 21:
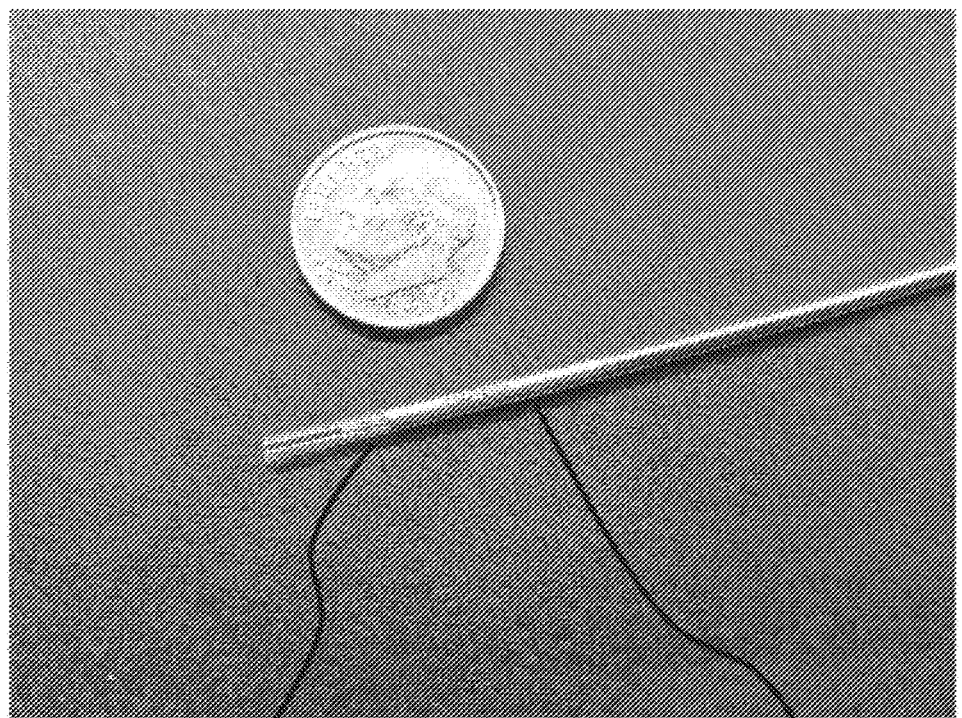
FIG. 21. Prototype of 2 mm OD OCT probe using design shown in FIG. 18.

To allow for endoscopic spectroscopic OCT measurements (including SC-OCTA, blood oxygenation and tissue spectral analysis), a flexible endoscopic compatible probe is needed. System spectral intensity calibration is a necessary step in performing spectroscopic OCT of a sample. In probe layouts where a separate reference arm is used, bending of the fiber going to the endoscope will cause changes to polarization between the reference and sample arm. Polarization changes will cause changes to interference efficiency across the spectrum and must be accounted for to maintain a valid system spectral intensity calibration for spectroscopic OCT measurements. For example, tissue spectra should have a monotonic decay. However, if the probe fiber bends and reduces the interference efficiency at shorter wavelengths and not at longer wavelengths this could lead to a recorded tissue spectrum of monotonic increase instead of decrease. The probe system layout in FIG. 16 and distal probe optical design FIG. 18 addresses the fiber bending issue by performing interferometry in the probe. A mechanical occlusion beam splitter is used inside the distal end of the probe that allows interference efficiency to not be affected by fiber bending since the reference arm and sample arm are in the same fiber path. Unlike thin film beam splitters, the mechanical occlusion design should not be sensitive to polarization or vary across wavelength. Furthermore, the achromatic doublet design drastically minimizes chromatic focal shift (see FIG. 20) compared to GRIN lenses. The design also allows for simultaneous visible (510-635 nm) and near infrared light (700-850 nm) for deep spectroscopic measurements. This should allow for the novel ability to perform doppler and blood oxygenation measurements of large vessels (>~50 micron) using 700-850 nm light.

Example 3: Exemplary Embodiments

1. A method of blood vessel location using spectral contrast optical coherence tomography angiography.
2. A system to measure blood vessel location using spectral contrast optical coherence tomography angiography.
3. A computer-readable storage medium including instructions which, when executed, cause a processor to at least determine blood vessel location using spectral contrast optical coherence tomography angiography.
4. A spectral contrast optical coherence tomography angiography apparatus.
5. An optical coherence tomography endoscope in communication with a spectral contrast optical coherency tomography angiography system.
6. A method of blood imaging in a target using spectral contrast optical coherence tomography angiography.
7. A method of doing flexible spectroscopic OCT probe measurements.
8. A method of doing simultaneous visible and near infrared band flexible OCT probe measurements.

Example 4: Theoretical Estimation of SC-OCTA SNR

A macroscopic simulation based on the single scattering response is developed to numerically consider the contrast limits of the SC-OCTA signal with tissue noise and noise of systems disclosed herein, according to certain embodiments. The OCT backscattered intensity can simplified with the following analytical expression:

$$I^2(x, y, z, k) = rLI_0^2(x, y, z, k)\frac{\mu_b(x, y, z, k)}{4\pi}\exp(-2\mu_t(x, y, z, k)) \quad (S1)$$

where r is the reflectance of the reference arm, L is the temporal coherence length of the source, $I_0$ is the incoming beam intensity, $\mu_b$ is the backscattering spectra, $\mu_t$ is the attenuation coefficient, k is the wavenumber in free space and z is the depth position in the sample. First, the geometry of the sample is established; for this simulation, a cylindrical tube of blood with varying diameters is considered, positioned 70 μm below the surface and embedded in tissue. Each A-line is separated into its homogenous regions (tissue/blood/tissue) and the above expression is evaluated for each region, with its incoming intensity ($I_0$) modulated by the media above it, eg. reflecting with backscattered spectra at the interface and decaying within homogenous regions according to equation S1. This is repeated until the entire volumetric scattering intensity I(x, y, z, k) was computed. The backscattering coefficient of tissue is assumed to have a power law $k^{(4-D)}$ relationship, using a D of 2.1. The absolute backscattering spectrum at each interface (tissue/air and tissue/blood) is normalized to yield a mean Fresnel reflection coefficient between their respective boundaries. The attenuation coefficient of tissue is taken from published healthy colon mucosal tissue, and the attenuation coefficient of whole oxygenated blood was taken from literature averaged values. It is then considered that the optical properties of a single RBC can be approximated by a volume equivalent bead of 3 μm with refractive index matching that of oxygenated hemoglobin and background of tissue (refractive index=1.38), and computed by Mie theory.

Then the structural variation of tissue is considered. It is taken in constant in wavelength, normally distributed, and can be represented as a constant scaling of the backscattered intensity. Then the structural variation of the OCT image is computed for labial mucosal tissue over 440×440×150 μm area after a log transform. The mean normalized distribution has a standard deviation of 0.7; eg. Standard Deviation[log (Img3D)]/Mean[log(Img3D)]. A normally distributed random variable is added to the intensity I(x,y,z,k) with said standard deviation. The SC-OCTA signal is then generated according to (3). Next, the system noise is added to the SC-OCTA signal, which is quantified in FIG. 23D, as a Gaussian distribution with a standard deviation of 0.03. This allows for simulated SC-OCTA B-scans to be generated. An example of a simulated SC-OCTA B-scan with a 20 μm diameter vessel in tissue can be seen in FIG. 22A.

Figure 22B:
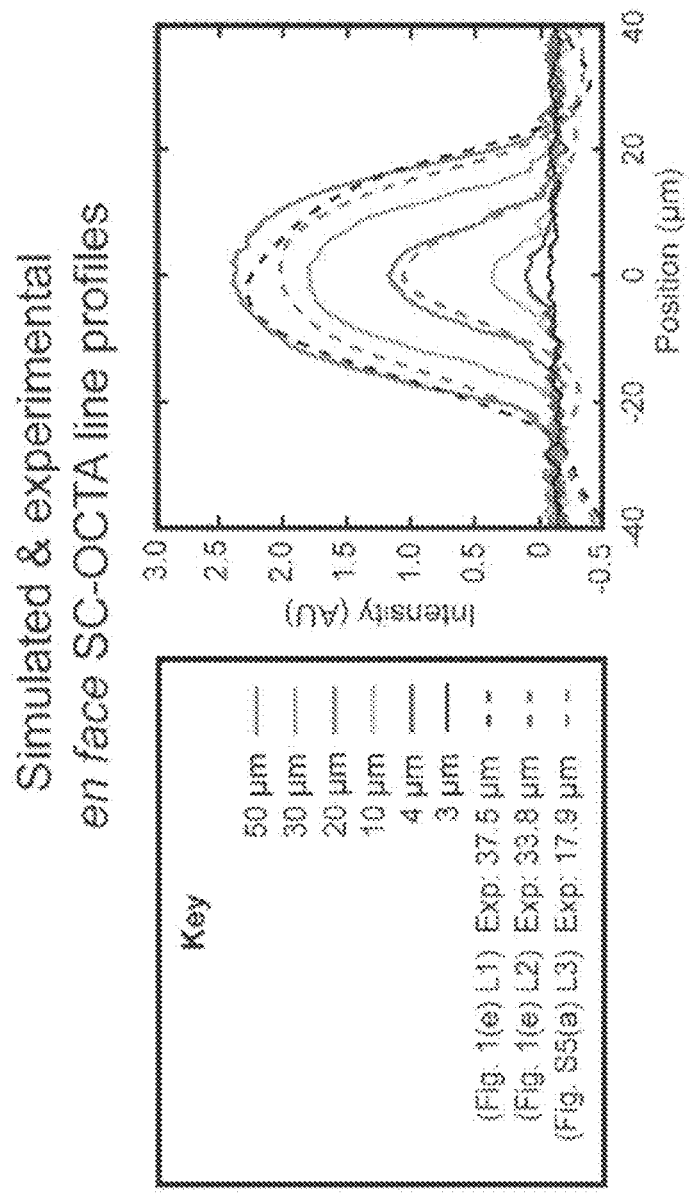
FIGS. 22A-22B. Macroscopic SC-OCTA simulation.

From the simulated SC-OCTA B-scans, en face projections are generated over 140 μm in depth and quantified the en face vessel line profiles which are shown in FIG. 22B for various sizes. The 3 μm and 4 μm were generated using Mie theory, while the 10-50 μm diameter vessels assumed the optical response of whole blood. Furthermore, experimentally measured line profiles (L1-L3) from FIG. 1E and FIG. 10A are included. The line intensities of L1-L3 were fitted with a Gaussian curve to measure the FWHM, which is listed in the legend of FIG. 22B.

Based on the contrast of $\mu_b$ and $\mu_t$, it is evident that the SC-OCTA technique shows contrast for a single cell assuming the properties of a 4 μm bead and thus single capillary depending on the refractive index contrast, surrounding tissue fluctuations, and depth of integration. The floor of the line profile is characterized by the slope of the background tissue (e.g., smaller D, can result in a steeper decaying $\mu_b$ and more negative background SC-OCTA signal). The optimal threshold for distinguishing vessel from tissue can be optimized based on the tissue type. Furthermore, SNR is sensitive to the homogeneity of the tissue and the refractive index contrast between the blood and tissue. SC-OCTA contrast will be greater in more weakly scattering tissue. For example, if the background tissue refractive index is changed from 1.38 to 1.33, the en face 4 μm bead intensity doubles. Finally, it should be noted, that like all OCT imaging techniques, vessel response can decrease with depth into the sample due to system sensitivity roll-off, focusing and sample light attenuation.

Figure 22A:
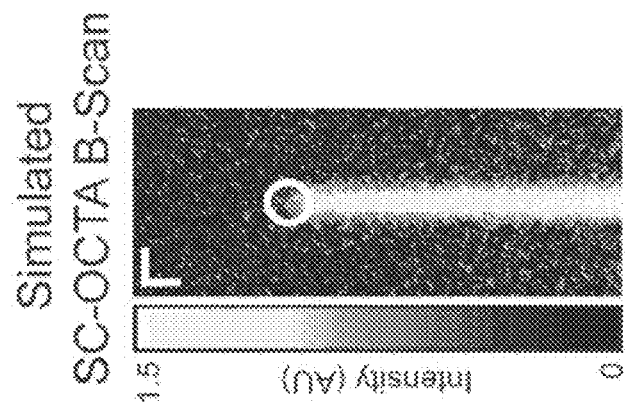
Figure 23A:
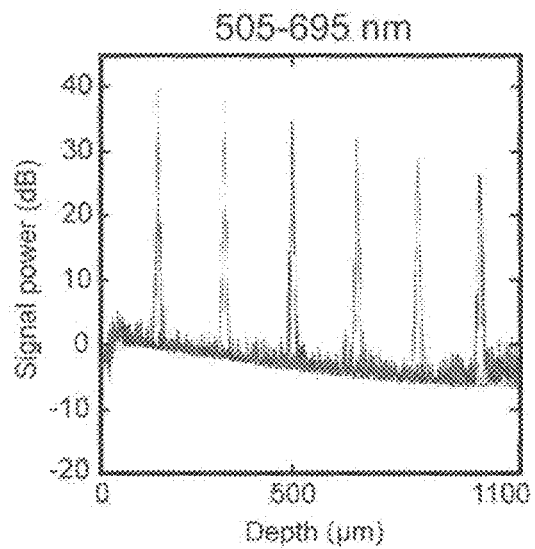
FIGS. 23A-23D. Systems sensitivity measurements. The impulse response function of a mirror placed in the sample arm. The reference mirror position was changed to record the impulse response functions at different path lengths (depths) in air. These measurements should not be confused with system performance into different depths of a tissue sample, which has the added elements of sample optical attenuation properties and the axial point spread function of the focusing objective. Measurements were the average over 500 A-lines with a total round-trip attenuation in the sample arm of 51.4 dB using a neutral density filter.
Figure 23B:
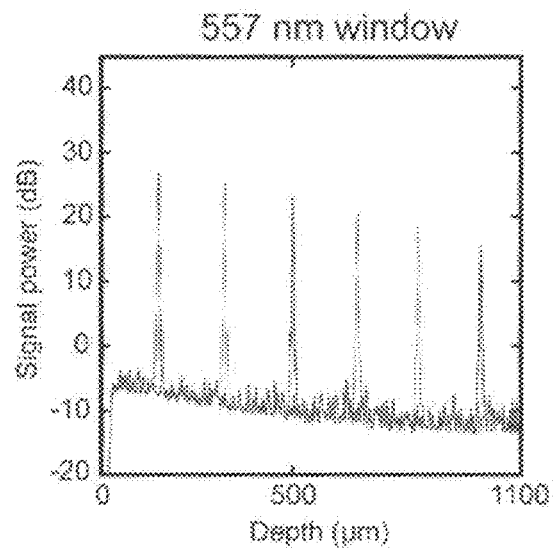
Figure 23C:
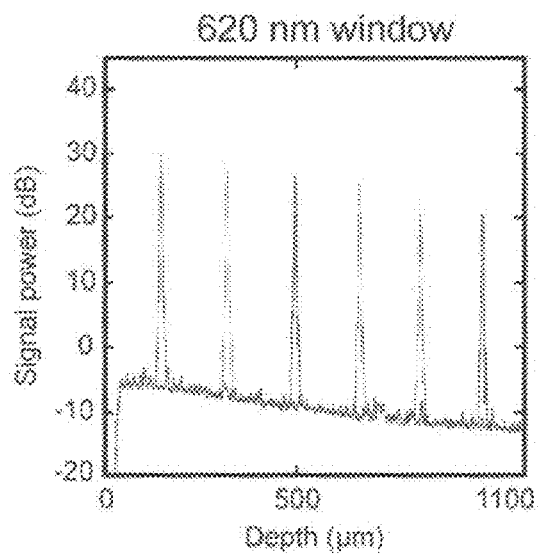
Figure 23D:
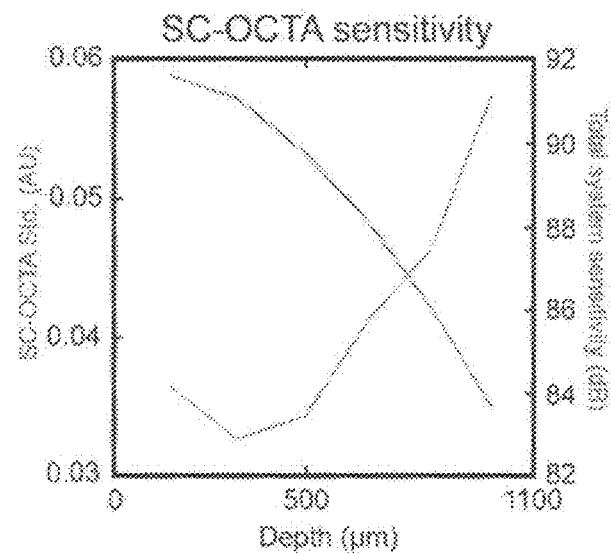
Figure 24A:
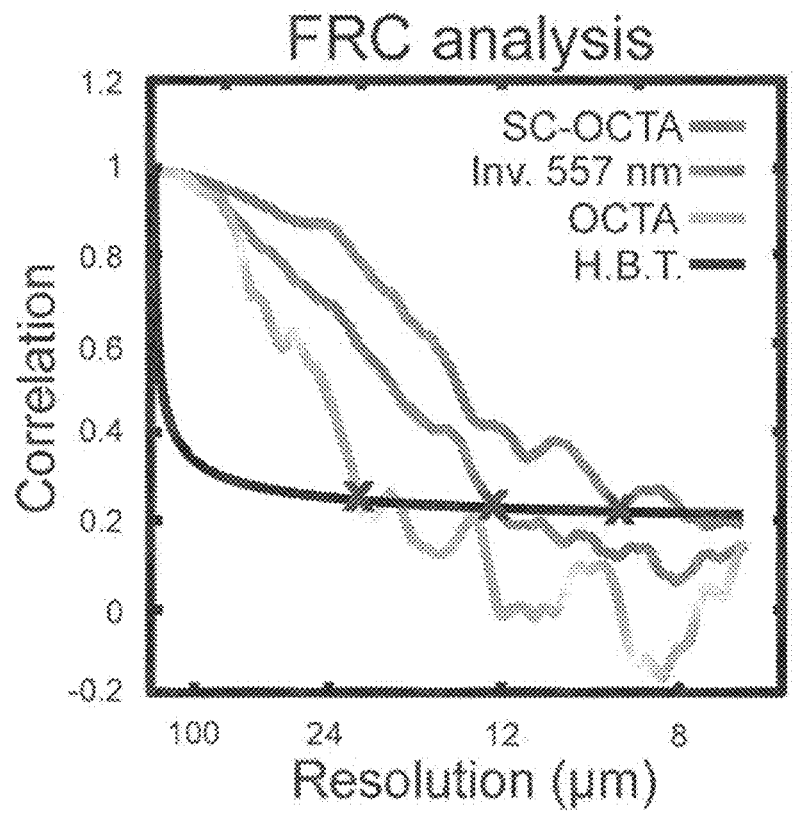
FIGS. 24A-24B. Fourier Ring Correlation of the field of view in FIG. 1C for SC-OCTA, inverse 557 nm, and traditional OCTA. H.B.T (Half-bit threshold). The Fourier Ring Correlation (FRC) allows one to determine which feature sizes or spatial frequencies are conserved between subsequent measurements and which are attributed to noise by computing the Fourier correlation between successive data sets. For this analysis two images from OCTA, inverse 557 nm, and SC-OCTA were generated. For OCTA, the angiography signal produced from two subsequent frames (frame 2 and 3 for one image, and frame 3 and 4 for another) is used, not four subsequent frames like the rest of the OCTA images shown in this letter. For the inverse 556 nm and SC-OCTA images repetitions 2 and 4 are used. Each pair of images are processed using the published FRC algorithm, and the crossing of the FRC curves with the half-bit threshold (each 'x' on graph) is used to calculate the effective resolution of 20.19, 12.20, and 8.92 µm for the traditional, inverse 557 nm and SC-OCTA methods, respectively. Since the absolute diameters of the underlying vessels in that region may be unknown, this metric implicates the relative effective frequency responses of each technique in an in vivo imaging scenario.
Figure 24B:
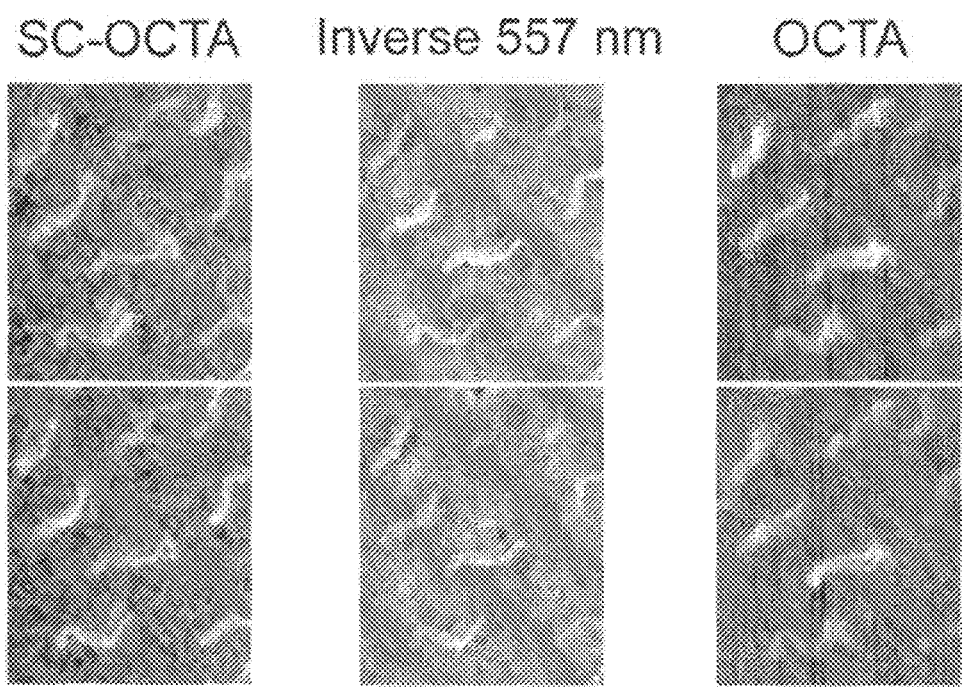

FIG. 22 corresponds to macroscopic SC-OCTA simulation. FIG. 22A shows simulated SC-OCTA B-scan image for a 20 μm diameter vessel placed at the white circle. Scale bars: 20 μm. FIG. 22B shows line profiles of simulated (solid) and experimental (dotted) en face SC-OCTA images integrated over 140 μm in depth. The experimental line profiles come from the SC-OCTA en face projections shown in FIG. 1E and FIG. 10A.

Example 5: Determination of SC-OCT Sensitivity

See FIG. 23 in association with this example, corresponding to systems sensitivity measurements. The impulse response function of a mirror placed in the sample arm. The reference mirror position was changed to record the impulse response functions at different path lengths (depths) in air. These measurements should not be confused with system performance into different depths of a tissue sample, which has the added elements of sample optical attenuation properties and the axial point spread function of the focusing objective. Measurements were the average over 500 A-lines with a total round-trip attenuation in the sample arm of 51.4 dB using a neutral density filter. (FIG. 23A) Roll-off impulse response for the total system 505-695 nm bandwidth. Roll-off sensitivity ~−10 dB/mm. Air axial resolution (1.53 μm) and sensitivity (91.61 dB) measured from the first peak. (FIG. 23B) Roll-off impulse response for the 557 nm centered Kaiser sampling window. Roll-off sensitivity ~−14 dB/mm. Air axial resolution (3.80 μm) and sensitivity (86.05 dB) measured from the first peak. (FIG. 23C) Roll-off impulse response for the 620 nm centered Kaiser sampling window. Roll-off sensitivity dB/mm. Air axial resolution (4.72 μm) and sensitivity (81.11 dB) measured from the first peak. (FIG. 23D)SC-OCTA signal standard deviation (ascending line) and total system sensitivity (descending line) measured in (FIG. 23A). The standard deviation of SC-OCTA signal was processed according to equation (3) for each mirror position over 500 A-lines. The aqueous 80 nm bead calibration was not necessary for estimation of standard deviation of SC-OCTA, and no median filters were used. The correlation between increasing system sensitivity and decreasing SC-OCTA standard deviation can be seen. The slight increase in standard deviation of SC-OCTA near the zero depth can be a result of direct current noise which can be minimized through high pass filtering the interferogram.

Example 6

As unique scanning beam locations (e.g., all surface area of region of interest are covered by at least part of incoming beam cross-sectional area) are captured and appropriate motion correction algorithms (such as Abouei et al., J Biomedical Opt. 2018) are applied, such as to allow 3D median filtering, contrast in data or images generated via the SC-OCT methods and systems disclosed herein is minimally, if at all, affected compared to the motion-sensitivity of contrast in traditional OCTA.

Example 7

Additional exemplary methods, systems, descriptions, and other embodiments, are found in Winkelmann, et al. 2018 ("Spectral Contrast Optical Coherence Tomography Angiography Enables Single-Scan Vessel Imaging," BioRxiv, published Dec. 14, 2018, https://doi.org/10.1101/406652) and Winkelmann, et al. 2019 ("Spectral contrast optical coherence tomography angiography enables single-scan vessel imaging," Light: Science & Applications, volume 8, Article number 7, published Jan. 16, 2019), each of which is incorporated herein by reference in its entirety.

Example 8

Figure 15C:
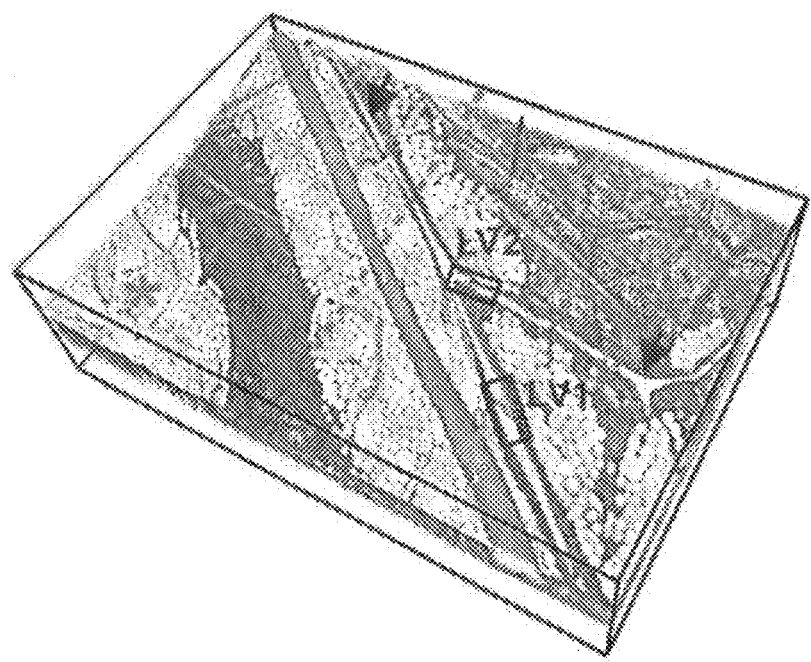

For the field of view in FIG. 15C, the following median values are calculated for features therein: blood is ~0.68; lymph is ~−0.06; tissue is ~0; and fat is ~−0.2986. A contrast between blood and tissue is calculated to be 77.5 with SC-OCTA. Noise in the lymphatics affects this calculation. Contrast between blood and lymphatics is calculated to be 4.7. The lymph has a more negative signal than tissue compared to the positive blood signal, but the lymph has a noisy signal due to manual segmentation.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Every device, system, method, probe, and combination of components, features, and steps described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for imaging a target comprising steps of:
    performing optical coherence tomography (OCT) scanning on the target with one or more beams of source light, the one or more beams of source light comprising a plurality of wavelengths; wherein performing OCT scanning comprises:
    providing the source light to a reference optical path and to a sample optical path, wherein providing the source light to a sample optical path comprises illuminating the target with the source light; and
    recording interference data corresponding to an interaction of a light from the reference optical path and a light from the sample optical path;
    processing the interference data, comprising:
    determining at least a first Fourier transform and a second Fourier transform from the interference data; wherein the first Fourier transform corresponds to a first sampling window and the second Fourier transform corresponds to a second sampling window;
    determining at least one spectral contrast OCT (SC-OCT) characteristic based on the at least the first Fourier transform and the second Fourier transform, wherein the at least one SC-OCT characteristic is at least one of a spectral contrast OCT (SC-OCT) ratio of the second Fourier transform to the first Fourier transform and a spectral contrast OCT (SC-OCT) difference between the second Fourier transform and the first Fourier transform; and
    identifying blood or one or more blood-features in the target based on an optical attenuation of light in or associated with the sample optical path by the blood or the one or more blood-features.

2. The method of claim 1, wherein the one or more blood features comprises hemoglobin, red blood cells, or any combination thereof; and the method further comprising differentiating the blood or the one or more blood-features from one or more non-blood-features in the target.

3. The method of claim 1, wherein the first Fourier transform is a first short time Fourier transform (STFT) and the second Fourier transform is a second short time Fourier transform (STFT); wherein the at least one SC-OCT characteristic is at least one of a spectral contrast OCT (SC-OCT) ratio of the second STFT to the first STFT and a spectral contrast OCT (SC-OCT) difference between the second STFT and the first STFT.

4. The method claim 1, further comprising generating a spectral contrast OCT (SC-OCT) image of the target using the SC-OCT characteristic.

5. The method of claim 4, further comprising generating a spectral contrast OCT (SC-OCT) image of the target using at least one of the SC-OCT ratio and the SC-OCT difference.

6. The method of claim 1, further comprising differentiating the blood or the one or more blood-features from the one or more non-blood-features in the target using the SC-OCT image.

7. The method of claim 1, further comprising determining an inverse of at the least one of the first Fourier transform and the second Fourier transform; and the method further comprising generating an image based on the inverse of the at least one of the first Fourier transform and the second Fourier transform.

8. The method of claim 1, further comprising performing a depth integration using the SC-OCT characteristic and generating a depth-integrated SC-OCT (DI-SC-OCT) image.

9. The method of claim 8, further comprising performing a depth integration using the SC-OCT characteristic and generating a depth-integrated SC-OCT (DI-SC-OCT) image; wherein the SC-OCT image comprises a plurality of pixels and wherein performing depth integration comprises integrating data corresponding to each of the plurality of pixels along a depth and multiplying by data corresponding to the inverse of the at least one of the first Fourier transform and the second Fourier transform.

10. The method of claim 1, further comprising determining an inverse of at the least one of the first Fourier transform and the second Fourier transform, and further comprising acquiring full-spectrum OCT data of the target and generating one or more three-dimensional (3D) images of the target using at least two of the inverse of the at least one of the first Fourier transform and the second Fourier transform, the SC-OCT characteristic, and a full-spectrum OCT data.

11. The method of claim 1, wherein determining the first Fourier transform comprises determining a first window function and the first Fourier transform corresponds to the first window function; and wherein determining the second Fourier transform comprises determining a second window function and the second Fourier transform corresponds to the second window function; wherein the first window function corresponds to a first wavelength range and the second window function corresponds to a second wavelength range; and wherein the first wavelength range and the second wavelength range are substantially in the visible light range of the electromagnetic spectrum.

12. The method of claim 11, further comprising differentiating the blood or the one or more blood-features from one or more non-blood-features in the target based on a difference in a slope of the optical attenuation with respect to wavelength corresponding to the blood or the one or more blood-features from a slope of optical attenuation with respect to wavelength corresponding to the one or more non-blood-features between a center of the first wavelength range and a center of the second wavelength range.

13. The method of claim 1, wherein performing OCT scanning comprises performing a plurality of OCT scans (a plurality of A-scans) on a plurality of locations of the target; and wherein each scan (an A-scan) of the plurality of A-scans comprises illuminating a location of the plurality of scanned locations of the target via the sample optical path.

14. The method of claim 13, wherein each location of the plurality of scanned locations substantially corresponds to only a single A-scan.

15. The method of claim 1, wherein the OCT scanning is performed using a flexible probe, and wherein at least a portion of each of the reference optical path and the sample optical path is within the flexible probe.

16. The method of claim 1, further comprising determining a concentration of a molecular marker in a bodily fluid in the imaged target, quantifying a flow of a bodily fluid in the imaged target, performing angiography of the target, and/or performing endoscopy.

17. A method for imaging a target comprising steps of:

performing optical coherence tomography (OCT) scanning on the target with one or more beams of source light, the one or more beams of source light comprising a plurality of wavelengths; wherein performing OCT scanning comprises:

providing the source light to a reference optical path and to a sample optical path, wherein providing the source light to a sample optical path comprises illuminating the target with the source light; and recording interference data corresponding to an interaction of a light from the reference optical path and a light from the sample optical path;

processing the interference data, comprising:

determining at least a first Fourier transform and a second Fourier transform from the interference data; wherein the first Fourier transform corresponds to a first sampling window and the second Fourier transform corresponds to a second sampling window;

determining at least one spectral contrast OCT (SC-OCT) characteristic based on the at least the first Fourier transform and the second Fourier transform;

performing a depth integration using the SC-OCT characteristic and generating a depth-integrated SC-OCT (DI-SC-OCT) image, wherein the SC-OCT image comprises a plurality of pixels and wherein performing depth integration comprises integrating data corresponding to each of the plurality of pixels along a depth and multiplying by data corresponding to the inverse of the at least one of the first Fourier transform and the second Fourier transform; and identifying blood or one or more blood-features in the target based on an optical attenuation of light in or associated with the sample optical path by the blood or the one or more blood-features.

* * * * *